(12) United States Patent
McSherry et al.

(10) Patent No.: US 8,017,082 B2
(45) Date of Patent: *Sep. 13, 2011

(54) APPARATUS AND METHOD FOR MAKING A PEROXYCARBOXYLIC ACID

(75) Inventors: David D. McSherry, West St. Paul, MN (US); Richard K. Staub, Lakeville, MN (US); Dan N. Tallman, New Brighton, MN (US); Junzhong Li, Apple Valley, MN (US); Keith D. Lokkesmoe, Savage, MN (US)

(73) Assignee: Ecolab USA Inc., St. Paul, MN (US)

( * ) Notice: Subject to any disclaimer, the term of this patent is extended or adjusted under 35 U.S.C. 154(b) by 102 days.

This patent is subject to a terminal disclaimer.

(21) Appl. No.: 12/430,523

(22) Filed: Apr. 27, 2009

(65) Prior Publication Data

US 2009/0208365 A1 Aug. 20, 2009

Related U.S. Application Data

(63) Continuation of application No. 11/583,371, filed on Oct. 18, 2006, now Pat. No. 7,547,421.

(51) Int. Cl.
*B01J 8/04* (2006.01)
(52) U.S. Cl. ........ 422/117; 422/608; 422/631; 422/108; 562/2; 562/6
(58) Field of Classification Search .................. 422/108, 422/117, 608, 631
See application file for complete search history.

(56) References Cited

U.S. PATENT DOCUMENTS

| 2,512,640 | A | | 6/1950 | Greenspan et al. |
| 2,910,504 | A | | 10/1959 | Hawkinson et al. |
| 2,919,283 | A | | 12/1959 | Greenspan et al. |
| 3,122,417 | A | | 2/1964 | Blaser et al. |
| 3,140,312 | A | | 7/1964 | Kurhajec et al. |
| 3,248,281 | A | | 4/1966 | Goodenough |
| 3,251,862 | A | | 5/1966 | Lidov |
| 3,350,265 | A | | 10/1967 | Rubinstein et al. |
| 3,514,278 | A | | 5/1970 | Brink |
| 3,838,516 | A | * | 10/1974 | Borochaner ............ 433/97 |
| 3,895,116 | A | | 7/1975 | Herting et al. |
| 3,929,678 | A | | 12/1975 | Laughlin et al. |
| 3,996,386 | A | | 12/1976 | Malkki et al. |
| 4,041,149 | A | | 8/1977 | Gaffar et al. |
| 4,051,058 | A | | 9/1977 | Böwing et al. |

(Continued)

FOREIGN PATENT DOCUMENTS

CA 2181416 1/1997
(Continued)

OTHER PUBLICATIONS

"Emery® Fatty and Dibasic Acids Specifications and Characteristics", *Emery Industries*, Bulletin 145 (Oct. 1983).

(Continued)

*Primary Examiner* — Jennifer A Leung
(74) *Attorney, Agent, or Firm* — Andrew D. Sorensen; Laura C. DiLorenzo

(57) ABSTRACT

The present invention relates to apparatus and methods for making a peroxycarboxylic acid. The apparatus includes a reaction catalyst and a guard column for pretreating one or more reagents, which can increase the life, activity, and/or safety of the reaction catalyst. The peroxycarboxylic acid compositions made by the method and apparatus can include one or more peroxycarboxylic acids.

9 Claims, 18 Drawing Sheets

U.S. PATENT DOCUMENTS

| | | |
|---|---|---|
| 4,051,059 A | 9/1977 | Böwing et al. |
| 4,115,410 A | 9/1978 | Watts |
| 4,129,517 A | 12/1978 | Eggensperger et al. |
| 4,191,660 A | 3/1980 | Schreiber et al. |
| 4,244,884 A | 1/1981 | Hutchins et al. |
| 4,289,728 A | 9/1981 | Peel et al. |
| 4,314,949 A | 2/1982 | Bettle, III et al. |
| 4,370,199 A | 1/1983 | Orndorff |
| 4,370,251 A | 1/1983 | Liao et al. |
| 4,404,040 A | 9/1983 | Wang |
| 4,477,438 A | 10/1984 | Willcockson et al. |
| 4,478,683 A | 10/1984 | Orndorff |
| 4,501,681 A | 2/1985 | Groult et al. |
| 4,529,534 A | 7/1985 | Richardson |
| 4,557,898 A | 12/1985 | Greene et al. |
| 4,563,272 A | 1/1986 | Yoshida et al. |
| 4,566,980 A | 1/1986 | Smith |
| 4,590,286 A | 5/1986 | Bull |
| 4,591,565 A | 5/1986 | Branner-Jorgensen |
| 4,592,488 A | 6/1986 | Simon et al. |
| 4,613,452 A | 9/1986 | Sanderson |
| 4,618,914 A | 10/1986 | Sato et al. |
| 4,650,612 A | 3/1987 | Dankowski |
| 4,655,781 A | 4/1987 | Hsieh et al. |
| 4,659,494 A | 4/1987 | Soldanski et al. |
| 4,666,622 A | 5/1987 | Martin et al. |
| 4,683,618 A | 8/1987 | O'Brien |
| 4,704,404 A | 11/1987 | Sanderson |
| 4,715,980 A | 12/1987 | Lopes et al. |
| 4,738,840 A | 4/1988 | Simon et al. |
| 4,802,994 A | 2/1989 | Mouché et al. |
| 4,818,426 A | 4/1989 | Humphreys et al. |
| 4,830,773 A | 5/1989 | Olson |
| 4,834,900 A | 5/1989 | Soldanski et al. |
| 4,865,752 A | 9/1989 | Jacobs |
| 4,900,721 A | 2/1990 | Bansemir et al. |
| 4,906,617 A | 3/1990 | Jacquet et al. |
| 4,908,306 A | 3/1990 | Lorinez |
| 4,917,815 A | 4/1990 | Beilfuss et al. |
| 4,923,677 A | 5/1990 | Simon et al. |
| 4,937,066 A | 6/1990 | Vlock |
| 4,943,414 A | 7/1990 | Jacobs et al. |
| 4,945,110 A | 7/1990 | Brokken et al. |
| 4,952,386 A | 8/1990 | Davison et al. |
| 4,996,062 A | 2/1991 | Lehtonen et al. |
| 4,997,571 A | 3/1991 | Roensch et al. |
| 4,997,625 A | 3/1991 | Simon et al. |
| 5,004,760 A | 4/1991 | Patton et al. |
| 5,010,109 A | 4/1991 | Inoi |
| 5,015,408 A | 5/1991 | Reuss |
| 5,030,380 A | 7/1991 | Moschner et al. |
| 5,043,176 A | 8/1991 | Bycroft et al. |
| 5,069,286 A | 12/1991 | Roensch et al. |
| 5,078,896 A | 1/1992 | Rorig et al. |
| 5,084,239 A | 1/1992 | Moulton et al. |
| 5,093,140 A | 3/1992 | Watanabe |
| 5,114,718 A | 5/1992 | Damani |
| 5,122,538 A | 6/1992 | Lokkesmoe et al. |
| 5,129,824 A | 7/1992 | Keller |
| 5,130,124 A | 7/1992 | Merianos et al. |
| 5,137,943 A | 8/1992 | Mark |
| 5,139,788 A | 8/1992 | Schmidt |
| 5,143,641 A | 9/1992 | Nunn |
| 5,168,655 A | 12/1992 | Davidson et al. |
| 5,176,899 A | 1/1993 | Montgomery |
| 5,184,471 A | 2/1993 | Losacco et al. |
| 5,200,189 A | 4/1993 | Oakes et al. |
| 5,208,057 A | 5/1993 | Greenley et al. |
| 5,220,052 A | 6/1993 | Troughton et al. |
| 5,234,703 A | 8/1993 | Guthery |
| 5,234,719 A | 8/1993 | Richter et al. |
| 5,262,018 A | 11/1993 | Meadow et al. |
| 5,266,587 A | 11/1993 | Sankey et al. |
| 5,268,003 A | 12/1993 | Coope et al. |
| 5,292,447 A | 3/1994 | Venturello et al. |
| 5,306,350 A | 4/1994 | Hoy et al. |
| 5,314,687 A | 5/1994 | Oakes et al. |
| 5,320,805 A | 6/1994 | Kramer et al. |
| 5,326,904 A | 7/1994 | Sankey |
| 5,336,500 A | 8/1994 | Richter et al. |
| 5,364,650 A | 11/1994 | Guthery |
| 5,391,324 A | 2/1995 | Reinhardt et al. |
| 5,409,713 A | 4/1995 | Lokkesmoe et al. |
| 5,419,908 A | 5/1995 | Richter et al. |
| 5,435,808 A | 7/1995 | Holzhauer et al. |
| 5,436,008 A | 7/1995 | Richter et al. |
| 5,437,868 A | 8/1995 | Oakes et al. |
| 5,489,434 A | 2/1996 | Oakes et al. |
| 5,489,706 A | 2/1996 | Revell |
| 5,494,588 A | 2/1996 | Lazonby |
| 5,505,740 A | 4/1996 | Kong et al. |
| 5,508,046 A | 4/1996 | Cosentino et al. |
| 5,512,309 A | 4/1996 | Bender et al. |
| 5,527,898 A | 6/1996 | Bauer et al. |
| 5,545,343 A | 8/1996 | Brougham et al. |
| 5,545,374 A | 8/1996 | French et al. |
| 5,578,134 A | 11/1996 | Lentsch et al. |
| 5,591,706 A | 1/1997 | Ploumen |
| 5,595,967 A | 1/1997 | Miracle et al. |
| 5,597,790 A | 1/1997 | Thoen |
| 5,616,335 A | 4/1997 | Nicolle et al. |
| 5,616,616 A | 4/1997 | Hall et al. |
| 5,624,634 A | 4/1997 | Brougham et al. |
| 5,632,676 A | 5/1997 | Kurschner et al. |
| 5,641,530 A | 6/1997 | Chen |
| 5,656,302 A | 8/1997 | Cosentino et al. |
| 5,658,467 A | 8/1997 | Lazonby et al. |
| 5,658,595 A | 8/1997 | Van Os |
| 5,674,538 A | 10/1997 | Lokkesmoe et al. |
| 5,674,828 A | 10/1997 | Knowlton et al. |
| 5,683,724 A | 11/1997 | Hei et al. |
| 5,712,239 A | 1/1998 | Knowlton et al. |
| 5,718,910 A | 2/1998 | Oakes et al. |
| 5,720,983 A | 2/1998 | Malone |
| 5,756,139 A | 5/1998 | Harvey et al. |
| 5,785,867 A | 7/1998 | Lazonby et al. |
| 5,840,343 A | 11/1998 | Hall et al. |
| 5,851,483 A | 12/1998 | Nicolle et al. |
| 5,866,005 A | 2/1999 | DeSimone et al. |
| 5,891,392 A | 4/1999 | Monticello et al. |
| 5,900,256 A | 5/1999 | Scoville, Jr. et al. |
| 5,902,619 A | 5/1999 | Rubow et al. |
| 5,968,539 A | 10/1999 | Beerse et al. |
| 5,977,403 A | 11/1999 | Byers |
| 5,989,611 A | 11/1999 | Stemmler, Jr. et al. |
| 5,998,358 A | 12/1999 | Herdt et al. |
| 6,008,405 A | 12/1999 | Gray et al. |
| 6,010,729 A | 1/2000 | Gutzmann et al. |
| 6,024,986 A | 2/2000 | Hei |
| 6,028,104 A | 2/2000 | Schmidt et al. |
| 6,033,705 A | 3/2000 | Isaacs |
| 6,039,992 A | 3/2000 | Compardre et al. |
| 6,049,002 A | 4/2000 | Mattila et al. |
| 6,080,712 A | 6/2000 | Revell et al. |
| 6,096,226 A | 8/2000 | Fuchs et al. |
| 6,096,266 A | 8/2000 | Duroselle |
| 6,096,348 A | 8/2000 | Miner et al. |
| 6,103,286 A | 8/2000 | Gutzmann et al. |
| 6,111,963 A | 8/2000 | Thompson, III |
| 6,113,963 A | 9/2000 | Gutzmann et al. |
| 6,165,483 A | 12/2000 | Hei et al. |
| 6,183,807 B1 | 2/2001 | Gutzmann et al. |
| 6,238,685 B1 | 5/2001 | Hei et al. |
| 6,257,253 B1 | 7/2001 | Lentsch et al. |
| 6,274,542 B1 | 8/2001 | Carr et al. |
| 6,296,829 B1 | 10/2001 | Devos et al. |
| 6,302,968 B1 | 10/2001 | Baum et al. |
| 6,395,703 B2 | 5/2002 | Scepanski |
| 6,423,868 B1 | 7/2002 | Carr et al. |
| 6,451,746 B1 | 9/2002 | Moore et al. |
| 6,514,556 B2 | 2/2003 | Hilgren et al. |
| 6,545,047 B2 | 4/2003 | Gutzmann et al. |
| 6,627,657 B1 | 9/2003 | Hilgren et al. |
| 6,630,439 B1 | 10/2003 | Norwood et al. |
| 6,635,286 B2 | 10/2003 | Hei et al. |
| 6,638,902 B2 | 10/2003 | Tarara et al. |
| 6,674,538 B2 | 1/2004 | Takahashi |

| | | |
|---|---|---|
| 6,783,748 B2 | 8/2004 | Tanaka et al. |
| 6,949,178 B2 | 9/2005 | Tennakoon et al. |
| 7,012,154 B2 | 3/2006 | Vineyard et al. |
| 7,150,884 B1 | 12/2006 | Hilgren et al. |
| 7,547,421 B2 * | 6/2009 | McSherry et al. ............ 422/424 |
| 2002/0128312 A1 | 9/2002 | Hei et al. |
| 2002/0168422 A1 | 11/2002 | Hei et al. |
| 2003/0070691 A1 | 4/2003 | Giletto et al. |
| 2003/0087786 A1 | 5/2003 | Hei et al. |
| 2003/0199583 A1 | 10/2003 | Gutzmann et al. |
| 2004/0143133 A1 | 7/2004 | Smith et al. |
| 2004/0202588 A1 * | 10/2004 | Tanaka et al. ................. 422/110 |
| 2005/0152991 A1 | 7/2005 | Man et al. |
| 2005/0192197 A1 | 9/2005 | Man et al. |

FOREIGN PATENT DOCUMENTS

| | | |
|---|---|---|
| CA | 2400625 | 9/2001 |
| DE | 3003875 | 8/1981 |
| DE | 3543500 | 6/1987 |
| DE | 3906044 | 8/1990 |
| DE | 19751391 | 7/1998 |
| DK | 9300538 | 11/1994 |
| EP | 0017681 | 5/1983 |
| EP | 0167375 | 1/1986 |
| EP | 0186052 | 7/1986 |
| EP | 0195619 | 9/1986 |
| EP | 0125781 | 8/1987 |
| EP | 0233731 | 8/1987 |
| EP | 0242990 | 10/1987 |
| EP | 0105689 | 12/1987 |
| EP | 269435 | 6/1988 |
| EP | 0140648 | 3/1989 |
| EP | 0168587 | 7/1989 |
| EP | 0361955 | 4/1990 |
| EP | 0404293 | 12/1990 |
| EP | 0461700 | 12/1991 |
| EP | 0569066 | 11/1993 |
| EP | 0540515 | 2/1995 |
| EP | 0667392 | 8/1995 |
| EP | 0460962 | 12/1995 |
| EP | 0779357 | 6/1997 |
| EP | 0603329 | 8/1997 |
| EP | 0805198 | 11/1997 |
| EP | 0843001 | 5/1998 |
| EP | 0967203 | 12/1999 |
| EP | 0985349 | 3/2000 |
| EP | 0946506 | 9/2003 |
| EP | 1382666 | 1/2004 |
| FR | 2324626 | 4/1977 |
| FR | 2578988 | 9/1986 |
| FR | 2321301 | 3/1997 |
| GB | 1494109 | 12/1977 |
| GB | 2020257 | 11/1979 |
| GB | 1570492 | 7/1980 |
| GB | 2182051 | 5/1987 |
| GB | 2187958 | 9/1987 |
| GB | 2207354 | 2/1989 |
| GB | 2255507 | 11/1992 |
| GB | 2257630 | 1/1993 |
| GB | 2353800 | 3/2001 |
| JP | 7-31210 | 2/1995 |
| JP | 7-258005 | 10/1995 |
| JP | 11-349560 | 12/1999 |
| JP | 2000-290251 | 10/2000 |
| JP | 2000290251 A * | 10/2000 |
| LU | 78568 | 4/1978 |
| NL | 9201631 | 9/1992 |
| RU | 2102447 | 1/1998 |
| WO | WO93/01716 | 2/1993 |
| WO | WO94/06294 | 3/1994 |
| WO | WO94/14321 | 7/1994 |
| WO | WO94/15465 | 7/1994 |
| WO | WO94/21122 | 9/1994 |
| WO | WO94/23575 | 10/1994 |
| WO | WO95/34537 | 12/1995 |
| WO | WO96/30474 | 10/1996 |
| WO | WO98/28267 | 7/1998 |
| WO | WO99/51095 | 10/1999 |
| WO | WO00/18870 | 4/2000 |
| WO | WO01/47359 | 7/2001 |
| WO | WO02/03799 | 1/2002 |
| WO | WO02/054866 | 7/2002 |
| WO | WO02/060280 | 8/2002 |
| WO | WO2004/043162 | 5/2004 |

OTHER PUBLICATIONS

Abstract: "Indirect food additives: adjuvants, production aids, and sanitizers", *Fed. Register*, vol. 61, No. 108, pp. 28051-28053 (Jun. 4, 1996) (1 page abstract).

Armak Chemicals, "NEO-FAT Fatty Acids", *Akzo Chemicals Inc.*, Bulletin No. 86-17 (1986).

Baldry, M. et al., "Disinfection of Sewage Effluent with Peracetic Acid," *Water Science and Technology*, vol. 21, No. 3, pp. 203-206 (1989).

Baldry, M. et al., Disinfection with peroxygens, *Industrial Biocides*, edited by K.R. Payne, New York, John Wiley & Sons, pp. 91-116 (1988).

Baldry, M., "The bactericidal, fungicidal and sporicidal properties of hydrogen peroxide and peracetic acid," *Journal of Applied Bacteriology*, vol. 54, pp. 417-423 (1983).

Bayliss et al., "The Synergistic Killing of Spores of *Bacillus subtilis* by Hydrogen Peroxide and Ultra-Violet Light Irradiation," *FEMS Microbiology Letters*, vol. 5, pp. 331-333 (1979).

Bell, K. et al., "Reduction of foodborne micro-organisms on beef carcass tissue using acetic acid, sodium bicarbonate, and hydrogen peroxide spray washes", *Food Microbiology*, vol. 14, pp. 439-448 (1997).

Beuchat, L., "Surface Disinfection of Raw Produce," *Dairy, Food and Environmental Sanitation*, vol. 12, No. 1, pp. 6-9 (Jan. 1992).

Block, S., "Peroxygen Compounds," *Disinfection, Sterilization, and Preservation*, Fourth Edition, Chapter 9, pp. 167-181 (1991).

Block, S., "Peroxygen Compounds," *Disinfection, Sterilization, and Preservation*, Fifth Edition, Chapter 9, pp. 185-204 (2001).

Breen, P. et al. "Elimination of *Salmonella* Contamination from Poultry Tissues by Cetylpyridinium Chloride Solutions", *Journal of Food Protection*, vol. 60, No. 9, pp. 1019-1021 (1997).

Breen, P. et al., "Quaternary Ammonium Compounds Inhibit and Reduce the Attachment of Viable *Salmonella typhimurium* to Poultry Tissues", *Journal of Food Science*, vol. 60, No. 6, pp. 1191-1196 (1995).

Brown, G. et al., "Use of *Xanthomonas campestris* pv. *vesicatoria* to Evaluate Surface Disinfectants for Canker Quarantine Treatment of Citrus Fruit," *Plant Disease*, vol. 71, No. 1, pp. 319-323 (Apr. 1987).

Computer search results—Level 1-5 patents, 4 pages (Mar. 1994).

Computer search results from Ecolab Information Center, pp. 1-30 (Jun. 1998).

International Search Report dated Dec. 27, 2002.

International Search Report dated Jan. 30, 2002.

International Search Report dated Jul. 4, 2005 (PCT/US2005/000147).

International Search Report dated Jun. 28, 2005 (PCT/US2005/000231).

International Search Report dated Jun. 28, 2006 (PCT/US2005/000149).

International Search Report dated Jun. 3, 2002.

International Search Report dated May 3, 2005.

Cords, B., "New Peroxyacetic Acid Sanitizer", *Proceedings*, Twenty-Third Convention, Institute of Brewing, Sydney Australia, pp. 165-169 (1994).

Dickens, J. et al. "Effects of Acetic Acid and Hydrogen Peroxide Application During Defeathering on the Microbiological Quality of Broiler Carcasses Prior to Evisceration", *Poultry Science*, vol. 76, pp. 657-660 (1997).

Dickens, J. et al. "Microbiological Decontamination of Food Animal Carcasses by Washing and Sanitizing Systems: A Review", *Journal of Food Protection*, vol. 55, No. 2, pp. 133-140 (Feb. 1992).

Dickens, J. et al. "The Effects of Extended Chilling Times with Acetic Acid on the Temperature and Microbiological Quality of Processed Poultry Carcasses", *Poultry Science*, vol. 74, pp. 1044-1048 (1995).

Dickens, J. et al., "The Effect of Acetic Acid and Air Injection on Appearance, Moisture Pick-Up, Microbiological Quality, and *Salmonella* Incidence of Processed Poultry Carcasses", *Poultry Science*, vol. 73, pp. 582-586 (1994).

Dickens, J. et al., "The Effect of an Acetic Acid Dip on Carcass Appearance, Microbiological Quality, and Cooked Breast Meat Texture and Flavor", *Poultry Science*, vol. 73, pp. 576-581 (1994).

Eggensperger, H., "Disinfectants Based on Peracid-Splitting Compounds", *Zbl. Bakt. Hyg.*, I. Abt. Orig. B 168, pp. 517-524 (1979).

Focus on Interox, *Effluent+Water Treatment Journal*, 4 pages (Aug. 1979).

Fraser, J., "Novel applications of peracetic acid in industrial disinfection," *Specialty Chemicals*, vol. 7, No. 3, pp. 178, 180, 182, 184, 196 (1987).

FSTA abstract, accession No. 1999(10):C1223, abstracting: *Journal of Food Protection*, vol. 62, No. 7, pp. 761-765 (1999) (1 page abstract).

FSTA abstract, accession No. 2000(06):J1220, abstracting: *Dairy, Food and Environmental Sanitation*, vol. 19, No. 12, pp. 842-847 (1999) (1 page abstract).

Greenspan, F. et al., "The Application of Peracetic Acid Germicidal Washes to Mold Control of Tomatoes," *Food Technology*, vol. 5, No. 3, pp. 95-97 (Mar. 1951).

Han, B. et al., "Destruction of Bacterial Spores on Solid Surfaces," *Journal of Food Processing and Preservation*, vol. 4, Nos. 1-2, pp. 95-110 (1980).

Heinemann, P., "The Germidical Efficiency of Commercial Preparations of Hydrogen Peroxide," *The Journal of the American Medical Association*, vol. LX, No. 21, pp. 1603-1606 (1913).

Hutchings, I. et al., "A9. Comparative Evaluation of the Bactericidal Efficiency of Peracetic Acid, Quaternaries, and Chlorine-Containing Compounds," *Abstract of Papers Presented at the 49th General Meeting of the Society of American Bacteriologists*, pp. 50-51 (1949) (Abstract).

International Search Report and Written Opinion dated Mar. 28, 2008 from PCT/IB2007/053809.

Interox Chemicals Ltd. Product brochure entitled: OXYMASTER Peracetic Acid 12%, 12 pages.

Interox Chemicals Ltd. Product brochure entitled: PROXITANE 4002 Peracetic Acid 36-40%, 8 pages.

Jager et al., Peracetic acid as a disinfectant in breweries and soft drink factories, *Mitt. Versuch. Gaorung. Wien.*, vol. 34, pp. 32-36 (1980).

Kim, J. et al., "Cetylpyridinium Chloride (CPC) Treatment on Poultry Skin to Reduce Attached *Salmonella*", *Journal of Food Protection*, vol. 59, No. 3, pp. 322-326 (1995).

Kunzmann, T., "Investigations on the disinfecting action of hydrogen peroxides," Fortschr. Med., vol. 52, No. 16 pp. 357-359 (1934).

Laska, M. et al. "Odor structure-activity relationships of carboxylic acids correspond between squirrel monkeys and humans", *Am. J. Physiol.*, vol. 274, pp. R1639-R1645 (1998).

Lillard H., "Factors Affecting the Persistence of *Salmonella* During the Processing of Poultry", *Journal of Food Protection*, vol. 52, No. 11, pp. 829-832 (Nov. 1989).

Lillard, H., "Bacterial Cell Characteristics and Conditions Influencing their Adhesion to Poultry Skin" *Journal of Food Protection*, vol. 48, No. 9, pp. 803-807 (Sep. 1985).

Lion C. et al., "New decontaminants. Reaction of peroxyacid esters with toxic insecticides", *Bull, Soc. Chim. Belg.*, vol. 100, No. 7, pp. 555-559 (1991).

Merka, V. et al., "Disinfectant properties of some peroxide compounds", *Chemical Abstracts*, Abstract No. 67542e. vol. 67, p. 6368 (1967).

MicroPatent Report dated Aug. 18, 2003.

Mulder, R. et al., "Research Note: *Salmonella* Decontamination of Broiler Carcasses with Lactic Acid, L-Cysteine, and Hydrogen Peroxide", *Poultry Science*, vol. 66, pp. 1555-1557 (1987).

Nambudripad, V. et al. "Bactericidal Efficiency of Hydrogen Peroxide. Part I. Influence of different concentrations on the rate and extent of destruction of some bacteria of dairy importance," *Indian Journal of Dairy Science*, vol. 4, pp. 65-69 (1949).

Opinion Letter dated Apr. 11, 2000.

Orth, R. et al., "Is the control of *Listeria, Campylobacter* and *Yersinia* a disinfection problem?", *Fleischwirtsch*, vol. 69, No. 10, pp. 1575-1576 (1989).

Parker, W. et al., "Peroxides. II. Preparation, Characterization and Polarographic Behavior of Longchain Aliphatic Peracids", *Synthesis and Properties of LongChain Aliphatic Peracids*, vol. 77, pp. 4037-4041 (Aug. 5, 1955).

Parker, W. et al., "Peroxides. IV. Aliphatic Diperacids", *Aliphatic Diperacids*, vol. 79, pp. 1929-1931 (Apr. 20, 1957).

Pfizer Chemical Division, "Pfizer Flocon® Biopolymers for Industrial Uses (xanthan broths)", Data Sheet 679, pp. 1-4 (year unknown).

Poffe, R. et al., "Disinfection of Effluents from Municipal Sewage Treatment Pants with Peroxy Acids" *Zbl. Bakt. Hyg., I Abt Orig.* B 167, pp. 337-346 (1978).

Ranganna, S. et al., "Chemical Preservatives and Anti-oxidants," *Indian Food Packer*, pp. 30-45 (May-Jun. 1981).

Richardson, B., "On Peroxide of Hydrogen, or Ozone Water, as a Remedy," *The Lancet*, pp. 707-709, 760-763 (Mar. 1891).

Search Report for the use of amine oxides with hydrogen peroxide in bleaching, sanitizing, disinfectant or hard surface cleaners, pp. 2-49, (1998).

Search Result from Database WPI and Database INPADOC, 5 pages, (1998).

Search Results (2003), 19 pages.

Sims, A., "Industrial effluent treatment with hydrogen peroxide," *Chemistry and Industry*, No. 14, pp. 555-558 (Jul. 18, 1983).

Solvay product brochure entitled: Oxymaster® Proxitane® Peracetic Acid Applications, 8 pages, (1998).

Solvay product brochure entitled: Oxymaster® Proxitane® Peracetic Acid Solutions; Handling, Storage and Transport Information (Safety Documentation) pp. 1-22, (1999).

Tamblyn, K. et al., "Bactericidal Activity of Organic Acids against *Salmonella typhimurlum* Attached to Broiler Chicken Skin", *Journal of Food Protection*, vol. 60, No. 6, pp. 629-633 (1997).

Taylor, J. et al., "A comparison of the bactericidal efficacy of 18 disinfectants used in the food industry against *Escherichia coli* O157:H7 and *Pseudomonas aeruginosa* as 10 and 20° C", *Journal of Applied Microbiology*, vol. 87, pp. 718-725 (1999).

Towle, G. et al., "Pectin", *Industrial Gums polysaccharides and Their Derivatives* Second Edition, Ch. XIX, pp. 429-444 (year unknown).

Xiong, H. et al., "Spraying Chicken with Selected Chemicals to Reduce Attached *Salmonella typhimurium*", *Journal of Food Protection*, vol. 61, No. 3, pp. 272-275 (1998).

Yoshpe-Parer, Y. et al. "Disinfection of Water by Hydrogen Peroxide," *Health Laboratory Science*, vol. 5, No. 4, pp. 233-238 (Oct. 1968).

\* cited by examiner

APPARATUS AND METHOD FOR MAKING A PEROXYCARBOXYLIC ACID

CROSS REFERENCE TO RELATED APPLICATION

This application is a continuation of U.S. patent application Ser. No. 11/583,371, filed Oct. 18, 2006, now issued as U.S. Pat. No. 7,547,421. It is also related to U.S. patent application Ser. No. 12/108,202, filed Apr. 23, 2008, published as 2008-0275132, the entire disclosure of both of which are incorporated herein by reference in their entirety.

FIELD OF THE INVENTION

The present invention relates to apparatus and methods for making a peroxycarboxylic acid. The apparatus includes a reaction catalyst and a pretreatment column for pretreating one or more reagents, which can increase the life, activity, and/or safety of the reaction catalyst. The peroxycarboxylic acid compositions made by the method and apparatus can include one or more peroxycarboxylic acids.

BACKGROUND OF THE INVENTION

Present methods for making peroxycarboxylic acids include mixing a carboxylic acid or anhydride with an oxidizing agent, such as hydrogen peroxide, in water and waiting. At ambient conditions, the reaction can take a week or more to reach desirable concentrations of peroxycarboxylic acid at equilibrium. In addition, regulations regarding and practices in shipping of ingredients such as hydrogen peroxide and acetic acid can limit the concentration, stability, content, or purity of these reagents and, therefore, of the resulting peroxycarboxylic acid. For example, acetic acid inevitably contains metal due to common shipping and handling practices. Conventional peroxycarboxylic acid compositions typically include short chain peroxycarboxylic acids or mixtures of short chain peroxycarboxylic acids and medium chain peroxycarboxylic acids (see, e.g., U.S. Pat. Nos. 5,200,189, 5,314,687, 5,409,713, 5,437,868, 5,489,434, 6,674,538, 6,010,729, 6,111,963, and 6,514,556).

Ongoing research efforts have strived for improved peroxycarboxylic acid compositions and methods of making them. In particular, these efforts have strived for methods that can more rapidly make purer and/or more stable peroxycarboxylic compositions even at a point of use.

SUMMARY OF THE INVENTION

The present invention relates to apparatus and methods for making a peroxycarboxylic acid. The apparatus includes a reaction catalyst and a pretreatment column for pretreating one or more reagents, which can increase the life, activity, and/or safety of the reaction catalyst. The peroxycarboxylic acid compositions made by the method and apparatus can include one or more peroxycarboxylic acids.

The present invention includes an apparatus for making peroxycarboxylic acid. In an embodiment, this apparatus can include a first pretreatment column, a first reaction catalyst column, a first and a second reagent vessel, a plurality of conduits, and a safety system. The first and second reagent vessels are in fluid communication with the first pretreatment column. The first pretreatment column is in fluid communication with the first reaction catalyst column. The first reaction catalyst column can be in fluid communication with a site of storage or use of the peroxycarboxylic acid composition.

The first reagent vessel can be configured for containing a liquid hydrogen peroxide composition and the second reagent vessel can be configured for containing a liquid carboxylic acid composition. The safety system can be configured to measure temperature, pressure, metal content, or combination thereof of the hydrogen peroxide and carboxylic acid composition in, at, or before entry to the pretreatment column.

The present method includes a method for making a peroxycarboxylic acid. In an embodiment the method includes pretreating a liquid composition of a carboxylic acid, hydrogen peroxide, or both with a pretreatment column. The method can optionally include mixing the pretreated liquid composition with a liquid composition of carboxylic acid, hydrogen peroxide or both to yield a composition comprising carboxylic acid and hydrogen peroxide. The method then includes reacting the composition comprising carboxylic acid and hydrogen peroxide in the presence of a reaction catalyst to produce a peroxycarboxylic acid composition and recovering the peroxycarboxylic acid composition. The method includes monitoring temperature, pressure, or metal content of the carboxylic acid, hydrogen peroxide, or both before pretreating, during pretreating, or both. If the temperature, difference in temperatures, pressure, difference in pressures, metal content, or difference in metal content exceeds a predetermined value, the method includes actuating a pressure release valve, stopping flow of one or more reagents, causing water to flow into the apparatus, causing carboxylic acid composition to flow into the apparatus, shutting down the method, or a combination thereof.

BRIEF DESCRIPTION OF THE DRAWINGS

Various embodiments of the present invention will be described in detail with reference to the drawings, wherein like reference numerals represent like parts throughout the several views. Reference to various embodiments does not limit the scope of the invention, which is limited only by the scope of the claims.

DETAILED DESCRIPTION OF THE INVENTION

Definitions

Figure 1:
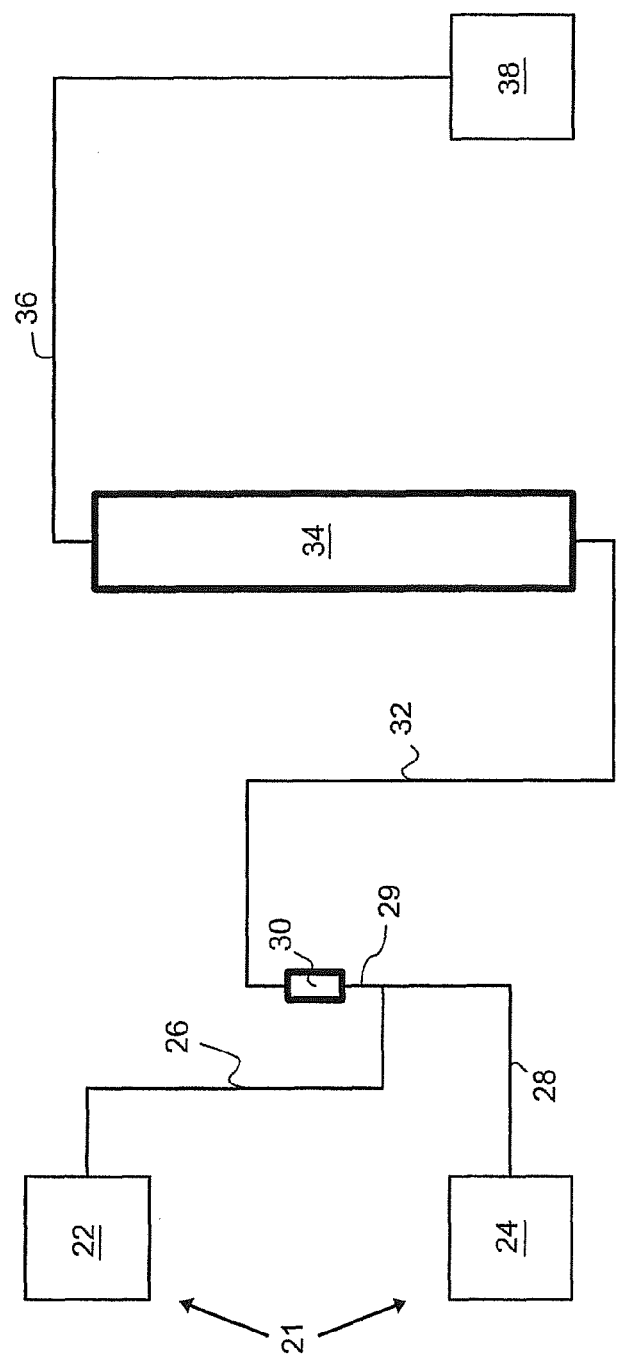
FIGS. 1-5 schematically represent embodiments of apparatus that generates peroxycarboxylic acid including embodiments of pretreatment column and reaction catalyst.

As used herein, the phrase "medium chain carboxylic acid" refers to a carboxylic acid that: 1) has reduced or is lacking odor compared to the bad, pungent, or acrid odor associated with an equal concentration of small chain carboxylic acid, and 2) has a critical micellar concentration greater than 1 mM in aqueous buffers at neutral pH. Medium chain carboxylic acids exclude carboxylic acids that are infinitely soluble in or miscible with water at 20° C. Medium chain carboxylic acids include carboxylic acids with boiling points (at 760 mm Hg pressure) of 180 to 300° C. In an embodiment, medium chain carboxylic acids include carboxylic acids with boiling points (at 760 mm Hg pressure) of 200 to 300° C. In an embodiment, medium chain carboxylic acids include those with solubility in water of less than 1 g/L at 25° C. Examples of medium chain carboxylic acids include pentanoic acid, hexanoic acid, heptanoic acid, octanoic acid, nonanoic acid, decanoic acid, undecanoic acid, and dodecanoic acid.

As used herein, the phrase "medium chain peroxycarboxylic acid" refers to the peroxycarboxylic acid form of a medium chain carboxylic acid.

As used herein, the phrase "short chain carboxylic acid" refers to a carboxylic acid that: 1) has characteristic bad, pungent, or acrid odor, and 2) is infinitely soluble in or miscible with water at 20° C. Examples of short chain carboxylic acids include formic acid, acetic acid, propionic acid, and butyric acid.

As used herein, the phrase "short chain peroxycarboxylic acid" refers to the peroxycarboxylic acid form of a short chain carboxylic acid.

As used herein the term "inert metal cations" refers to those metal cations which are substantially unreactive (e.g., do not undergo an undesirable level of reaction) or unreactive with hydrogen peroxide or a peroxycarboxylic acid (i.e., peroxygen species). For example, sodium and potassium are inert metal cations, whereas iron and copper are not.

As used herein, the term "insoluble" is used to describe a substance that does not dissolve to give more than a negligible concentration (e.g., <0.1 mg/mL) in a carrier or solvent employed for the carboxylic acid, oxidizing agent, peroxycarboxylic acid, or combination thereof to give a reasonable concentration.

As used herein, a composition or combination "consisting essentially" of certain ingredients refers to a composition including those ingredients and lacking any ingredient that materially affects the basic and novel characteristics of the composition or method. The phrase "consisting essentially of" excludes from the claimed compositions and methods a sequestrant, builder, chelating agent, or stabilizing agent; unless such a process or ingredient is specifically listed after the phrase.

As used herein, a composition or combination "substantially free of" one or more ingredients refers to a composition that includes none of that ingredient or that includes only trace or incidental amounts of that ingredient. Trace or incidental amounts can include the amount of the ingredient found in another ingredient as an impurity or stabilizer or that is generated in a minor side reaction during formation or degradation of the peroxycarboxylic acid. For example, commercially available hydrogen peroxide often contains minor amounts of a stabilizer such as a tin compound or in some cases trace amounts of HEDP.

As used herein, the phrases "objectionable odor", "offensive odor", or "malodor" refer to a sharp, pungent, or acrid odor or atmospheric environment from which a typical person withdraws if they are able to. Hedonic tone provides a measure of the degree to which an odor is pleasant or unpleasant. An "objectionable odor", "offensive odor", or "malodor" has an hedonic tone rating it as unpleasant as or more unpleasant than a solution of 5 wt-% acetic acid, propionic acid, butyric acid, or mixtures thereof.

As used herein, the term "microorganism" refers to any noncellular or unicellular (including colonial) organism. Microorganisms include all prokaryotes. Microorganisms include bacteria (including cyanobacteria), lichens, fungi, protozoa, virinos, viroids, viruses, phages, and some algae. As used herein, the term "microbe" is synonymous with microorganism.

As used herein, the term "object" refers to a something material that can be perceived by the senses, directly and/or indirectly. Objects include a surface, including a hard surface (such as glass, ceramics, metal, natural and synthetic rock, wood, and polymeric), an elastomer or plastic, woven and non-woven substrates, a food processing surface, a health care surface, and the like. Objects also include a food product (and its surfaces); a body or stream of water or a gas (e.g., an air stream); and surfaces and articles employed in hospitality and industrial sectors. Objects also include the body or part of the body of a living creature, e.g., a hand.

As used herein, the phrase "food product" includes any food substance that might require treatment with an antimicrobial agent or composition and that is edible with or without further preparation. Food products include meat (e.g. red meat and pork), seafood, poultry, fruits and vegetables, eggs, living eggs, egg products, ready to eat food, wheat, seeds, roots, tubers, leafs, stems, corms, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the phrase "plant product" includes any plant substance or plant-derived substance that might require treatment with an antimicrobial agent or composition. Plant products include seeds, nuts, nut meats, cut flowers, plants or crops grown or stored in a greenhouse, house plants, and the like. Plant products include many animal feeds.

As used herein, a processed fruit or vegetable refers to a fruit or vegetable that has been cut, chopped, sliced, peeled, ground, milled, irradiated, frozen, cooked (e.g., blanched, pasteurized), or homogenized. As used herein a fruit or vegetable that has been washed, colored, waxed, hydro-cooled, refrigerated, shelled, or had leaves, stems or husks removed is not processed.

As used herein, the phrase "meat product" refers to all forms of animal flesh, including the carcass, muscle, fat, organs, skin, bones and body fluids and like components that form the animal. Animal flesh includes the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "poultry debris" refers to any debris, residue, material, dirt, offal, poultry part, poultry waste, poultry viscera, poultry organ, fragments or combinations of such materials, and the like removed from a poultry carcass or portion during processing and that enters a waste stream.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, autodish sanitizers, sanitizing gels, cooling towers, food processing antimicrobial garment sprays, and non-to-low-aqueous food preparation lubricants, oils, and rinse additives.

As used herein, the phrase "air streams" includes food anti-spoilage air circulation systems. Air streams also include air streams typically encountered in hospital, surgical, infirmity, birthing, mortuary, and clinical diagnosis rooms.

As used herein, the term "waters" includes food process or transport waters. Food process or transport waters include produce transport waters (e.g., as found in flumes, pipe transports, cutters, slicers, blanchers, retort systems, washers, and the like), belt sprays for food transport lines, boot and hand-wash dip-pans, third-sink rinse waters, and the like. Waters also include domestic and recreational waters such as pools, spas, recreational flumes and water slides, fountains, and the like.

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the various medical or dental instruments or devices that can benefit from cleaning with a stabilized composition according to the present invention.

As used herein, the phrases "medical instrument", "dental instrument", "medical device", "dental device", "medical equipment", or "dental equipment" refer to instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present invention. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressors, trocars, dilators, cages, glassware, tubing, catheters, cannulas, plugs, stents, scopes (e.g., endoscopes, stethoscopes, and arthoscopes) and related equipment, and the like, or combinations thereof.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, "residential" or "institutional" objects or surfaces include those found in structures inhabited by humans. Such objects or surfaces include bathroom surfaces, drains, drain surfaces, kitchen surfaces, and the like.

As used herein, the phrase "densified fluid" refers to a fluid in a critical, subcritical, near critical, or supercritical state. The fluid is generally a gas at standard conditions of one atmosphere pressure and 0° C. As used herein, the phrase "supercritical fluid" refers to a dense gas that is maintained above its critical temperature, the temperature above which it cannot be liquefied by pressure. Supercritical fluids are typically less viscous and diffuse more readily than liquids. In an embodiment, a densified fluid is at, above, or slightly below its critical point. As used herein, the phrase "critical point" is the transition point at which the liquid and gaseous states of a substance merge into each other and represents the combination of the critical temperature and critical pressure for a substance. The critical pressure is a pressure just sufficient to cause the appearance of two phases at the critical temperature. Critical temperatures and pressures have been reported for numerous organic and inorganic compounds and several elements.

As used herein, the terms "near critical" fluid or "subcritical" fluid refer to a fluid material that is typically below the critical temperature of a supercritical fluid, but remains in a fluid state and denser than a typical gas due to the effects of pressure on the fluid. In an embodiment, a subcritical or near critical fluid is at a temperature and/or pressure just below its critical point. For example, a subcritical or near critical fluid can be below its critical temperature but above its critical pressure, below its critical pressure but above its critical temperature, or below both its critical temperature and pressure. The terms near critical and subcritical do not refer to materials in their ordinary gaseous or liquid state.

As used herein, weight percent (wt-%), percent by weight, % by weight, and the like are synonyms that refer to the concentration of a substance as the weight of that substance divided by the weight of the composition and multiplied by 100. Unless otherwise specified, the quantity of an ingredient refers to the quantity of active ingredient.

As used herein, the terms "mixed" or "mixture" when used relating to "peroxycarboxylic acid composition" or "peroxycarboxylic acids" refer to a composition or mixture including more than one peroxycarboxylic acid, such as a composition or mixture including peroxyacetic acid and peroxyoctanoic acid.

As used herein, the term "about" modifying the quantity of an ingredient in the compositions of the invention or employed in the methods of the invention refers to variation in the numerical quantity that can occur, for example, through typical measuring and liquid handling procedures used for making concentrates or use solutions in the real world; through inadvertent error in these procedures; through differences in the manufacture, source, or purity of the ingredients employed to make the compositions or carry out the methods; and the like. The term about also encompasses amounts that differ due to different equilibrium conditions for a composition resulting from a particular initial mixture. Whether or not modified by the term "about", the claims include equivalents to the quantities.

For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "sanitizer" refers to an agent that reduces the number of bacterial contaminants to safe levels as judged by public health requirements. In an embodiment, sanitizers for use in this invention will provide at least a 99.999% reduction (5-log order reduction). These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "disinfectant" refers to an agent that kills all vegetative cells including most recognized pathogenic microorganisms, using the procedure described in *A.O.A.C. Use Dilution Methods*, Official Methods of Analysis of the Association of Official Analytical Chemists, paragraph 955.14 and applicable sections, 15th Edition, 1990 (EPA Guideline 91-2).

As used in this invention, the term "sporicide" refers to a physical or chemical agent or process having the ability to cause greater than a 90% reduction (1-log order reduction) in the population of spores of *Bacillus cereus* or *Bacillus subtilis* within 10 seconds at 60° C. In certain embodiments, the sporicidal compositions of the invention provide greater than a 99% reduction (2-log order reduction), greater than a 99.99% reduction (4-log order reduction), or greater than a 99.999% reduction (5-log order reduction) in such population within 10 seconds at 60° C.

Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can effect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition.

Apparatus for Making Peroxycarboxylic Acid

The present invention relates to an apparatus for making a peroxycarboxylic acid and to methods employing the apparatus. The apparatus includes a reaction catalyst and a pretreatment column. The pretreatment column pretreats one or more of the reagents employed in making the peroxycarboxylic acid. For example, a cation exchanger in acid form or inert metal (e.g., $Na^+$ or $K^+$) form can remove positively charged contaminants, such as metal ion, from hydrogen peroxide, carboxylic acid, or a mixture of hydrogen peroxide and carboxylic acid. The reaction catalyst catalyzes the reaction of carboxylic acid (or suitable precursor) with an oxidizing agent (e.g., a peroxide, a peroxide donor, such as a hydrogen peroxide donor) to form a peroxycarboxylic acid. For example, an reaction catalyst that is a strong acid (e.g., a polystyrene sulfonic acid) can catalyze reaction of hydrogen peroxide with carboxylic acid to form peroxycarboxylic acid. The pretreatment column can increase the life, activity, and/or safety of the reaction catalyst.

The apparatus can also include a safety system. The safety system can monitor and/or regulate one or more conditions of the pretreatment column and/or the reaction catalyst. For example, the safety system can monitor and/or regulate the pressure, temperature, metal content, and/or presence of gas resulting from decay of peroxide (e.g., oxygen). The safety system can measure one or more of these parameters at or in the pretreatment column, at or in the reaction catalyst, for one or more of the reagents before, in, or after a pretreatment column, for the reaction mixture before, in, or after a pretreatment column, for the reaction mixture before, in, or after the reaction catalyst, or more than one of these (a combination thereof). The safety system can measure a difference in one or more of these parameters between any two points in the apparatus, for example, between any two of the listed locations.

In an embodiment, the present apparatus includes one or more reagent vessels, each of which can contain hydrogen peroxide or carboxylic acid(s). These vessels can be in fluid communication with a pretreatment column, with mixing of the reagents either before or in that column. The pretreatment column can be in fluid communication with the reaction catalyst (typically in a column). The resulting peroxycarboxylic acid emerges from the reaction catalyst and can be either used or stored, for example, in a day tank.

Reaction of the carboxylic acid with the peroxide occurs in the presence of the reaction catalyst as the reagents are contacted with (e.g., move through and/or around) the reaction catalyst at a controlled and predetermined flow rate. The size of the pretreatment column, the size of the bed of reaction catalyst, and the residence time in each of these are predetermined and controlled to provide the desired amount (often as much as possible) conversion of carboxylic acid to peroxycarboxylic acid. The size of the column, bed, or bag of reaction catalyst and the residence time in it are predetermined and controlled to provide the desired amount (often as much as possible) conversion of carboxylic acid to peroxycarboxylic acid. System parameters, such as the amount of reaction catalyst, size of the column, bed, or bag of reaction catalyst, and reagent flow rate, for the apparatus can be selected to provide sufficient residence time of the reaction mixture on the reaction catalyst for conversion into the desired peroxycarboxylic acid composition. The reaction catalyst can produce peroxycarboxylic acid at concentrations as high as, for example, about 35 wt-%, for example, about 5 (e.g., 5.3), about 10, about 15, about 20 (e.g., 19), about 25 wt-%, about 30 wt-%, or about 35 wt-%.

The apparatus can also include additional useful or desired systems such as fittings, valves, pumps, mixing chambers, water or additive supply connections, commonly employed for operation of systems including beds or columns of catalyst or cation exchanger.

The present apparatus can employ reagents that include only volatile components or only insignificant amounts of non-volatile components. Insignificant amounts of non-volatile compounds include an amount acceptable on a food or beverage container (e.g., an aseptic package) after washing and drying. For example, the present apparatus can employ reagents that do not include or are substantially free of stabilizer or chelating agent (e.g., HEDP). By way of further example, the present apparatus can employ reagents that are phosphate-free.

Accordingly, the present apparatus can produce peroxycarboxylic acid compositions that include only volatile components or only insignificant amounts of non-volatile components. For example, the present apparatus can produce peroxycarboxylic acid compositions that do not include or are substantially free of stabilizer or chelating agent (e.g., HEDP). By way of further example, the present apparatus can produce peroxycarboxylic acid compositions that are phosphate-free.

Pretreatment Column

In an embodiment, the apparatus includes one or more pretreatment columns each in fluid communication with a conduit from a single reagent vessel. The pretreatment column can be coupled directly to the bed, bag, or column of reaction catalyst. Alternatively, the pretreatment column can be in fluid communication with second pretreatment column that is also in fluid communication with a source of a second reagent. The pretreatment column can be in fluid communication with a conduit for the second reagent (pretreated or not) in which the reagents mix before entry into the second pretreatment column. The size of the pretreatment column and the residence time in the pretreatment column are predetermined and controlled to provide the desired amount of contaminant removal from the pretreated composition.

In an embodiment, the apparatus includes a plurality of (e.g., two) pretreatment columns coupled in parallel between a plurality of reagent vessels and the reaction catalyst. Reagent flow through conduits can be controlled by valve systems. Flow can be directed through a pretreatment column until that pretreatment column has received sufficient use or is in a condition that indicates it is no longer fit for use. During use of the first pretreatment column, the second pretreatment column can remain ready for use. The valve system can then direct flow through the second pretreatment column when the first is no longer to be used. The column that is not being used can be replaced, maintained, washed, or the like. For ease of replacement, the pretreatment column can be a cartridge that is quickly and easily removed from and placed into the apparatus. A pretreatment column can be washed with, for example, a dilute strong mineral acid, such as sulfuric acid.

Alternatively, the pretreatment column or system can be configured as a pretreatment bed or pretreatment bag. The pretreatment bed or bag can be employed in place of the pretreatment column in the embodiments described herein.

Use of the apparatus can continue while one of the pretreatment columns is being maintained or replaced. Changing columns can be done according to a predetermined schedule. Alternatively, the condition of the pretreatment column that is in use can be measured by the safety system, which can also control the valve system.

In an embodiment, the pretreatment column is a cartridge or segment that precedes the reaction catalyst and that can be within the column, bag, or bed that contains the reaction catalyst. Such a cartridge can be exchanged into and out of the column, bag, or bed of reaction catalyst. In an embodiment, the pretreatment column can be a portion of cation exchanger at the entry to or beginning of the column, bag, or bed of reaction catalyst. This portion is configured to be removed and replaced when, for example, the safety system so indicates or after a certain amount of use.

Reaction Catalyst

The reaction catalyst can be in one or more beds, bags, or columns. The beds, bags, or columns can be coupled in series, in parallel, or with some in series and some in parallel. In an embodiment, the apparatus includes four columns containing reaction catalyst and connected in series. In other embodiments, the apparatus includes up to about 10 columns of reaction catalyst, for example one to ten columns, for example, two, three, four, or five columns.

Reagent flow through beds, bags, or columns of reaction catalyst can be controlled by a valve system. Flow can be directed through a bed, bag, or column until that bed, bag, or column has received sufficient use or is in a condition that indicates it is no longer fit for use. During use of a first bed, bag, or column, a second bed, bag, or column can remain ready for use. The valve system can then direct flow through the second bed, bag, or column when the first is no longer to be used. During use of a first set of beds, bags, or columns, a second set of beds, bags, or columns can remain ready for use. The valve system can then direct flow through the second set of beds, bags, or columns when the first set is no longer to be used. The bed, bag, or column (or set thereof) that is not being used can be replaced, maintained, washed, or the like. Use of the apparatus can continue while one of the (sets of) beds, bags, or columns is being maintained or replaced. The condition of the bed, bag, or column that is in use can be measured by the safety system, which can also control the valve system.

Safety System

The apparatus can include a safety system that can measure one or more properties of the pretreatment column, of the reaction catalyst, or both. For example, the safety system can measure pressure (e.g., increased pressure), temperature (e.g., increased temperature), or both. An increase in temperature or pressure from a nominal value for a pretreatment column can indicate, for example, unwanted active metal ion catalyzed decomposition of hydrogen peroxide. For example, the safety system can measure a difference in temperature between two points in or around (e.g., before and after or before and in) the pretreatment column. An increase in the difference in temperature or difference in pressure from a nominal value for two points in or around a pretreatment column can indicate, for example, unwanted active metal ion catalyzed decomposition of hydrogen peroxide. The point or points at which temperature or pressure is measured can be selected to provide the desired sensitivity to contamination or decomposition. The safety system can include a manometric sensor for measurements of values or changes in values.

The safety system can measure pressure, temperature, difference in pressure, difference in temperature, or a combination thereof and provide a perceptible signal if one or more of these increases above a predetermined level. Pressure, temperature, difference in pressure, difference in temperature, or a combination thereof above a certain level can indicate danger from the reaction of peroxide with metals. The level of pressure, temperature, difference in pressure, difference in temperature, or a combination thereof at which safety system provides a perceptible signal can be selected to allow intervention to avoid undesirable or unsafe conditions.

The safety system, upon detecting pressure, temperature, difference in pressure, difference in temperature, or a combination thereof above the preselected level, can provide a perceptible signal that alerts the operator to interrupt operation of the apparatus by, for example, actuating a pressure release valve, stopping flow of one or more reagents, causing water to flow into the apparatus, causing carboxylic acid composition to flow into the apparatus, shutting down the apparatus, or a combination thereof. The safety system, upon detecting pressure, temperature, difference in pressure, difference in temperature, or a combination thereof above the preselected level, can provide a perceptible signal that alerts the operator to switch to another pretreatment column or bed or column of reaction catalyst.

The safety system can provide a signal to a controller (e.g., a controllable logic controller) and the controller can actuate a pressure release valve, stop flow of one or more reagents, cause water to flow into the apparatus, cause carboxylic acid composition to flow into the apparatus, shut down the apparatus, or a combination thereof. The safety system, upon detecting pressure, temperature, difference in pressure, difference in temperature, or a combination thereof above the preselected level, can provide a signal to a controller to switch to another pretreatment column or bed or column of reaction catalyst.

The safety system can measure conditions at an inlet or outlet of a pretreatment column, within that column (e.g., near the entrance of the column, in the interior of the column, or near the exit from the column), or in a conduit entering or leaving the pretreatment column. Another embodiment of the safety system can quantify the amount of metal that enters or has entered the pretreatment column or reaction catalyst.

In an embodiment, the safety system is configured to measure temperature at the entrance to the pretreatment column and in the first 25% of the pretreatment column. Although not limiting to the present invention, it is believed that measuring this difference can be desirable because contamination of the pretreatment column can occur in an exponential gradient and the reaction between the hydrogen peroxide and the contamination (e.g., metal ions, such as $Fe^{2+}$ or $Cu^{2+}$) on the column is exothermic.

In an embodiment, the safety system can include a processor and two condition sensors (e.g., temperature sensor, pressure sensor, metal sensor, or the like). The processor can, for example, perform calculations on input received from the condition sensors and provide a signal that can be received and/or perceived by an operator of the apparatus or one or more actuators. In an embodiment, the actuator can signal, activate, or operate a valve, pump, switch, or other system for actuating a pressure release valve, stopping flow of one or more reagents, causing water to flow into the apparatus, causing carboxylic acid composition to flow into the apparatus, shutting down the apparatus, or a combination thereof.

The safety system can be configured to measure conditions at an inlet or outlet of a column, bed, or bag of reaction catalyst, within that column, bed, or bag (e.g., near the entrance, in the interior, or near the exit), or in a conduit entering or leaving the reaction catalyst. In an embodiment, the safety system is configured to measure temperature at the entrance to the reaction catalyst and in the first 25% of the reaction catalyst.

Additional Systems

The apparatus can also include systems for storing, handling, diluting, and formulating the composition made by the apparatus. For example, the resulting peroxycarboxylic acid that emerges from the reaction catalyst can be either used or stored, for example, in a day tank. The storage system can be a vessel such as a day tank or another vessel suitable for containing a peroxycarboxylic acid composition between synthesis and use. Alternatively, a conduit from the apparatus can lead directly to a dilution apparatus or point of use.

The apparatus can include dilution and/or formulation systems for diluting and/or formulating the composition from the apparatus or the day tank. The apparatus can produce a concentrate, which can be diluted before use. The concentration of peroxycarboxylic acid in the use solution can be, for example, about 2 to about 5000 ppm or about 750 ppm to about 3600 ppm. Additional suitable use dilutions and compositions are described hereinbelow. The dilution apparatus can add and/or mix into the peroxycarboxylic acid a diluent or carrier, such as water, to achieve a diluted composition containing, for example, a desired use concentration of peroxycarboxylic acid. In an embodiment, the dilution system can include a pump that takes in both carboxylic acid composition and diluent and puts them out in one or more conduits in a desired proportion. The dilution system can provide the diluted composition directly to the site of use, to the day tank, or to a diluted composition storage system. In an embodiment in which the dilution system applies the diluted composition directly to the site of use, this system can include an applicator nozzle. The applicator nozzle can be configured to heat the composition while applying it.

In an embodiment, the apparatus and/or the diluting system can be configured to add another ingredient to the peroxycarboxylic acid composition. A variety of such ingredients are described hereinbelow. For example, the diluting system can add a diluent that contains an added ingredient. A formulating system can dispense a desired amount of an added ingredient into the composition or diluted composition. Such a system is useful for adding an ingredient that is not compatible with synthesis or storage of peroxycarboxylic acid, such as a quaternary ammonium chloride.

The storage system can include a storage monitor configured to measure the content of peroxycarboxylic acid, carboxylic acid, and/or hydrogen peroxide in the composition, for example, in a stored use composition. In an embodiment, the diluted composition storage system includes an replenishing system. The replenishing system can monitor the content of the use composition. If, for example, the concentration of peroxycarboxylic acid decreases below a predetermined level or the concentration of carboxylic acid increases above a predetermined level, the replenishing system can add more concentrated peroxycarboxylic acid composition to the use composition or empty the vessel of the spent use composition. The replenishing system can include, for example, flow meters and a sensor that detects the concentration of peroxycarboxylic acid.

The apparatus can also include a reagent flow control system. The reagent flow system can monitor the peroxycarboxylic acid composition after the reaction catalyst, for example, at an outlet from the last reaction catalyst column. This system can determine whether the composition includes the desired concentration of peroxycarboxylic acid (e.g., the equilibrium concentration). If the composition includes less than the desired concentration, the system can slow the flow rate of the reaction mixture through the reaction catalyst to a flow rate that results in the desired concentration. The system can calculate the change in flow rate employing factors including the temperature of the composition and the concentration of peroxycarboxylic acid. The desired concentration of peroxycarboxylic acid can be a lower limit and the desired concentration can be any achievable concentration above that lower limit.

In an embodiment, the present apparatus can include a middle vessel configured to receive one or more reagents after the reagent(s) passes through the pretreatment column. The middle vessel can be in fluid communication with the pretreatment column and the reaction catalyst. The middle vessel can be configured to receive pretreated reagent(s) and to contain them. The middle vessel can be simultaneously in fluid communication with a pretreatment column and reaction catalyst. In an embodiment, the middle vessel can be in fluid communication with a pretreatment column and with the reaction catalyst at different times or at overlapping times. In an embodiment, the middle vessel can in be in a first position for receiving reagent(s) from the pretreatment column and transported to a second position to provide reagents to the reaction catalyst.

In an embodiment, the present apparatus can include a purification system that removes non-volatile components from one of more of the reagents, e.g., one or more of carboxylic acid and peroxide. In an embodiment, the purification system is configured as a column, bag, or bed of anion exchanger in fluid communication with the source of hydrogen peroxide and the pretreatment column.

The present apparatus can be in fluid communication with an aseptic packaging system and configured to provide peroxycarboxylic acid composition to the aseptic packaging system. The peroxycarboxylic acid composition can be ready to use or can require dilution before use in the aseptic packaging system. In an embodiment, the present apparatus can provide ready to use peroxycarboxylic acid composition, for example, to a bottle rinse vessel and/or to a cap rinse vessel tank. In an embodiment, the present apparatus can supply a concentrate, which can be mixed with water or another diluent in or by the aseptic packaging system. Such a packaging system can include a water vessel or be coupled to a source of purified water. The aseptic packaging system can include a chamber in which bottles are rinsed and a chamber in which caps are contacted with the diluted or ready to use peroxycarboxylic acid composition. The aseptic packaging system can include a recycling system that recovers peroxycarboxylic acid composition that has been applied to bottle and/or cap and returns it to the appropriate vessel for reuse or that reapplies the composition to additional bottles and/or caps.

Embodiments of the Apparatus

In an embodiment, the present apparatus can include two or three reagent vessels, one containing hydrogen peroxide, one containing short chain carboxylic acid (e.g., acetic acid), and, optionally, a third vessel containing medium chain carboxylic acid (e.g., octanoic acid). The short chain carboxylic acid (e.g., acetic acid) vessel can be coupled by a conduit to a short chain carboxylic acid (e.g., acetic acid) pretreatment column, with mixing of reagents occurring after this column. The short chain carboxylic acid (e.g., acetic acid) pretreatment column can include a cation exchanger in acid form or in inert metal (e.g., $Na^+$ or $K^+$) form, which can remove positively charged contaminants, such as metal ion (e.g. non-inert metal ion, e.g., iron ($Fe^{2+}$ and/or $Fe^{3+}$) or copper ($Cu^{2+}$) ion), from the acetic acid. The inert metal cation can be selected to be only weakly bound by the cation exchanger. Pretreatment columns dedicated to the hydrogen peroxide and/or medium chain carboxylic acid are optional.

Embodiments for Producing a Peroxycarboxylic Acid

In an embodiment, only the short chain carboxylic acid (e.g., acetic acid) has a dedicated pretreatment column and medium chain carboxylic acid is not employed. In this embodiment, the conduits for short chain carboxylic acid (e.g., acetic acid) and for hydrogen peroxide join and these reagents mix before a main pretreatment column. The main pretreatment column can include a cation exchanger in acid form or in inert metal (e.g., $Na^+$ or $K^+$) form, which can remove positively charged contaminants, such as metal ion, from the mixture of hydrogen peroxide and carboxylic acid. The conduit of the mixture of acetic acid and hydrogen peroxide couples to the main pretreatment column and provides these mixed reagents to the column. This embodiment includes four columns of reaction catalyst. These four columns are in series and are coupled by a conduit to the main pretreatment column. At the other end, the four columns feed short chain peroxycarboxylic acid (e.g., peroxyacetic acid) into a conduit that leads to either a storage vessel or to a point of use for this composition.

This embodiment can also include a safety system. The safety system can include sensors that monitor temperature, for example, in the conduit after mixing of hydrogen peroxide and short chain carboxylic acid (e.g., acetic acid) and/or at the inlet to the main pretreatment column. The safety system can also include a sensor that monitors temperature within the main pretreatment column, e.g., within the first 25% of the pretreatment column. The safety system can provide a perceptible signal when temperature difference between the sensor before the main pretreatment column and in the sensor in the main pretreatment column increases above a predetermined level, for example, about 10° C. In this embodiment, the safety system, provides a perceptible signal to an operator and/or provides a perceptible signal to a controller. Upon receipt of the signal, the operator or controller stops flow of reagents into the main guard column and/or flushes the conduits and main guard column with water or short chain carboxylic acid (e.g., acetic acid).

This embodiment of the apparatus can also include additional useful or desired systems such as fittings, valves, pumps, mixing chambers, and water or additive supply connections useful or advantageous in this apparatus. This embodiment can also include one or more of the systems for storing, handling, diluting, and formulating the composition made by the apparatus that are described above.

Embodiments for Producing Mixed Peroxycarboxylic Acids

In an embodiment, the present apparatus can include three reagent vessels, one containing hydrogen peroxide, one containing short chain carboxylic acid (e.g., acetic acid), and, a third vessel containing a medium chain carboxylic acid, such as octanoic acid. The short chain carboxylic acid (e.g., acetic acid) vessel can be coupled by a conduit to an short chain carboxylic acid (e.g., acetic acid) pretreatment column, with mixing of reagents occurring after this column. The short chain carboxylic acid (e.g., acetic acid) pretreatment column can be and operate as described for the embodiment above. Pretreatment columns dedicated to the hydrogen peroxide and/or medium chain carboxylic acid (e.g., octanoic acid) are optional.

In this embodiment, the conduits for short chain carboxylic acid (e.g., acetic acid) and for hydrogen peroxide join and these reagents mix before a first main pretreatment column. The main pretreatment column can be and operate as described for the embodiment above. The conduit of the mixture of short chain carboxylic acid (e.g., acetic acid) and hydrogen peroxide couples to the first main pretreatment column and provides these mixed reagents to the column.

This embodiment includes (e.g., four) columns of reaction catalyst dedicated to producing short chain peroxycarboxylic acid (e.g., peroxyacetic acid). These columns are in series and are coupled by a conduit to the first main pretreatment column. At the other end, these columns feed short chain peroxycarboxylic acid (e.g., peroxyacetic acid) into a conduit.

This embodiment also includes conduits for medium chain carboxylic acid and hydrogen peroxide that join and mix these reagents before a second main pretreatment column. The second main pretreatment column can be and operate as described for the embodiment above. The conduit of mixed medium chain carboxylic acid and hydrogen peroxide couples to the second main pretreatment column and provides these mixed reagents to the column. This embodiment includes (e.g., four) columns of reaction catalyst dedicated to producing medium chain peroxycarboxylic acid. These columns are in series and are coupled by a conduit to the second main pretreatment column. At the other end, these columns feed medium chain peroxycarboxylic acid into a conduit.

The short chain peroxycarboxylic acid (e.g., peroxyacetic acid) conduit and the medium chain peroxycarboxylic acid (e.g., octanoic acid) conduit can send these peracids into a storage and/or mixing vessel to produce a mixed peroxycarboxylic acid composition. Alternatively, these conduits can join to produce a mixed peroxycarboxylic acid composition.

This embodiment can also include a safety system. The safety system can include sensors that monitor temperature before and in each pretreatment column and that responds to an increased temperature difference for either pretreatment column. This embodiment of the apparatus can also include additional useful or desired systems such as fittings, valves, pumps, mixing chambers, and water or additive supply connections useful or advantageous in this apparatus. This embodiment can also include one or more of the systems for storing, handling, diluting, and formulating the composition made by the apparatus that are described above.

Components of the Apparatus
Pretreatment Column

The pretreatment column can include any of a variety of cation exchangers, such as strong cation exchangers. Suitable cation exchangers for the pretreatment column include polystyrene sulfonic acid resins, such as those sold under the tradenames Dowex M31, Dowex DR-2030, Dowex Monosphere M-31, Dowex Monosphere DR-2030, Dowex Marathon 545C, Dowex 50W X8-H, Dowex 545C, Dowex G26, Amberlyst 15Wet, Amberlyst 15 Dry, Amberlyst 31 Wet, Amberlyst 131 Wet, Amberlyst CH10, Purolite C-100H, Purolite C-150H, Lewatit MonoPlus S 100 H, Lewatit MonoPlus SP 112 H, and the like. Additional cation exchangers suitable for the pretreatment column include sulfonated tetrafluoroethylene copolymers such as those sold under the tradenames Nafion NR50 (beads), Nafion SAC-13 (granules), and Nafion 117 (film), and the like. Other cation exchangers suitable for the pretreatment column include those sold under the trade names Dowex 545C, Dowex G26, which have high ionic capacity. In an embodiment, the pretreatment column includes an alkali metal (e.g., sodium) form of the ion exchanger.

Although not limiting to the present invention, it is believed that, all other things being equal, polystyrene sulfonic acid resins with minimal crosslinking (via divinylbenzene) show an improved selectivity for exchanging early alkali metal (e.g., sodium and potassium) ions for the problematic transition or heavy metal (e.g., iron and copper) ions.

A suitable pretreatment column can be dimensioned for sufficient flow and binding capacity to support the volume demanded of the apparatus. For example, a pretreatment column in an apparatus that employs 4 columns of reaction catalyst, each having a volume of about 10 L, can employ a pretreatment column having a volume of about 5 L. For example, a pretreatment column in an apparatus that produces about 11 (e.g., 10.7) liters per hour of peracid composition can employ a pretreatment column including about 4 (e.g., 3.9) L of resin. For example, a pretreatment column in an apparatus that produces about 20 (e.g., 21.3) liters per hour of peracid composition can employ a pretreatment column including about 8 (e.g., 7.8) mL of resin. For example, a pretreatment column in an apparatus that produces about 45 (e.g., 42.6) liters per hour of peracid composition can employ a pretreatment column including about 15 (e.g., about 15.5) L of resin.

A pretreatment column can be configured for advantageous ease of cleaning the resin or exchanging the column. For example, the pretreatment column can be in fluid communication with the inlet and outlet conduits with quick connect couplings. Suitable quick connect couplings include Parkers Indi-Lok (Stratoflex) or Slide-Lok coupling or Cole-Parmers, EW-31306-16 couplings, the materials of construction being preferably polypropylene, polyethylene or polyfluorocarbon. Quick connect couplings are also used for the acid backflush, inlets and outlets which can be operated by the controller or operated manually. The pretreatment column can be a cartridge that can be exchanged in and out of the apparatus. Suitable cartridges can be machined from Schedule 40 Polypropylene, or high density polyethylene tubing and are fitted with manometric and or temperature sensors which can be coupled to the controller.

The apparatus can be configured to accept only cartridges suitable for use in the apparatus. For example, the apparatus and/or cartridge can include a fitting, radio frequency identification circuit, or other electronic device (e.g., a logic chip or bar code and reader) to indicate to the apparatus that the cartridge is suitable for use in the apparatus. For example, the cartridge can include a programmable device that stores the number of times the cartridge has been rinsed. The cartridge and/or apparatus can indicate after a predetermined number of washes that the cartridge is no longer suitable for use. The indication can result in the cartridge being locked out of the apparatus. Similarly, the apparatus can be configured to lock out a cartridge that is not appropriate for use in the apparatus.

For example, a transponder programmed with an identifier can be positioned on the pretreatment column and/or reaction catalyst. This will allow identification of the pretreatment column and/or reaction catalyst as suitable for the present apparatus. For example, the transponder can be placed on or molded into the pretreatment column and/or reaction catalyst. A small injectable transponder ($1/16"\times1/2"$) would work best on a pretreatment column and/or reaction catalyst, in part because of its ease of placement. Also, while it would be possible to mold the transponder into the rack at the time the rack is manufactured, being able to retrofit existing racks may be desirable. In alternative embodiments, other sizes of transponders are acceptable.

The transponder can be placed in any suitable location on or in the pretreatment column and/or reaction catalyst. In an embodiment, a particular orientation of the pretreatment column and/or reaction catalyst can be enforced by off-setting the transponder on one side or end of the pretreatment column and/or reaction catalyst and off-setting the transponder antenna appropriately.

The transponder can be pre-programmed with unique identifying information, such as an identifier value indicating the type of pretreatment column and/or reaction catalyst being used. An example of a transponder that may be used is Destron/IDI Injectable Transponder Model TX1400L. The Injectable Transponder is a passive radio-frequency identification tag, designed to work in conjunction with a compatible radio-frequency ID reading system.

In an alternative embodiment, image identification could also be used, wherein each pretreatment column and/or reaction catalyst could be identified before it is received in the present apparatus visually. An example of visual identification would be where the machine operator could have a choice of several different icons on a computer screen which will match the pretreatment column and/or reaction catalyst placed in the apparatus.

Identification of the pretreatment column and/or reaction catalyst could be done, for example, by use of specifically designed pretreatment column and/or reaction catalyst; by use of optical recognition; by use of bar codes; by color of the pretreatment column and/or reaction catalyst; or by use of a proximity sensor.

An embodiment of the present apparatus includes a transceiver, which is able to detect the type of pretreatment column and/or reaction catalyst from the identifier, and communicate that identifying information to a processor. The transceiver generally includes a transponder antenna which can located on the outer edge of the apparatus adjacent to the pretreatment column and/or reaction catalyst and its transponder. The transponder antenna could also be located within the apparatus. The transceiver also includes a transponder interface, which is coupled to the processor in order for the identifying information to be received by the processor, and subsequently in order to be looked up in the storage device.

For the detector, a barcode scanner similar to the type used in a supermarket could also be utilized in an embodiment. An infrared scanner or proximity sensor could be used. Examples of scanners that may be used are Destron-Fearing Corporation's (of South St. Paul, Minn.) Pocket Reader and Pocket Reader EX Scanners. Corresponding bar codes are affixed to the rack for detection by the bar code scanner.

Reaction Catalyst

The reaction catalyst can include any of a variety of cation exchangers, such as strong cation exchangers. In an embodiment, the reaction catalyst is the protonated form of the cation exchanger. Suitable cation exchangers as the reaction catalyst include polystyrene sulfonic acid resins, such as those sold under the tradenames Dowex M31, Dowex DR-2030, Dowex Monosphere M-31, Dowex Monosphere DR-2030, Dowex Marathon 545C, Dowex 50W X8-H, Dowex 545C, Dowex G26, Amberlyst 15 Wet, Amberlyst 15 Dry, Amberlyst 31 Wet, Amberlyst 131 Wet, Amberlyst CH10, Purolite C-100H, Purolite C-150H, Lewatit MonoPlus S 100 H, Lewatit MonoPlus SP 112 H, and the like. Additional cation exchangers suitable as the reaction catalyst include sulfonated tetrafluoroethylene copolymers such as those sold under the tradenames Nafion NR50 (beads), Nafion SAC-13 (granules), and Nafion 117 (film), and the like. Other cation exchangers suitable as the reaction catalyst include those sold under the trade names Dowex 545C, Dowex G26, which have high ionic capacity.

Additional suitable reaction catalysts include an inorganic compound that is or includes an insoluble strong acid, in certain embodiments, with a high surface area/weight ratio. Such inorganic catalysts include those sold under generic names such as "Sulfated Zirconia", "Silica Stabilized Tetragonal Zirconia" and "Tungstated Zirconia" (from Saint-Gobain Norpro). Suitable inorganic catalysts also include zirconia oxides sold as generic "$ZrO_2$" (MEI Chemicals). A zirconia oxide can be treated with sulfuric acid followed by calcination at ~700 deg C. to produce a "sulfated Zirconia."

Other suitable inorganic catalysts include sulfated silicas or silicon oxides, sulfated or acidified zeolites, sulfated or acidified aluminum oxides, and phosphonic acid derivatized silicon oxides (e.g., those sold under the tradename "Si—$POH_2$" and an alkylphosphonic acid modified silica from Phosphononics Ltd.)

A suitable column, bag, or bed of reaction catalyst can be dimensioned for sufficient flow and catalyst capacity to support the volumes demanded of the apparatus. For example, a column, bag, or bed of reaction catalyst in an apparatus that produces about 40 (e.g., 41) liters per hour of peracid composition can employ four columns of reaction catalyst each with volume of about 30 (e.g., 31) L and being 1 meter in length and 20 cm in diameter. A bed, bag, or column of reaction catalyst can be dimensioned in any suitable dimension for achieving the desired flow. Suitable dimensions include about 0.1 (e.g., 0.13) to about 15 (e.g., 13) meters in, for example, length by about 10 to about 100 cm in, for example, diameter. Suitable columns include those dimensioned about 15 (e.g., 13) meters in length by about 10 cm in diameter. Suitable columns include those dimensioned about 0.5 (e.g., 0.4) meters in length by about 20 cm in diameter. Suitable columns include those dimensioned about 0.15 (e.g., 0.13) meters in length by about 100 cm in diameter. A column can be in any of a variety of configurations. For example, a column can be a normal cylindrical tube or a coiled tube. Suitable coiled tubes include a tube about 60 (e.g., 62) meters long by about 5 cm in diameter in a coil about 1 meter in diameter with about 20 turns. The reaction catalyst can be configured to provide about 30 to about 300 minutes of contact time of the catalyst and the reaction mixture.

A column, bag, or bed of reaction catalyst can be configured for advantageous ease of cleaning, regenerating, or backflushing the bed, bag, or column. Advantageous features of the column, bag, or bed of reaction catalyst include a plurality of ports and valves between segments of catalyst that allow for selective backflushing of isolated segments of the overall catalytic bed as well as venting of the accumulated gases to facilitate pumping and circulating of cleaning or backflushing agents.

Reagents

Suitable reagents include hydrogen peroxide at about 5 to about 70 wt-%, about 5 to about 50 wt-%, or about 35 to about 50 wt-% in water; e.g., hydrogen peroxide at about 35 wt-%, about 45 wt-%, about 50 wt-%, or about 70 wt-% in water. Suitable reagents include acetic acid at about 5 to about 100 wt-% (remainder water) or at about 80 to about 98 wt-%; for example, acetic acid at about 80 wt-%, about 98 wt-%, or about 100 wt-%. Glacial acetic acid is a suitable form of acetic acid. Suitable reagents include octanoic acid at about 1 to about 10 wt-% in glacial acetic acid.

Additional suitable hydrogen peroxide reagents include urea-hydrogen peroxide or any of a variety of other non-ionic hydrogen peroxide complexes. Additional suitable oxidizing reagents include caros acid, acidified sodium persulfate, or other peroxy species which equilibrate to form hydrogen peroxide in water.

Additional suitable acetic acid reagents include acetic anhydride, acetyl chloride, polyvinyl acetate, and mono, di and triacetyl glycerine. Additional suitable octanoic acid reagents include about 1 to about 10 wt-% octanoic acid in propylene glycol; about 1 to about 10 wt-% octanoic acid in water with a hydrotrope coupling agent, such as sodium octane sulfonate, or acidic forms of xylene sulfonate, toluene sulfonate, dioctyl sulfosuccinate, or other alkyl or aryl sulfonates. Other suitable hydrotropes include fatty alcohol ethoxylate phosphate esters, such as Ecolab's PE 362, Emphos PS-236 or Gafac RA-600. Additional suitable carboxylic acid reagents include $C_1$ and $C_{20}$ alkanoic acids; polyprotic acids including glycolic, succinic, glutaric, adipic, citric, malic, or lactic acid; alpha and omega dicarboxylic acids such as succinic, adipic, pimelic, suberic, azelaic, or sebacic acid. Additional suitable peracid precursors include alcohol ethoxylate carboxylates and amido or imidocarboxylic acids.

The reagent compositions employed in the present apparatus need not include, and in embodiments, lack or are substantially free of stabilizer or chelating agent (e.g., HEDP). The reagent compositions employed in the present apparatus can include only volatile compounds. The reagent compositions including only volatile compounds can be phosphate-free.

In certain embodiments, the composition applied to the reaction catalyst includes about 55 (e.g., 56.5) wt-% carboxylic acid and about 30 (e.g., 30.5) wt-% hydrogen peroxide; about 45 (e.g., 43.6) wt-% carboxylic acid and about 20 (e.g., 20.5) wt-% hydrogen peroxide; about 20 wt-% carboxylic acid and about 30 (e.g., 28) wt-% hydrogen peroxide; about 80 (e.g., 78) wt-% carboxylic acid and about 10 (e.g., 7.7) wt-% hydrogen peroxide; or about 5 wt-% carboxylic acid and about 5 wt-% hydrogen peroxide.

In certain embodiments, the composition applied to the reaction catalyst includes about 55 (e.g., 56.5) wt-% short chain carboxylic acid and about 30 (e.g., 30.5) wt-% hydrogen peroxide; about 45 (e.g., 43.6) wt-% short chain carboxylic acid and about 20 (e.g., 20.5) wt-% hydrogen peroxide; about 20 wt-% short chain carboxylic acid and about 30 (e.g., 28) wt-% hydrogen peroxide; about 80 (e.g., 78) wt-% short chain carboxylic acid and about 10 (e.g., 7.7) wt-% hydrogen peroxide; or about 5 wt-% short chain carboxylic acid and about 5 wt-% hydrogen peroxide.

In certain embodiments, the composition applied to the reaction catalyst includes about 20 wt-% medium chain carboxylic acid and about 30 wt-% hydrogen peroxide; about 10 wt-% medium chain carboxylic acid and about 20 wt-% hydrogen peroxide; about 5 wt-% medium chain carboxylic acid and about 20 wt-% hydrogen peroxide; or about 3 wt-% medium chain carboxylic acid and about 20 to about 25 (e.g., 22.5) wt-% hydrogen peroxide.

In certain embodiments, the composition applied to the reaction catalyst includes about 50 (e.g., 48) wt-% short chain carboxylic acid, about 20 wt-% medium chain carboxylic acid, and about 10 wt-% hydrogen peroxide; about 55 (e.g., 56) wt-% short chain carboxylic acid, about 10 (e.g., 8) wt-% medium chain carboxylic acid, and about 12 wt-% hydrogen peroxide; about 60 wt-% short chain carboxylic acid, about 2 wt-% medium chain carboxylic acid, and about 15 (e.g., 13) wt-% hydrogen peroxide; or about 45 (e.g., 44) wt-% short chain carboxylic acid, about 1 wt-% medium chain carboxylic acid, and about 20 (e.g., 21) wt-% hydrogen peroxide.

In certain embodiments, the present composition includes peroxycarboxylic acid and hydrogen peroxide in a ratio of about 0.3:1 to about 7:1, about 1:1 to about 3:1, or about 2:1 to about 3:1. Certain embodiments include peroxycarboxylic acid and hydrogen peroxide in a ratio of about 2:1 to about 3:1, for example, 2.4:1; peroxycarboxylic acid and hydrogen peroxide in a ratio of about 1:1 to about 2:1, for example 1.4:1; peroxycarboxylic acid and hydrogen peroxide in a ratio of about 0.3:1 to about 1:1, for example 0.4:1; or peroxycarboxylic acid and hydrogen peroxide in a ratio of about 7:1, for example 7.1:1.

In certain embodiments, the reagents used in the present apparatus can include impurities, such as metal ions, at levels up to 100 ppm, up to 10 ppm, up to 1 ppm, or up to 0.1 ppm. Such impurities can include Fe, Cu, Mn, Ni, Ti, Co or any of the transition metal ions.

Illustrated Embodiments

FIG. 1 illustrates an embodiment of the present apparatus in the form of peroxycarboxylic acid generator 20. In FIG. 1, one or more reagent supply vessels 21, for example, first reagent supply vessel 22 containing hydrogen peroxide and second reagent supply vessel 24 containing one or more carboxylic acids are coupled by first and second lines 26 and 28, respectively, to guard column 30. Hydrogen peroxide and carboxylic acid are delivered individually from first and second reagent supply vessels 22 and 24 via first and second lines 26 and 28, respectively, into a mix line 29 leading into guard column 30. In mix line 29 the reagents combine into a reaction mixture, although combining may also occur in guard column 30. Guard column 30 contains a cation exchanger (not shown) that removes metal ions from the reaction mixture. The reaction mixture then proceeds to one or more reactor columns 34 via third line 32.

Reactor column 34 is packed with strong acid catalyst (not shown). Inside reactor column 34, the reaction mixture of hydrogen peroxide and carboxylic acid react as they move through the strong acid catalyst at a predetermined, controlled flow rate. System parameters, such as column size and reagent flow rate, for the peroxycarboxylic acid generator 20 are selected and/or controlled to provide sufficient residence time of the reaction mixture on the strong acid catalyst for conversion into the desired peroxycarboxylic acid composition. Generator design and process control are described in more detail herein below. The peroxycarboxylic acid composition is discharged from a reaction column 34 via third line 36, for example, into a holding tank 38.

In an embodiment, a peroxycarboxylic acid generator 20 can also include one or more additional structural components, such as fittings, valves, pumps, mixing chambers, water or additive supply connections, commonly employed for operation of systems including packed columns. For example, flow from each reagent supply vessel can be individually controlled by providing a valve and a pump proximal to each reagent supply vessel.

Additional representative configurations for peroxycarboxylic acid generators 20 of the present invention are provided below. Aspects of the various configurations shown below may be combined or separated to present still further configurations of peroxycarboxylic acid generators. As in FIG. 1, basic components such as control valves, fittings and pumps which may be present are omitted from the schematic representation for clarity.

In an embodiment, peroxycarboxylic acid generator 20 includes one or more guard columns 30 in the form of a reagent guard column 40, which is positioned to receive material from one of first reagent supply vessel 22 or second reagent supply vessel 24. The output from reagent guard column 40 can go directly to a reactor column 34. The reagent guard column 40 can be positioned in the fluid flow between the first reagent supply vessel 22 or second reagent supply vessel 24 and the reactor column 34.

Figure 2:
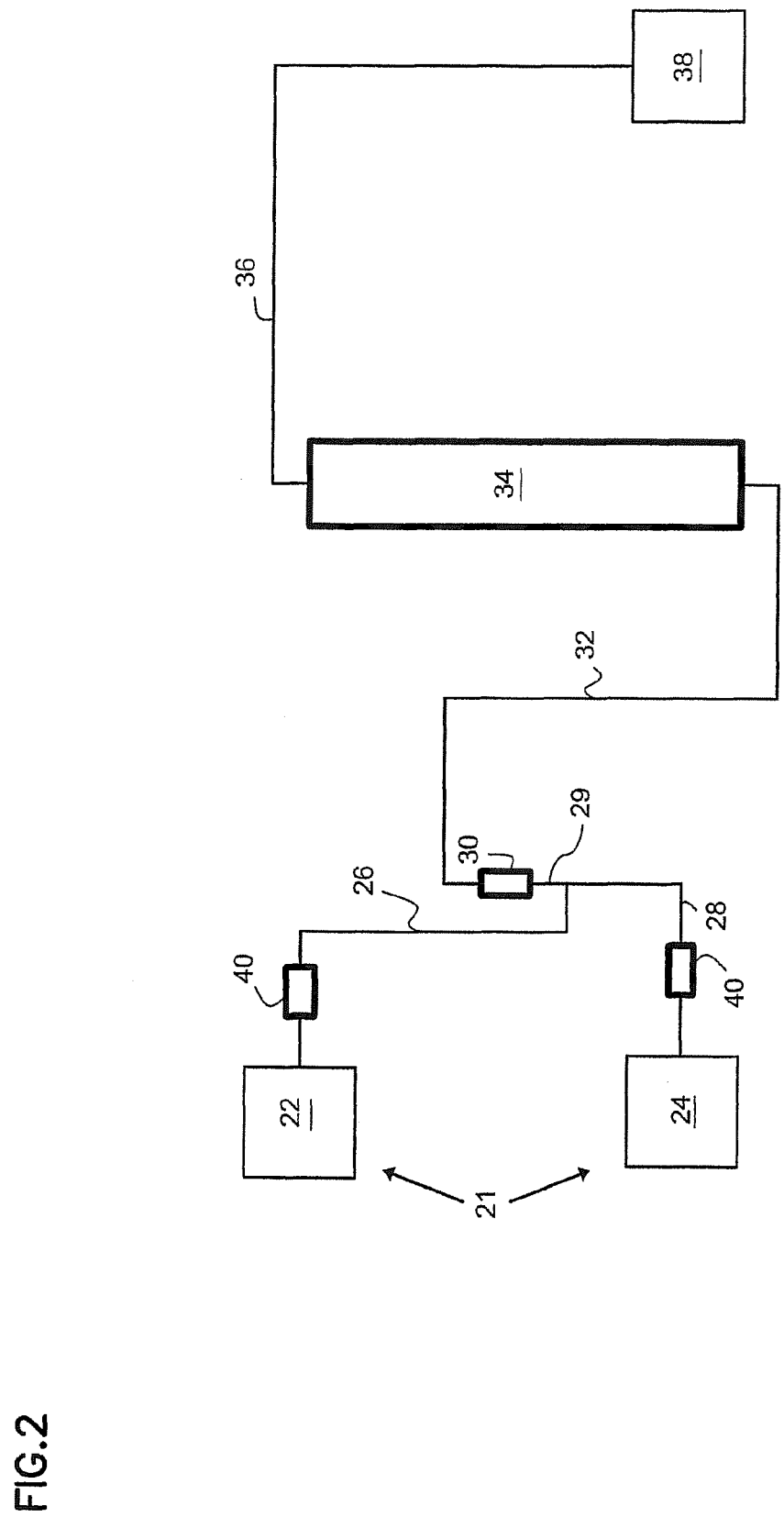

FIG. 2 illustrates an embodiment of the present peroxycarboxylic acid generator 20 including two reagent guard columns 40. In the embodiment shown in FIG. 2, a reagent guard column 40 is positioned in first line 26 connecting the hydrogen peroxide supply vessel 22 with the guard column 30 and another reagent guard column 40 is placed in second line 28 connecting the carboxylic acid supply vessel 24 with the guard column 30. Other embodiments can include only one (either one) of these reagent guard columns 40 and/or can omit the guard column 30. Reagent guard column 40 can be configured as a cartridge that can be readily removed and replaced in the peroxycarboxylic acid generator 20. The other components in FIG. 2 are as described above for FIG. 1.

Figure 3:
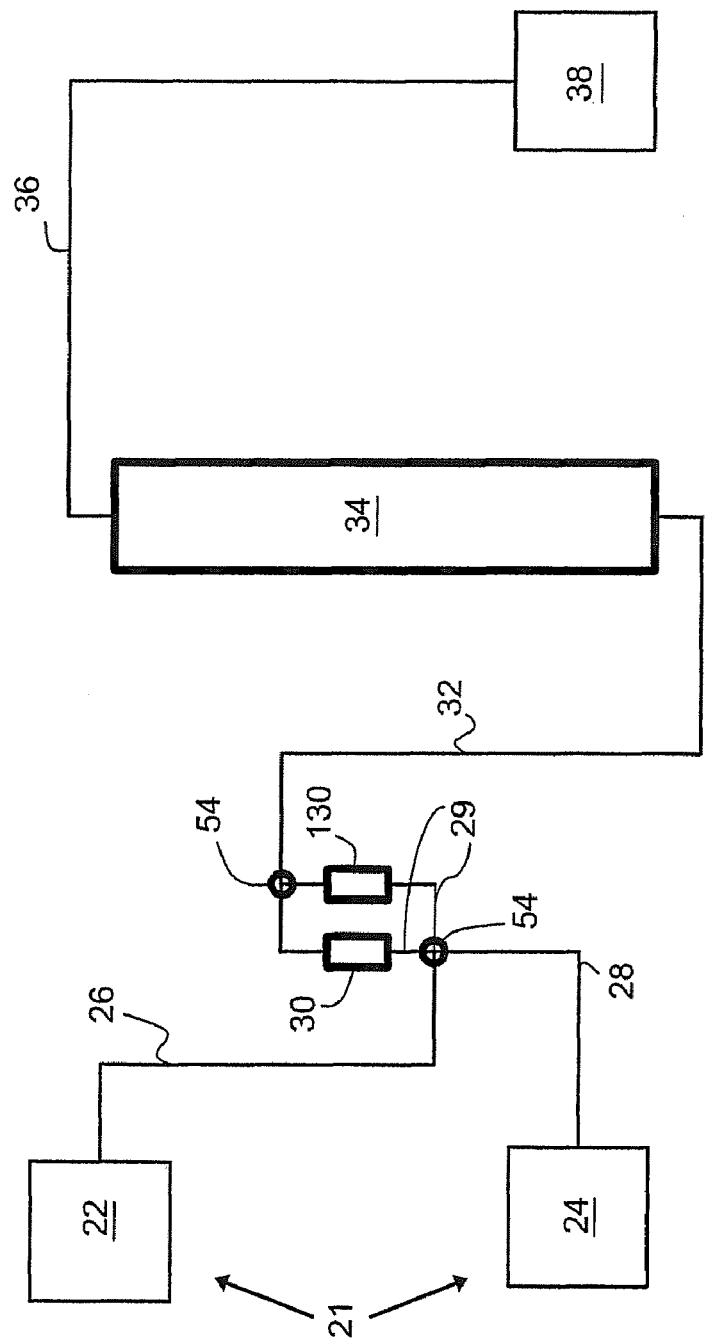

In another embodiment, peroxycarboxylic acid generator 20 includes a plurality of guard columns 30. FIG. 3 schematically illustrates an embodiment including two guard columns 30, the second in the form of second guard column 130. As illustrated, guard column 30 and second guard column 130 are positioned in parallel between the first and second reagent supply vessels 22 and 24 and reactor column 34. Reagent flow through first and second lines 26 and 28 into one or both of guard column 30 and second guard column 130 under the control of valves 54. With valves 54 directing flow through guard column 30, that column becomes full of contaminants, but second guard column 130 remains ready for use. When guard column 30 is no longer suitable for use, valves 54 can be set to direct flow through second guard column 130. The column that is not receiving flow can be washed, maintained, or replaced. In this fashion, operation of this embodiment of peroxycarboxylic acid generator 20 can continue while either first or second guard column 30 or 130 is being maintained or replaced. The condition of first and/or second guard column 30 or 130 can be determined by the measuring device (below), which can also control the setting of valves 54.

Figure 4:
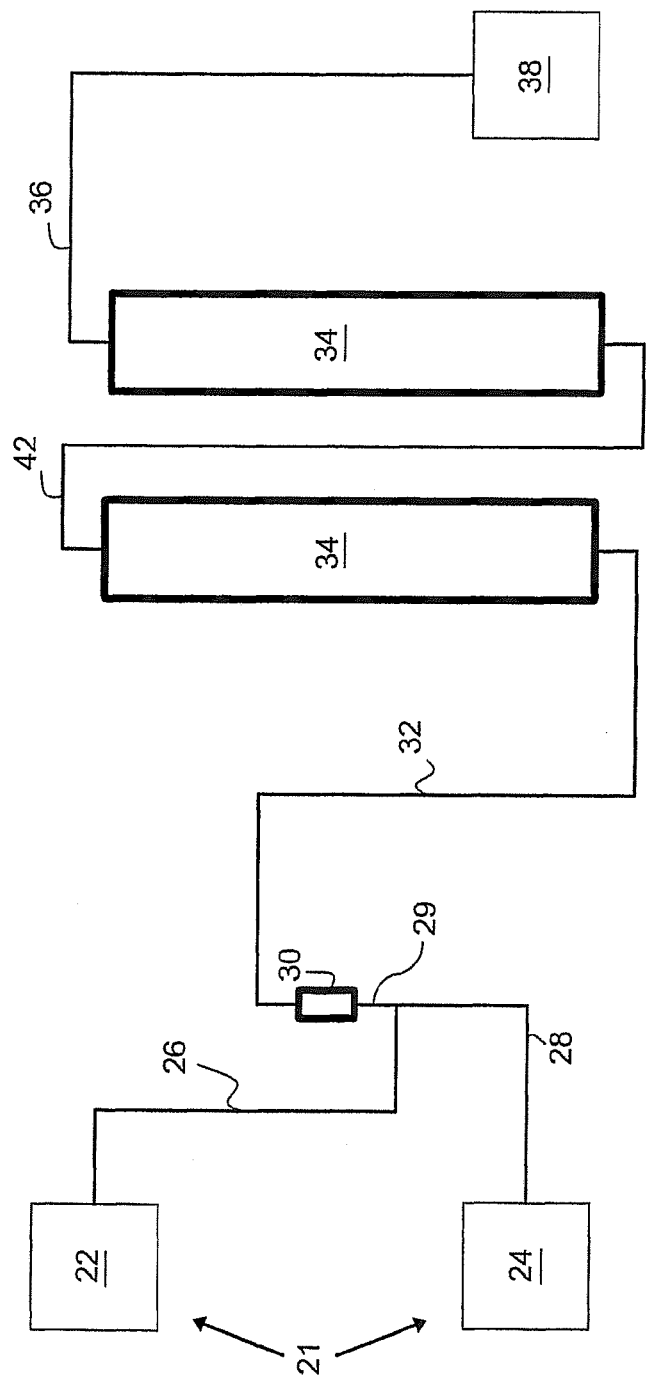

In another embodiment, peroxycarboxylic acid generator 20 includes a plurality of reactor columns 34. A plurality of reactor columns can be connected either in series, parallel, or both. FIG. 4 illustrates an embodiment including two reactor columns 34 connected in series. Fifth line 42 couples the two reactor columns. In various embodiments, the peroxycarboxylic acid generator 20 can include up to about ten reactor columns 34, for example one to ten reactor columns 34, for example, two, three, four, or five reactor columns 34, for example 4 reactor columns 34 coupled in series.

Figure 5:
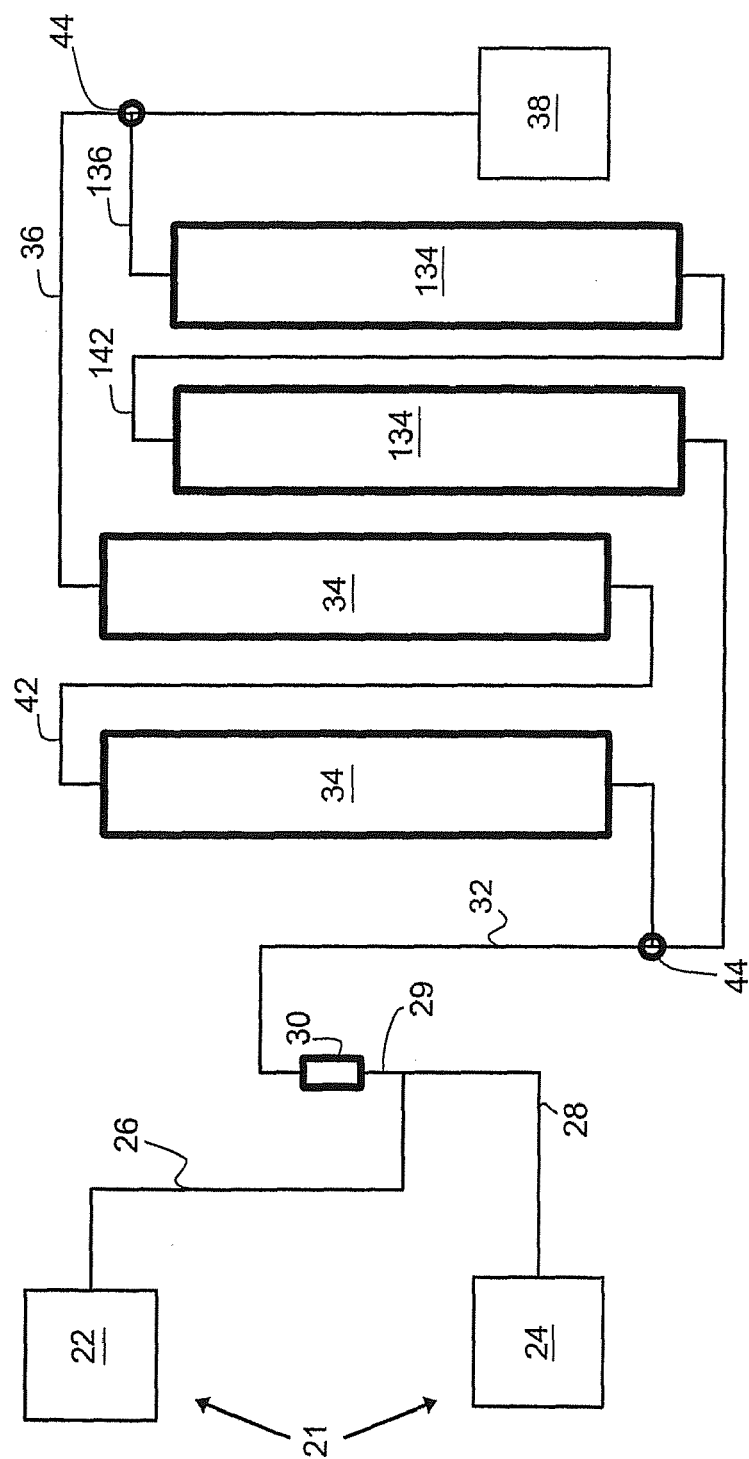

In an embodiment, the present apparatus includes a plurality of reactor columns 34 connected in parallel. Such an embodiment can include a plurality of reactor columns 34 coupled in series and also a plurality of reactor columns 34 coupled in parallel. FIG. 5 schematically illustrates such a system. In this illustration, the reaction mixture flows from guard column 30 to a first pair of reactor columns 34 in series that are coupled by fifth line 42. The guard column 30 is also coupled to a second pair of reactor columns 134 in series that are coupled by line 142. The first pair of reactor columns 34 and second pair of reactor columns 134 are connected in parallel. The reaction mixture flows from the first pair of reactor columns 34 to holding tank 38 through third line 36. The reaction mixture flows from the second pair of reactor columns to holding tank 38 through sixth line 136. Reactor valves 44 can direct the flow of reaction mixture through either first pair of reactor columns 34 or the second pair of reactor columns 134.

With the reactor valves 44 set to direct flow through first pair of reactor columns 34, those columns are subject to wear and can be consumed or fail, but the second pair of reactor columns 134 remains ready for use. When the first pair of reactor columns 34 is no longer suitable for use, reactor valves 44 can be set to direct flow through the second pair of reactor columns 134. The pair of columns that is not receiving flow can be washed, maintained, or replaced. In this fashion, operation of this embodiment of peroxycarboxylic acid generator 20 can continue while either first or second pair of reactor columns 34 or 134 is being maintained or replaced. The condition of first and/or second reactor columns 34 or 134 can be determined by the measuring device (below), which can also control the setting of reactor valves 44.

Monitoring Device

In an embodiment, peroxycarboxylic acid generator 20 can include apparatus for measuring one or more properties of the cation exchanger, reagents on the cation exchanger, the cation exchanger column assembly as a whole, the catalyst, the reagents on the catalyst, or the catalyst column assembly as a whole. For example, such a device can monitor pressure (e.g., increased pressure), temperature (e.g., increased temperature), or both. An increase in temperature or pressure from a nominal value can indicate unwanted active metal ion catalyzed decomposition of hydrogen peroxide.

For example, the monitoring device 46 can measure a difference in temperature between two points in or around (e.g., before and after or before and in) the guard column 30. An increase in the difference in temperature or difference in pressure from a nominal value for two points in or around a guard column 30 can indicate, for example, unwanted active metal ion catalyzed decomposition of hydrogen peroxide. The point or points at which temperature or pressure is measured can be selected to provide the desired sensitivity to contamination or decomposition.

Figure 6:
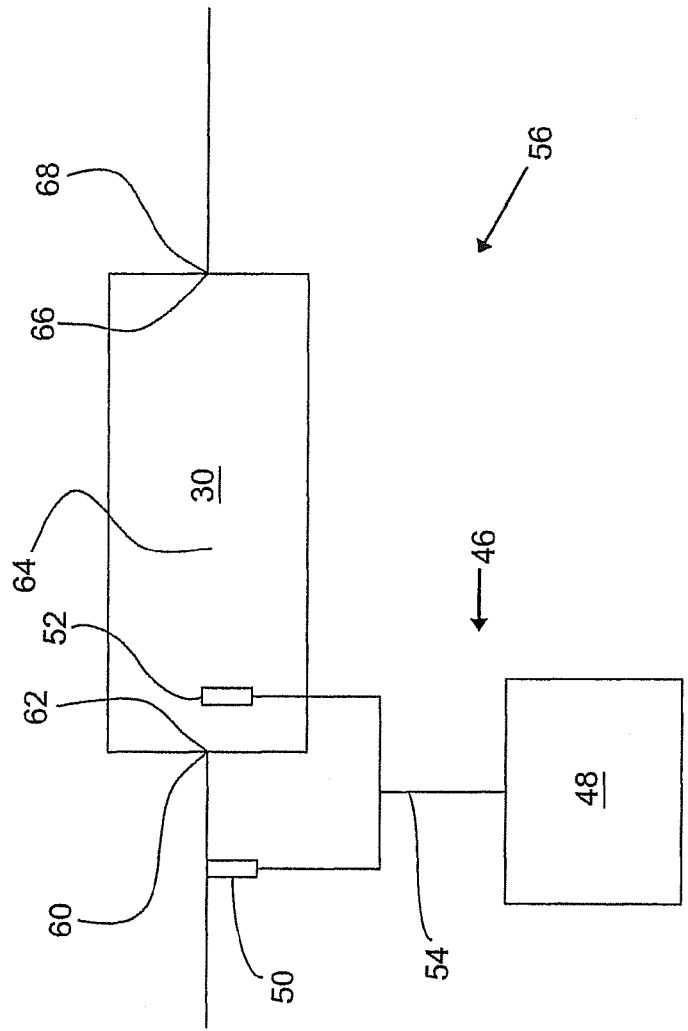
FIG. 6 schematically represents embodiments of the safety system and pretreatment column.

FIG. 6 illustrates an embodiment of guard column 30 and monitoring device 46, which is an embodiment of the safety system. Monitoring device 46 includes controller 48 and first and second sensors 50 and 52, respectively, and lead 54. Lead 54 couples first and second sensors 50 and 52 to controller 48. In the illustrated embodiment, first sensor 50 monitors the condition (e.g., temperature or pressure) of the reaction mixture in mixing line 29 and second sensor 52 monitors the condition within guard column 30. In an embodiment, second sensor can be positioned into guard column 30 about 10% to about 25% of the distance along the axis of guard column 30. This same configuration can be employed with reagent guard column 40.

Monitoring device 46 can measure a difference in conditions (e.g., temperature or pressure) between first sensor 50 and second sensor 52. First sensor can be positioned before guard column 30 (or reagent guard column 40) in, for example, first line 26, second line 28, or mixing line 29. Second sensor 52 can be positioned at the entrance of, in, or after guard column 30 (or reagent guard column 40). For example, second sensor 52 can be positioned at the inlet 60 to guard column 30, within 62 guard column 30 but before the cation exchanger, within 64 the cation exchanger of guard column 30 (near the entrance of the column, in the interior of the column, or near the exit from the column), within guard column 30 between the cation exchanger and the exit 66 from the guard column 30, or at the outlet 68 from the guard column 30. The second sensor can be in the same positions in reagent guard column 40. A difference or an increase in the difference in temperature or pressure from a nominal value between first sensor 50 and second sensor 52 can indicate, for example, unwanted active metal ion catalyzed decomposition of hydrogen peroxide.

Figure 7:
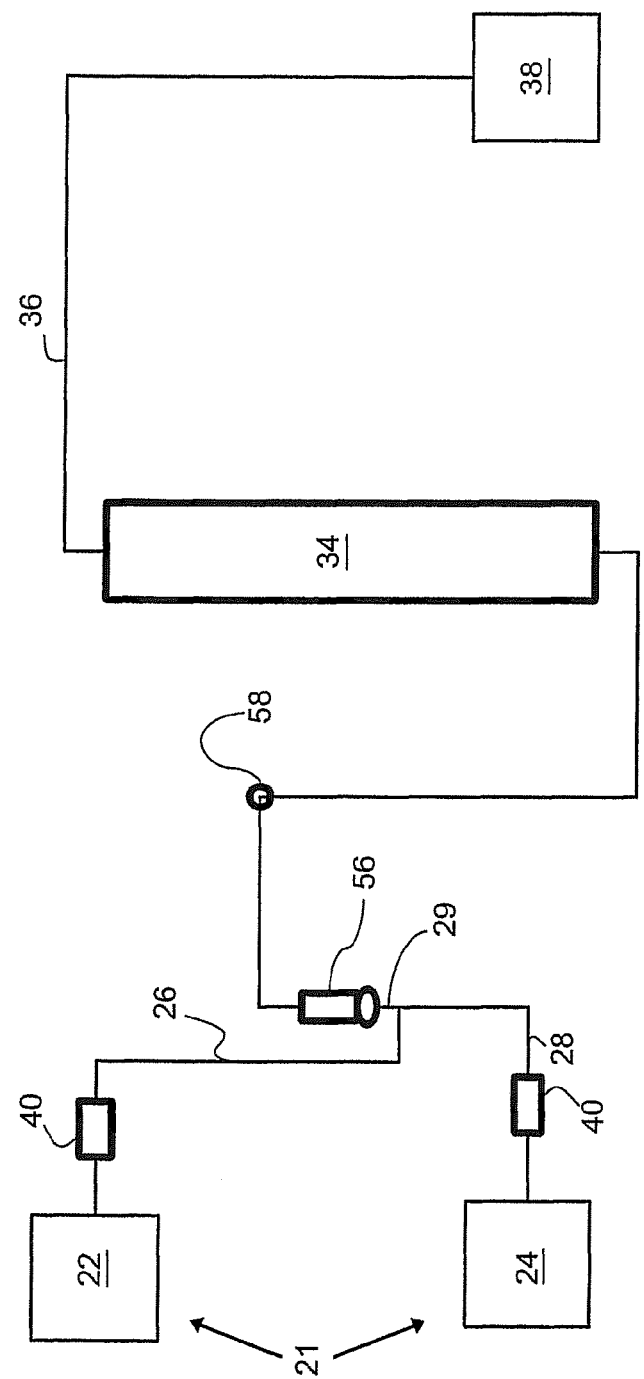
FIGS. 7-10 schematically represent embodiments of apparatus that generates peroxycarboxylic acid including embodiments of pretreatment column, reaction catalyst, and safety system.

The device illustrated in FIG. 6 is monitored guard column 56. Any of the embodiments illustrated in FIGS. 1-5 can employ monitored guard column 56 in place of guard column 30 or reagent guard column 40. For example, FIG. 7 schematically illustrates the embodiment of FIG. 2 modified to include monitored guard column 56 in place of guard column 30. In an embodiment, one or more of the reagent guard columns 40 can be monitored guard column 56. For a reagent guard column receiving carboxylic acid, the sensors can measure metal ion.

Upon measuring a difference in temperature or pressure above a preselected level, monitoring device 46 can provide a detectable signal that alerts the operator to interrupt operation of the apparatus. For example, the operator can actuate a pressure release valve 58, stop flow of one or more reagents, cause water to flow into the guard column 30 and/or reactor columns 34, cause carboxylic acid to flow into the guard column 30 and/or reactor columns 34, shut down the peroxycarboxylic acid generator 20, or a combination thereof. In an embodiment, the monitoring device 46 can provide a signal to the controller 48, which can be a controllable logic controller, and the controller 48 can actuate a pressure release valve 58, stop flow of one or more reagents, cause water to flow into the guard column 30 and/or reactor columns 34, cause carboxylic acid to flow into the guard column 30 and/or reactor columns 34, shut down the peroxycarboxylic acid generator 20, or a combination thereof.

Figure 8:
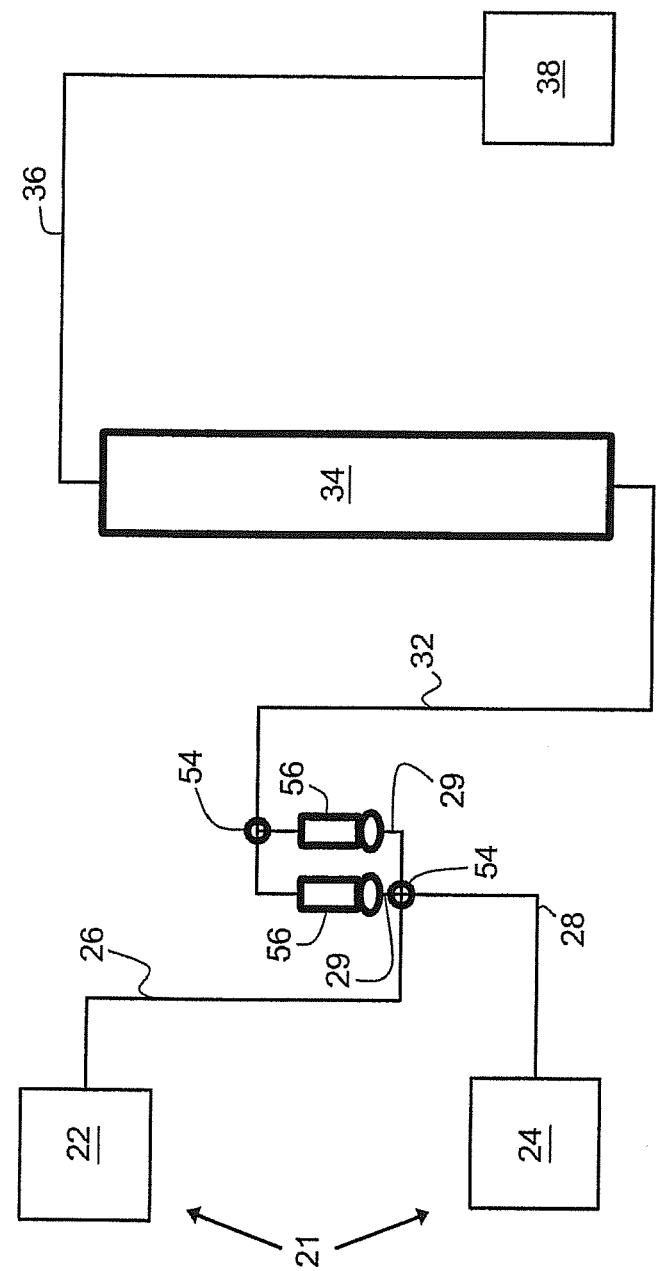

Upon measuring a difference in temperature or pressure above a preselected level, monitoring device 46 can provide a detectable signal that alerts the operator or that signals the controller 48 to switch to another guard column. For example, FIG. 8 schematically illustrates the embodiment of FIG. 3 modified to include first and second monitored guard columns 56 and 156 in place of first and second guard columns 30 and 130. In an embodiment, the operator can actuate valves 54 to send the reagent flow through a second monitored guard column 156. In an embodiment, the monitoring device 46 can provide a signal to a controller 48 (e.g., a controllable logic controller) and the controller 48 can actuate valves 54 to send the reagent flow through second monitored guard column 156.

Another embodiment of the measuring device can quantify the amount of metal that enters or has entered the column. For example, metal monitoring device 68 can be positioned at any of the positions described for monitoring device 46 and can provide the detectable signal when the amount of metal in the flow through the system exceeds a predetermined level. Alternatively, the metal monitoring device 68 can provide the detectable signal when a predetermined amount of metal has passed the position of the device. The detectable signal can be directed to an operator or controller for the purposes and responses described above.

Figure 9:
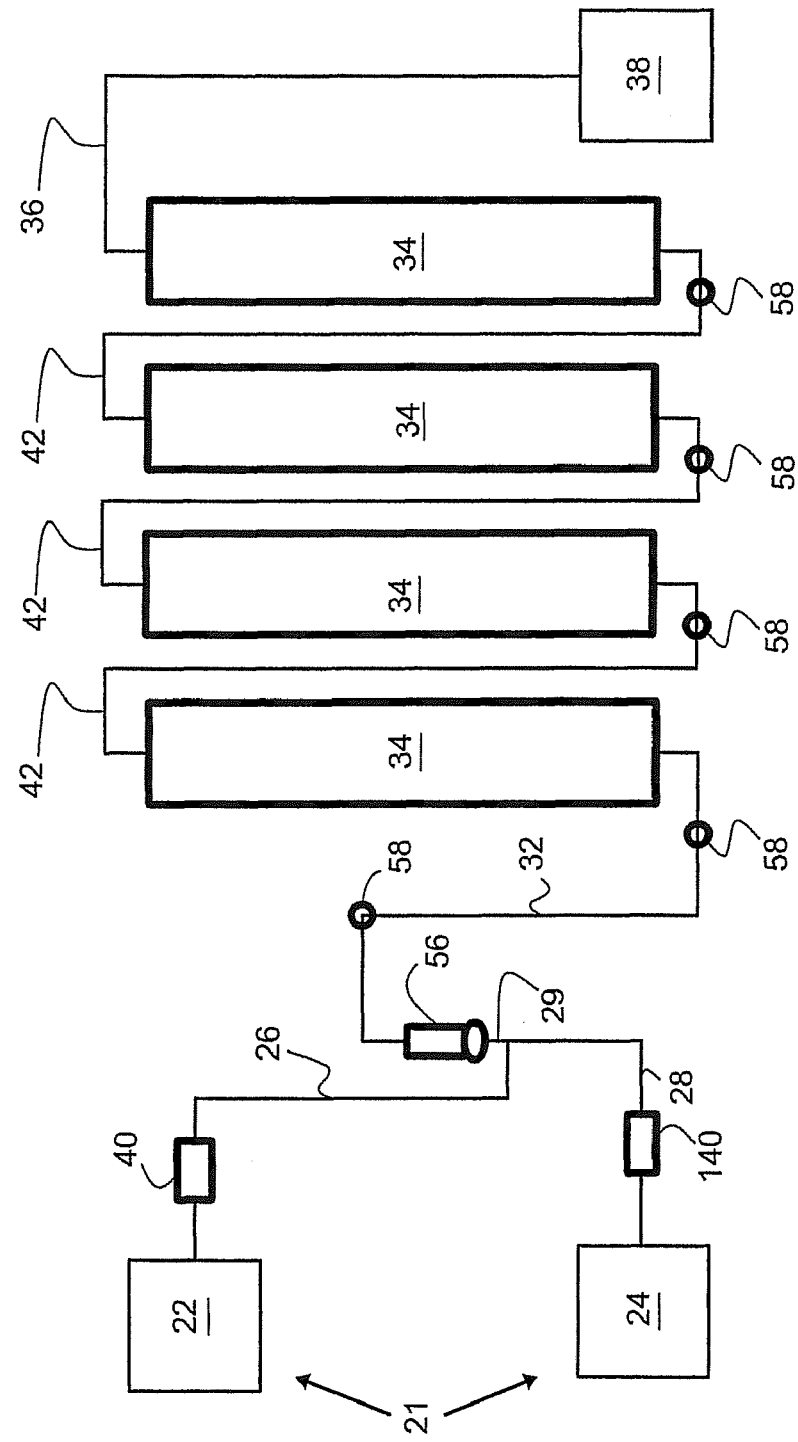

FIG. 9 schematically illustrates an embodiment of peroxycarboxylic acid generator 20 including first and second reagent vessels 22 and 24. In this embodiment, first reagent vessel 22 can contain a short chain carboxylic acid, such acetic acid (e.g., 98% acetic acid). Second reagent vessel 24 can contain oxidizing agent, such as hydrogen peroxide (e.g., 35-45% hydrogen peroxide). This embodiment includes one reagent guard column 40, optional second reagent guard column 140, monitored guard column 56, four reactor columns 34 connected in series, and five pressure release valves 58. The monitored guard column 56 can be of the configuration shown in FIG. 6 (e.g., with sensors before the guard column 30 and in the cation exchanger). The reagent guard column 40 can include a cation exchanger in acid form or in inert metal (e.g., $Na^+$ or $K^+$) form.

Figure 10:
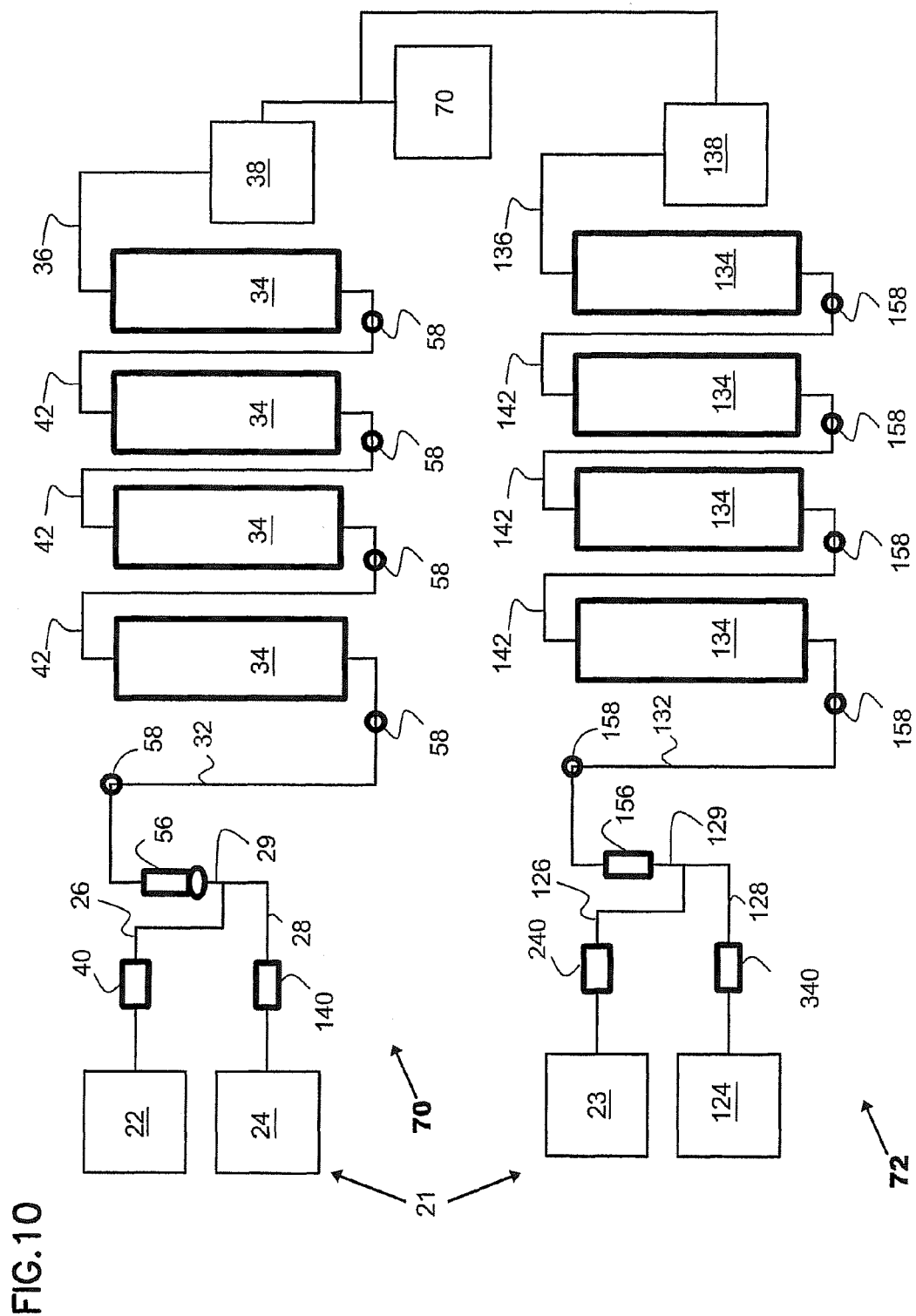

FIG. 10 schematically illustrates an embodiment of peroxycarboxylic acid generator 20 including first peracid generator 70 and second peracid generator 72. First peracid generator 70 is configured schematically illustrated in FIG. 9 and described above.

Second peracid generator 72 in FIG. 10 has components generally configured according to FIG. 9 and as described above. Second peracid generator 72 is, however, configured for producing medium chain peroxycarboxylic acid. In this embodiment, third reagent vessel 23 is configured to contain and supply a medium chain carboxylic acid, such as octanoic acid (e.g., 5 wt-% octanoic acid in propylene glycol). Second reagent vessel 124 is configured to contain and supply oxidizing agent, such as hydrogen peroxide (e.g., 35-45% hydrogen peroxide). This embodiment includes one reagent guard column 240, optional second reagent guard column 340, second monitored guard column 156, four reactor columns 134 connected in series, and five pressure release valves 158.

The second monitored guard column 156 can be of the configuration shown in FIG. 6 (e.g., with sensors before the guard column 30 and in the cation exchanger). The reagent guard column 240 can include a cation exchanger in acid form or in inert metal (e.g., $Na^+$ or $K^+$) form.

Hydrogen peroxide and medium chain carboxylic acid are delivered individually from second and third reagent supply vessels 124 and 23 via first and second lines 126 and 128, respectively, into a mix line 129 leading into guard column 30. In mix line 129 the hydrogen peroxide and medium chain carboxylic acid reagents combine into a medium chain reaction mixture, although combining may also occur in second monitored guard column 156.

In the embodiment schematically illustrated in FIG. 10, holding tank 38 and second holding tank 138 are optional. Holding tank 38 may be employed to collect short chain peroxycarboxylic acid composition. Second holding tank 138 may be employed to collect medium chain peroxycarboxylic acid composition. The peroxycarboxylic acid compositions can then be supplied (e.g., pumped) from these tanks in the desired proportions into mixed peracid holding tank 70. Alternatively, the holding tanks 38 and 138 can be omitted and the peroxycarboxylic acid compositions can be supplied directly from the reactor columns 34 and 134 in the desired proportions. In another embodiment, the generator includes one holding tank 38 or 138 and the mixed peracid holding tank 70. In this embodiment, holding tank 38 or 138 collects one excess peracid composition and then supplies that to the mixed peracid holding tank in the desired proportion. One peracid generator 70 or 72 then supplies peracid composition directly to mixed peracid holding tank 70.

Additional Components and Configurations

Figure 11:
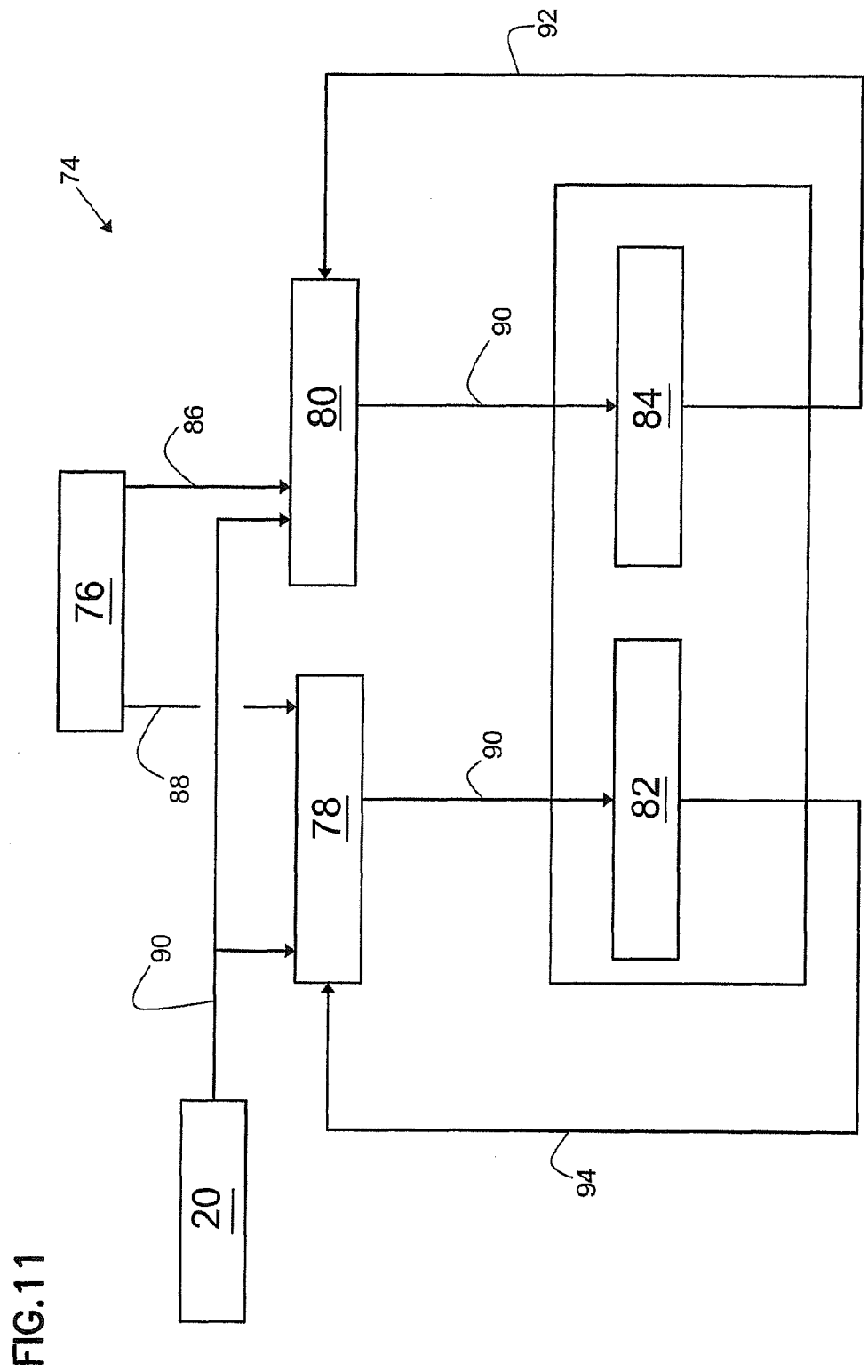
FIG. 11 schematically represents an embodiment of apparatus that generates peroxycarboxylic acid in fluid communication with an embodiment of aseptic packaging system.

FIG. 11 schematically illustrates a system including the peroxycarboxylic acid generator 20 and an aseptic packaging line 74. The peroxycarboxylic acid generator 20 is configured to provide peroxycarboxylic acid composition to the aseptic packaging line 74. Peroxycarboxylic acid generator 20 can be any of the embodiments illustrated or described herein.

In this embodiment, the peroxycarboxylic acid composition can be ready to use or can require dilution before use in aseptic packaging. The peroxycarboxylic acid generator 20 can provide ready to use peroxycarboxylic acid composition directly to bottle rinse tank 78 and/or cap rinse tank 80. When the peroxycarboxylic acid composition in supplied as a concentrate, aseptic packaging line 74 can include optional water source 76 to supply water for diluting the peroxycarboxylic acid composition. Water and peroxycarboxylic acid composition can mix in bottle rinse tank 78 and cap rinse tank 80. Water can be supplied to the rinse tanks through optional first and second water conduits 86 and 88. Peroxycarboxylic acid composition can be supplied to the rinse tanks through peracid conduit 90.

The diluted or ready to use composition can be applied to bottles and caps at bottle rinse station 82 and cap rinse station 84. The mixing tanks are in fluid communication with the rinsing stations through station conduits 90. Used composition can be recirculated through first and second recirculation conduits 92 and 94. The capped bottles can be removed from the system, for example, by a conveyor (not shown).

Figure 12:
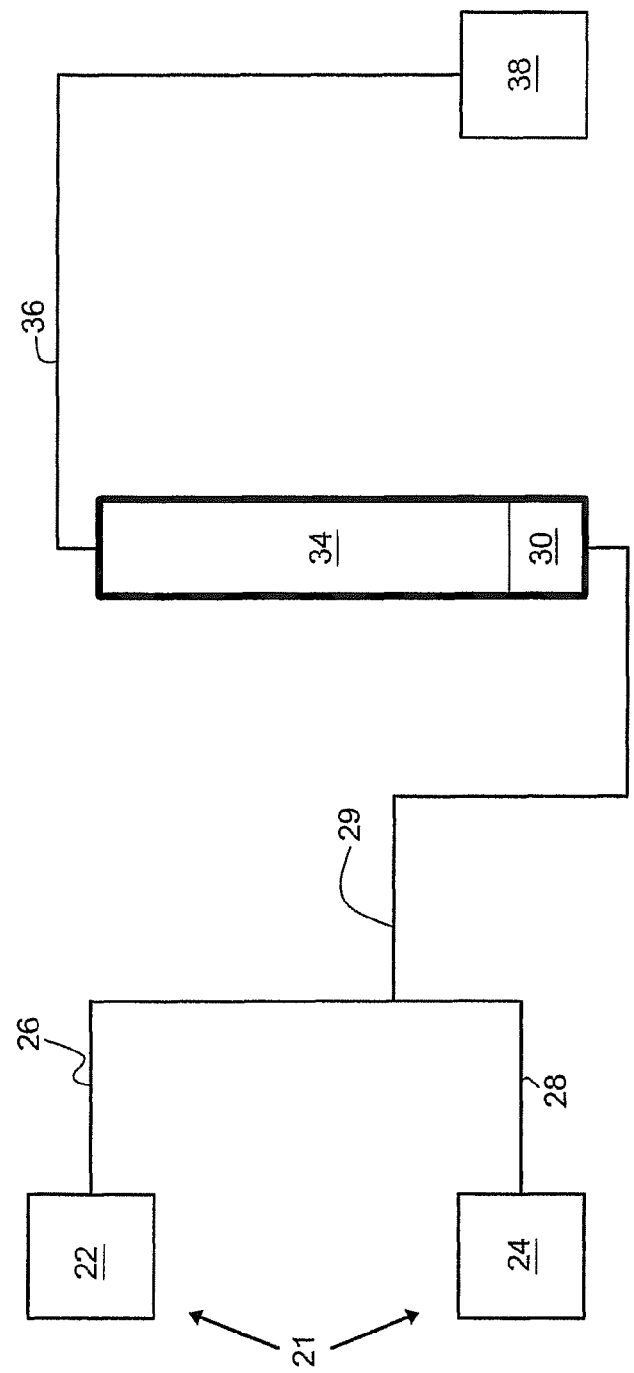
FIGS. 12 and 13 schematically represent embodiments of apparatus that generates peroxycarboxylic acid including embodiments of pretreatment column and reaction catalyst.

FIG. 12 schematically illustrates an embodiment, of the present peroxycarboxylic acid generator 20 in which guard column 30 is a cartridge or segment in reactor column 34. In FIG. 12, one or more reagent supply vessels 21, for example, first reagent supply vessel 22 containing hydrogen peroxide and second reagent supply vessel 24 containing one or more carboxylic acids are coupled by first and second lines 26 and 28 and mixing line 29 to guard column 30. Guard column 30 contains a cation exchanger (not shown) that removes metal ions from the reaction mixture. The reaction mixture then proceeds to the one or more reactor columns 34. Reactor column 34 is packed with strong acid catalyst (not shown). The peroxycarboxylic acid composition is discharged from a reaction column 34 via third line 36, for example, into a holding tank 38. In this embodiment, the guard column 30 and/or cation exchanger can be exchanged into and out of the reaction column 34, for example, when the safety system so indicates or after a certain amount of use. The guard column can make up the first about the first 1 vol-% to about the first 50 vol-%, for example about 10 to about 15 vol-%, of the combined guard and reaction columns 30 and 34. Such a guard column 30 can be employed in any of the illustrated embodiments.

Figure 13:
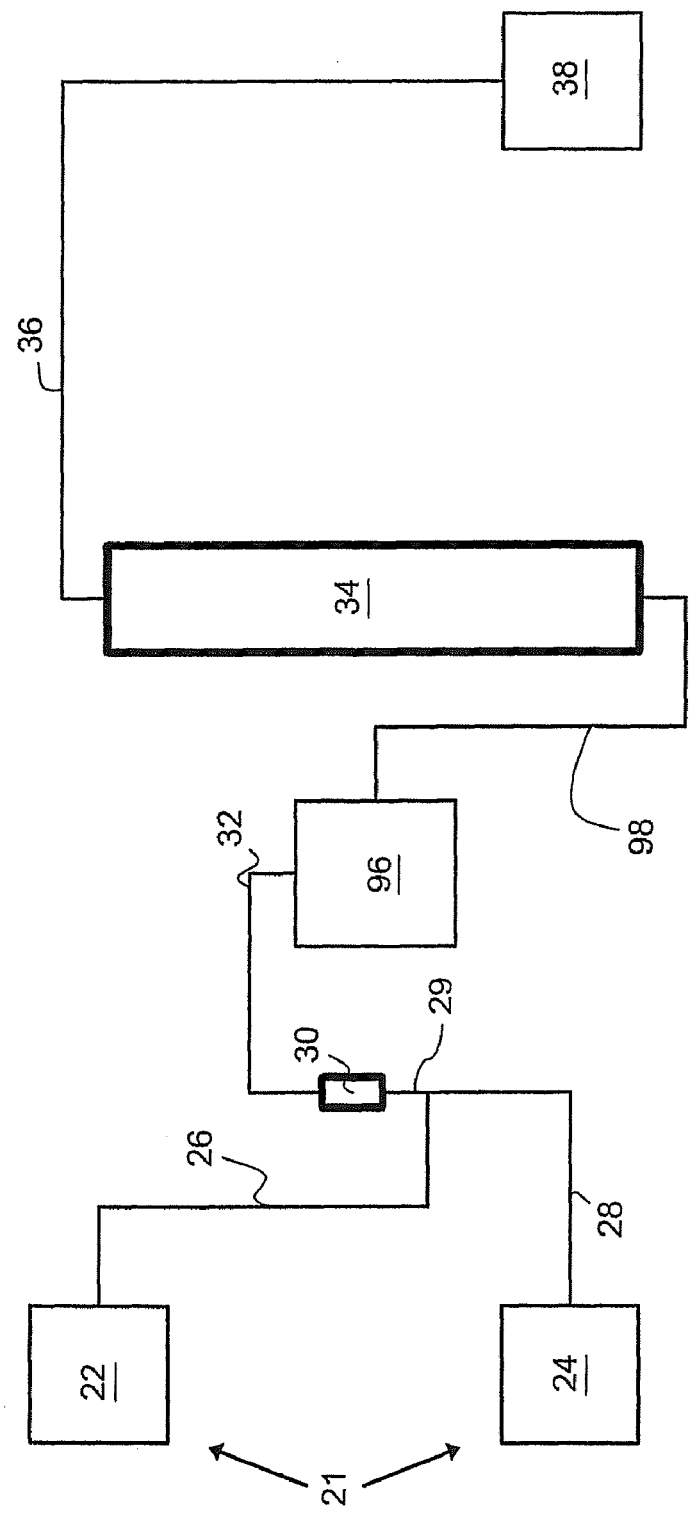

FIG. 13 illustrates an embodiment of the present peroxycarboxylic acid generator 20 including middle tank 96. In FIG. 13, one or more reagent supply vessels 21, for example, first reagent supply vessel 22 containing hydrogen peroxide and second reagent supply vessel 24 containing one or more carboxylic acids are coupled by first and second lines 26 and 28 and mixing line 29 to guard column 30. The reaction mixture proceeds through guard column 30 and third line 32 to middle tank 96. The reagent or mixed reagents can accumulate in middle tank 96. In an embodiment including a reagent guard column 40 or 140, middle tank 96 can be positioned after the reagent guard column 40 or 140 and/or after guard column 30. Middle tank 96 is coupled to reactor column 34 by middle line 98. Reactor column 34 is packed with strong acid catalyst (not shown). The peroxycarboxylic acid composition is discharged from a reaction column 34 via third line 36, for example, into a holding tank 38.

In an embodiment, middle tank 96 can be configured to receive one or more reagents from guard column 30 and/or reagent guard column 40 and to contain the reagent(s). The generator 20 can be configured so that middle tank 96 is simultaneously in fluid communication with guard column 30 and/or reagent guard column 40 and with reactor column 34. In an embodiment, the generator 20 is configured so that the middle tank 96 is in fluid communication with guard column 30 and/or reagent guard column 40 and with reactor column 34 at different times or at overlapping times. In an embodiment, the generator 20 is configured so that the middle tank 96 can in be in a first position for receiving reagent(s) from guard column 30 and/or reagent guard column 40 and transported to a second position to provide reagents to the reactor column 34. That is, in such an embodiment, generator 20 can be configured into two separate sets of equipment. The first set of equipment can include all of the components upstream (in the direction of guard column 30 and/or reagent guard column 40) from middle tank 96 and the second set of equipment can include all of the components downstream (in the direction of reactor column 34) from middle tank 96.

Any of the embodiments illustrated in FIGS. 1-13 can include a middle tank 96 and/or can be configured as first and second sets of components.

Figure 14:
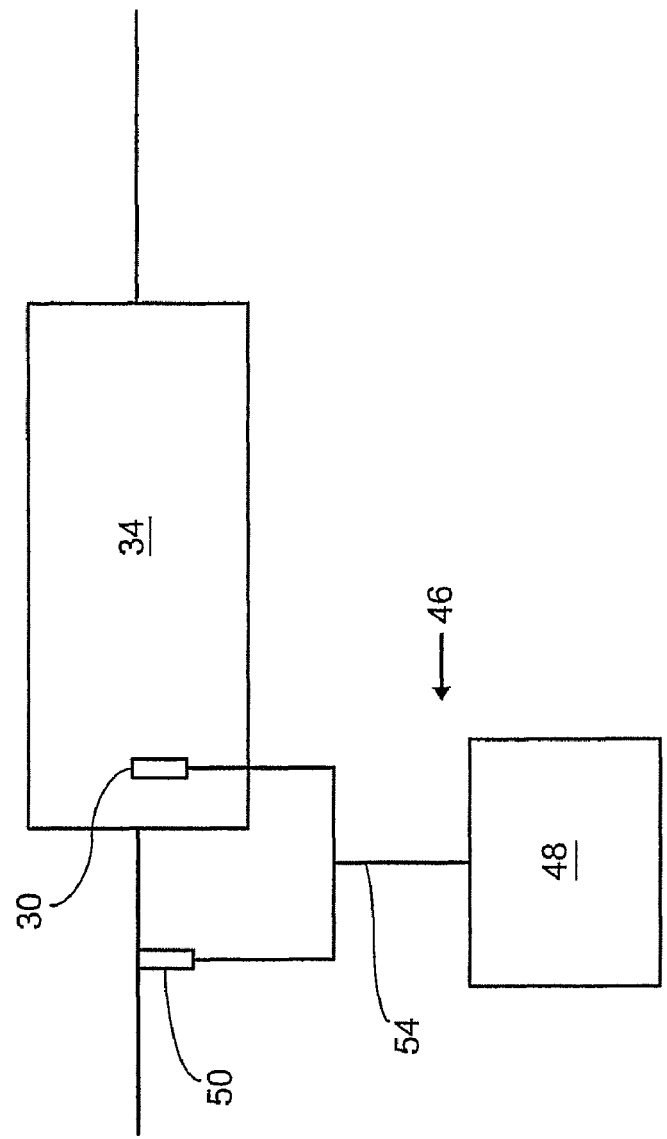
FIG. 14 schematically represents embodiments of the safety system and reaction catalyst.

FIG. 14 illustrates an embodiment of reactor column 34 and monitoring device 46, which is an embodiment of the safety system. Monitoring device 46 includes controller 48 and first and second sensors 50 and 52, respectively, and lead 54. Lead 54 couples first and second sensors 50 and 52 to controller 48. In the illustrated embodiment, first sensor 50 monitors the condition (e.g., temperature or pressure) of the reaction mixture in third line 32 and second sensor 52 monitors the condition within reactor column 34. In an embodiment, second sensor can be positioned into reactor column 34 about 10 to about 25% of the distance along the axis of reactor column 34. Alternatively, the sensors can be positioned as described above for positioning sensors in guard column 30.

In an embodiment such as that illustrated in FIG. 14, the safety system can measure conditions at an inlet or outlet of a reactor column 34, within reactor column 34 (e.g., near the entrance of the column, in the interior of the column, or near the exit from the column), or in a conduit entering or leaving the reactor column 34. Another embodiment of the safety system can quantify the amount of metal that enters or has entered the reactor column 34. In an embodiment, the safety system is configured to measure temperature at the entrance to the reactor column 34 and in the first 25% of the reactor column 34.

Monitoring and Control of Use Compositions

Figure 15:
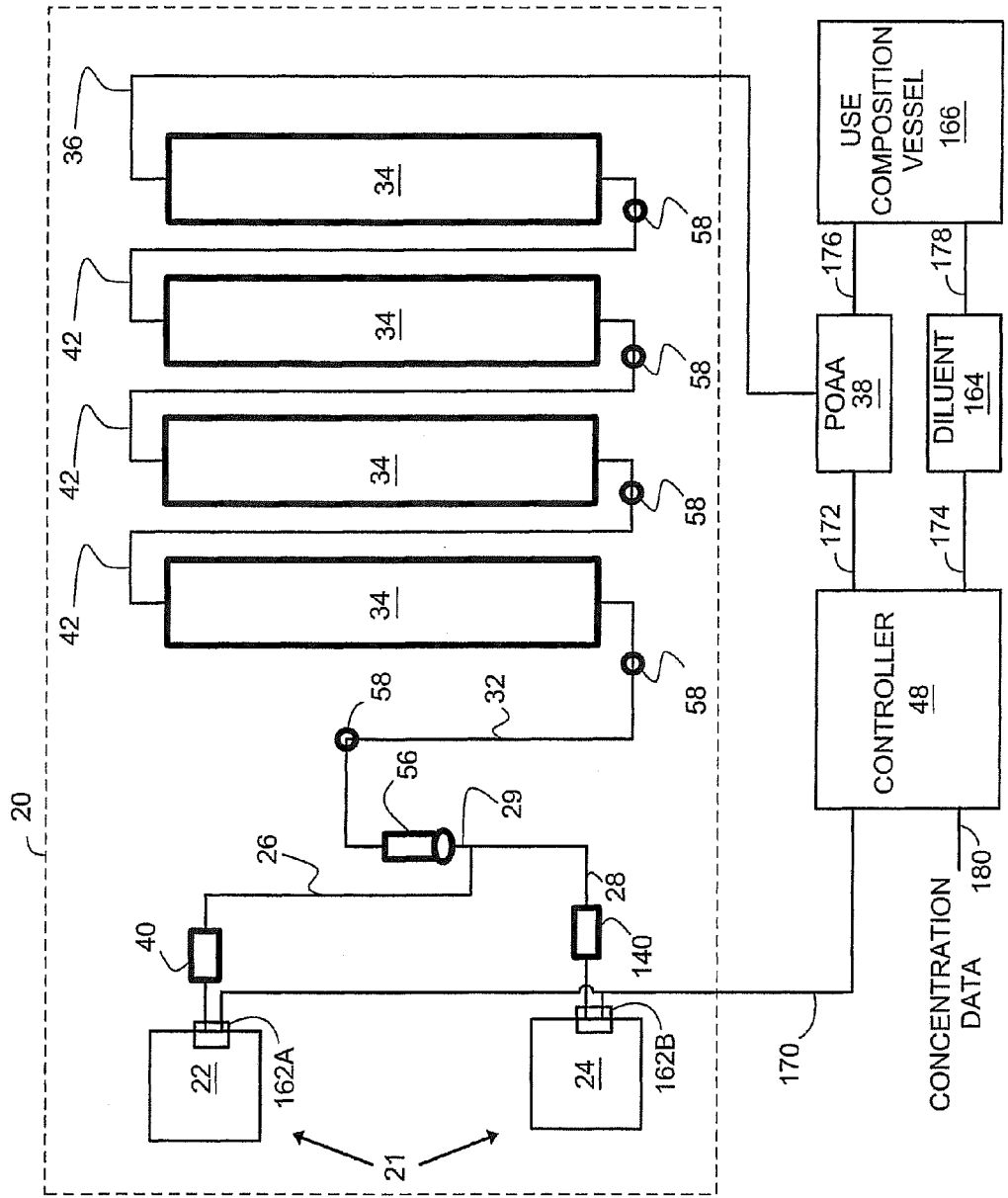
FIG. 15 schematically represents embodiments of apparatus that generates peroxycarboxylic acid including an embodiment of storage system.

FIG. 15 is a schematic diagram illustrating an embodiment of a peroxycarboxylic acid generator 20, a controller 48, a POAA holding tank 38, a diluent holding tank 16 and a use composition vessel 166. Controller 48 may manage several functions with respect to peroxycarboxylic acid generator 20. For example, controller 48 may control various safety system functions as described above with respect to FIG. 6. Controller 48 may also manage dilution of the concentrate composition generated by peroxycarboxylic acid generator 20 to form a use composition.

In addition, controller 48 receives concentration data concerning the concentrations of peroxycarboxylic acid and hydrogen peroxide in the use composition via line 180. Based on the concentration data, controller 48 may monitor the concentration of peroxycarboxylic acid and/or hydrogen peroxide in the use composition and replenish the use composition when these concentrations do not satisfy predetermined criteria. In addition, controller 48 may, based on the concentration data, regulate various operating parameters of peroxycarboxylic acid generator 20 to affect the concentration of peroxycarboxylic acid in the peroxycarboxylic acid concentrate composition output on line 36.

The concentrations of peroxycarboxylic acid and/or of hydrogen peroxide in the use composition may be determined in any number of ways. An example apparatus that may be used to determine the concentrations of peroxycarboxylic acid and/or of hydrogen peroxide in the use composition is the Oxycheck System, available from Ecolab Inc. of St. Paul, Minn. The concentration data may also be determined manually. For example, concentration could be obtained by any number of conventional techniques such as titration, potentiometric or amperometric techniques. However, it shall be understood that the invention is not limited in this respect, and that the concentration data may be determined in any number of ways without departing from the scope of the present invention.

To manage dilution of the concentrate composition, controller 48 may add and/or mix into the peroxycarboxylic acid concentrate stored in POAA holding tank 38 a diluent, such as water, stored in diluent holding tank 164. In one embodiment, controller 48 may regulate one or more valves or pumps that control the flow of the carboxylic acid concentrate composition from POAA holding tank 38 and diluent from diluent holding tank 164. Controller 48 may regulate the pump or pumps such that the carboxylic acid composition and diluent flow into use composition vessel 166 in a desired proportion to achieve a use composition containing, for example, a target concentration of peroxycarboxylic acid.

Controller 48 may replenish the use composition when the concentrations of peroxycarboxylic acid and/or hydrogen peroxide do not satisfy predetermine criteria. For example, based on the concentration data, controller 48 may regulate addition of peroxycarboxylic acid concentrate from POAA holding tank 38 or diluent 164 to the use composition 166 to ensure that the concentrations of peroxycarboxylic acid and/or hydrogen peroxide in the use composition satisfy the predetermined criteria. If, for example, the concentration of peroxycarboxylic acid in the use composition is too low, controller 48 may manage addition of additional peroxycarboxylic acid concentrate may to the use composition until a target concentration of peroxycarboxylic acid in the use composition is met. If the concentration of peroxycarboxylic acid in the use composition is too high, controller 48 may manage addition of additional diluent to the use composition until the target concentration of peroxycarboxylic acid in the use composition is met. The target concentration may include a specific concentration or may include a range of acceptable concentrations. As another example, if the concentration of hydrogen peroxide is too high, controller 48 may manage the emptying of the use composition vessel and production of a new use composition.

Figure 16:
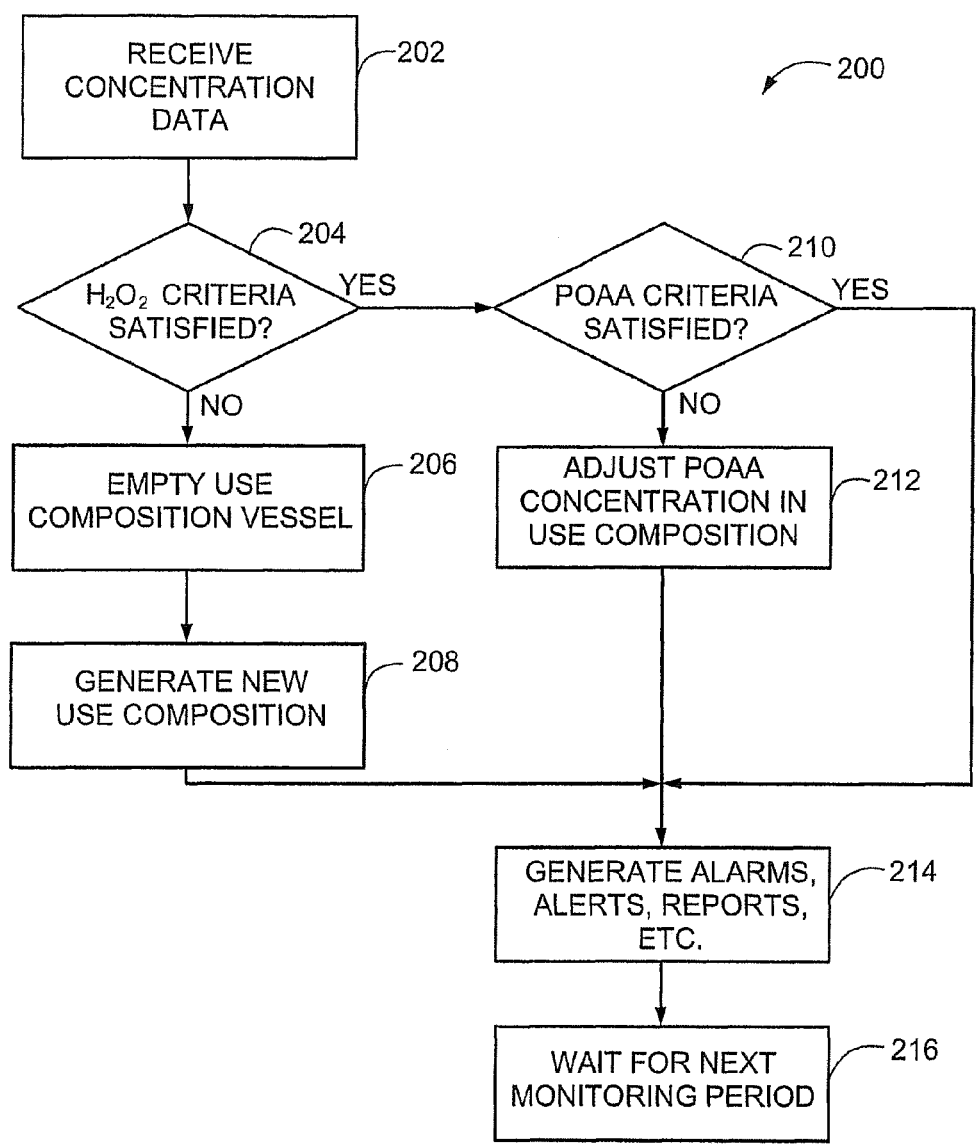
FIG. 16 is a flow chart illustrating an embodiment of a process by which the controller monitors and/or regulates the concentrations of peroxycarboxylic acid and/or of hydrogen peroxide in the use composition.

FIG. 16 is a flow chart illustrating the process (200) by which controller 48 monitors and/or regulates the concentrations of peroxycarboxylic acid and/or of hydrogen peroxide in the use composition. Once controller 48 receives the concentration data (202), controller 48 compares the received hydrogen peroxide concentration with predetermined $H_2O_2$ target criteria (204). If the received hydrogen peroxide concentration does not satisfy the $H_2O_2$ target criteria, controller 48 may manage the emptying of the use composition vessel to the spent use composition (206). In other words, controller 48 may generate a control signal or sequence of control signals that cause the use composition vessel to be emptied of the spent use composition. Controller 48 then manages production of a new use composition by managing the flow of peroxycarboxylic acid and diluent into use composition vessel 166 (208).

If the hydrogen peroxide concentration satisfies the predetermined $H_2O_2$ target criteria (204), controller 48 compares the peroxycarboxylic acid concentration in the use composition with predetermined POAA target criteria (210). If the peroxycarboxylic acid concentration in the use composition does not satisfy the POAA target criteria, controller 48 may manage replenishing of the use composition. That is, controller 48 may adjust the peroxycarboxylic acid concentration in the use composition until it satisfies the POAA target criteria (212). To do this, controller 48 may control valves or pumps on POAA concentrate holding tank 38 and/or diluent holding tank 164 such that a given amount of peroxycarboxylic acid and/or diluent is added to the use composition in use composition vessel 166, causing a resultant increase or decrease in the concentration of peroxycarboxylic acid in the use composition.

In one embodiment, controller 48 may compute the amount of peroxycarboxylic acid concentrate or diluent to be added to the use composition, for example, based on the known concentration of peroxycarboxylic acid in the use composition and the known or expected concentration of peroxycarboxylic acid in the concentrate holding tank 38. In another embodiment, controller 48 may iteratively add incremental amounts of peroxycarboxylic acid and/or diluent to the use composition until the target concentration of peroxycarboxylic acid in the use composition is reached.

After a new composition is produced (208) or the POAA concentration in the use composition is replenished/adjusted (212), controller 48 may record the information concerning the timing, received concentration data, amount of use composition made or the relative amounts of concentrate or diluent required to bring use composition into satisfactory compliance with the POAA and/or $H_2O_2$ target criteria. Controller 48 may also analyze the data and generate various alarms, alerts, or reports based on the stored information and the results of the analysis. The alarms, alerts or reports may be communicated to a user via audio alarms such as beepers, buzzers or recorded scripts and/or visual indicators such as LEDS, numerical, graphical or interactive displays on peroxycarboxylic acid generator 20. The alarms, alerts or reports may also be sent, either by request or at periodic intervals, to a remote monitoring site via a telephone network, wireless network, e-mail, local area network, wide area network or the internet. Further, the alarms, alerts or reports may be obtained on site or remotely via a portable device such as a laptop computer, tablet PC, personal digital assistant or other handheld or portable devices. Controller 48 then waits for initiation of the next monitoring period (214), at which point controller 48 will receive the most recently measured concentrations of peroxycarboxylic acid and/or hydrogen peroxide. The next monitoring period may be initiated by a user, either locally or remotely, or controller 48 may be programmed to periodically monitor and/or regulate the peroxycarboxylic acid and/or hydrogen peroxide concentrations in the use composition.

The $H_2O_2$ target criteria and POAA target criteria may vary depending upon the application to which the use solution is directed. For example, the $H_2O_2$ target criteria and POAA target criteria may vary depending upon the degree of efficacy required for the particular application to which the use solution is directed. In one embodiment, the POAA target criteria may be a minimum or a maximum POAA target concentration (e.g., the measured POAA concentration in the use solution must remain above a minimum POAA concentration or below a maximum POAA concentration). In another embodiment, the POAA target criteria may be a range of acceptable POAA concentrations (e.g., the measured POAA concentration in the use solution must remain above a minimum POAA concentration and below a maximum POAA concentration). Likewise, in one embodiment, the $H_2O_2$ target criteria may be a minimum or a maximum $H_2O_2$ target concentration (e.g., the measured $H_2O_2$ concentration in the use solution must remain above a minimum $H_2O_2$ concentration or below a maximum $H_2O_2$ concentration). In another embodiment, the $H_2O_2$ target criteria may be a range of acceptable $H_2O_2$ concentrations (e.g., the measured $H_2O_2$ concentration in the use solution must remain above a minimum $H_2O_2$ concentration and below a maximum $H_2O_2$ concentration).

Another function of controller 48 may be to monitor the overall performance of peroxycarboxylic acid generator 20. Controller 48 may analyze the concentration data concerning the concentrations of peroxycarboxylic acid and hydrogen peroxide in the use composition to infer information concerning operation of the peroxycarboxylic acid generator 20. For example, peroxycarboxylic acid generator 20 is designed to generate a peroxycarboxylic acid concentrate composition having a known, controllable peroxycarboxylic acid concentration. From this known concentration, the concentrate composition in POAA holding tank 38 is mixed with a known volume of diluent to arrive at a corresponding expected and predictable POAA concentration in the use composition stored in use composition vessel 166. Concentration data indicating a lower than expected POAA concentration in the use composition may suggest that the concentration of peroxycarboxylic acid in the POAA concentrate is not at the expected level. This in turn may suggest that peroxycarboxylic acid generator 20 is not performing according to specifications.

Controller 48 may take any of several courses of action when concentration data indicating a lower than expected POAA concentration in the use composition, and thus a lower than expected POAA concentration in the concentrate composition, is received. For example, controller 48 may compensate for a lower or higher than expected POAA concentration in the use composition by adjusting certain operating parameters of peroxycarboxylic acid generator 20 such that the resulting concentration of peroxycarboxylic acid in the POAA concentrate composition output on line 36 is increased or decreased. This may be an iterative process which is repeated until a desired concentration of peroxycarboxylic acid in the POAA concentrate output on line 36 is achieved. For example, controller 48 may control operation of pumps 162A and/or 162B to adjust the amount of reagent flowing out of reagent supply vessels 22 and/or 24 and into peroxycarboxylic acid generator 20 to cause a corresponding increase or decrease in the concentration of the POAA concentrate generated.

Alternatively or in addition to compensating for lower/higher than expected concentrations, controller 48 may generate alarms, alerts or reports directed to a user that maintenance of certain components of peroxycarboxylic acid generator 20 may be required. For example, one or both of reagent supply vessels 22 or 24 may need to be replenished or pump or valve parameters may require adjustment. Analysis and reports of the data may also be generated. For example, statistical trending of the acetic acid and hydrogen peroxide pump rates versus the concentrations of POAA and hydrogen peroxide within vessel 38 can be used to predict conversion efficiency.

Figure 17:
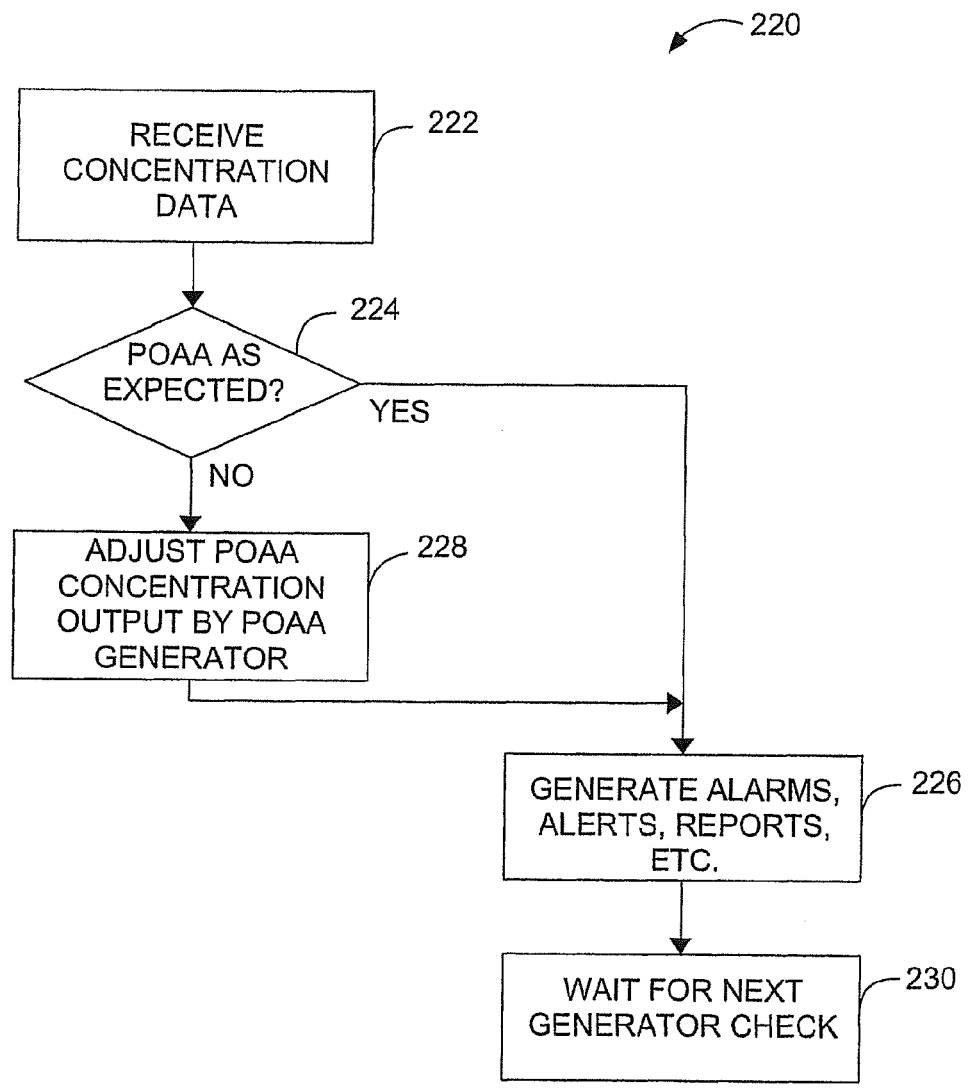
FIG. 17 is a flowchart illustrating an embodiment of a "generator check" process by which the controller monitors and regulates operation of peroxycarboxylic acid generator.

FIG. 17 is a flowchart illustrating an example "generator check" process (220) by which controller 48 monitors and regulates operation of peroxycarboxylic acid generator 20. Once the concentration data concerning the concentrations of peroxycarboxylic acid and/or hydrogen peroxide in the use composition are received (222), controller 48 compares the peroxycarboxylic acid concentration to an expected POAA concentration (224). If the concentration of peroxycarboxylic acid does not meet the expected POAA concentration (224), controller 48 may adjust certain operating parameters of peroxycarboxylic acid generator 20 to cause a resultant change in the peroxycarboxylic acid concentration in the POAA concentrate (228).

For example, controller 48 may control operation of pumps 162A and/or 162B to adjust the amount of reagent flowing out of reagent supply vessels 22 and/or 24 and into peroxycarboxylic acid generator 20 to cause a corresponding increase or decrease in the concentration of the POAA concentrate composition output on line 36. Controller 48 may also increase or slow the flow rate of the reaction mixture through the reaction catalyst to a flow rate that results in the desired concentration. Controller 48 may calculate the change in flow rate employing factors including the temperature of the composition and the concentration of peroxycarboxylic acid. Based on the equilibration reaction kinetics and thermodynamics, contact time to the reaction catalyst will determine the end concentration of POAA, just as the concentration of the reactant species. In this way, the concentration of peroxycarboxylic acid in the use composition may be maintained within an expected range, even when generator 20 is not operating entirely up to specifications.

After the POAA concentration has been checked and adjusted, if necessary (224, 228), controller 48 may record and store the information concerning the timing, received concentration data, specific adjustments made to the various operating parameters of generator 20 (i.e., specific adjustments to parameters such as pump and/or valve speed and timing, the amounts of additional POAA or hydrogen peroxide added from reagent vessels 22 and/or 24 to get the system back up to specifications, etc.). This information may be useful to service personnel in performing diagnostic and maintenance tasks on generator 20, and in monitoring efficiency of peroxycarboxylic acid generator 20. For example, if the system continuously generates a product identified as low in POAA content, this indicates the system will require service by changing the reaction catalyst.

Controller 48 may also analyze the information and generate various alarms, alerts, or reports based on this stored information. The alarms, alerts or reports may be communicated to a user via audio alarms such as beepers, buzzers or recorded scripts and/or visual indicators such as LEDS, numerical, graphical or interactive displays on peroxycarboxylic acid generator 20. The alarms, alerts or reports may also be sent, either by request or at periodic intervals, to a remote monitoring site via a telephone network, wireless network, e-mail, local area network, wide area network or the internet. Further, the alarms, alerts or reports may be obtained on site or remotely via a portable device such as a laptop computer, tablet PC, personal digital assistant or other handheld or portable devices.

Controller 48 then waits for initiation of the next generator check (230), at which point controller 48 will receive the most recent concentration data. The next generator check may be initiated by a user, either locally or remotely, or controller 48 may be programmed to perform generator checks at predetermined periodic intervals. For example, controller 48 may repeat the process shown in FIG. 17 periodically to ensure that generator 20 is performing in accordance with specifications and to ensure that the desired level of peroxycarboxylic acid in the use composition is maintained. Generator checks may be performed, for example, on a daily, weekly or monthly basis.

Methods of Making Peroxycarboxylic Acids

The present invention includes a method for making a peroxycarboxylic acid. The method includes contacting a reagent with a pretreatment column and a reaction mixture with a reaction catalyst. Contacting can include contacting one or more reagents employed in making the peroxycarboxylic acid with, for example, a cation exchanger in acid form or inert metal (e.g., $Na^+$ or $K^+$) form. The reagent can include hydrogen peroxide, carboxylic acid, or a mixture of hydrogen peroxide and carboxylic acid. Contacting with the reaction catalyst can include contacting the catalyst with carboxylic acid (or suitable precursor) and oxidizing agent (e.g., a peroxide) to form a peroxycarboxylic acid. The reaction catalyst can be a strong acid (e.g., a polystyrene sulfonic acid) to catalyze reaction of hydrogen peroxide with carboxylic acid to form peroxycarboxylic acid. Pretreating one or more reagents can increase the life, activity, and/or safety of the reaction catalyst.

The method can also include monitoring the safety of the method and the apparatus carrying it out. Monitoring safety can include monitoring and/or regulating one or more conditions of the pretreatment column and/or the reaction catalyst. Monitoring can include monitoring and/or regulating pressure, temperature, metal content, and/or presence of gas resulting from decay of peroxide (e.g., oxygen). Measuring of one or more of these parameters can take place at or in the pretreatment column, at or in the reaction catalyst, for one or more of the reagents before, in, or after a pretreatment column, for the reaction mixture before, in, or after a pretreatment column, for the reaction mixture before, in, or after the reaction catalyst, or more than one of these (a combination thereof). Measuring can include determining a difference in one or more of these parameters between any two points, for example, between any two of the listed locations.

The method can include providing one or more reagents (e.g., hydrogen peroxide or carboxylic acid(s)) in one or more reagent vessels. Mixing of the reagents can take place before or after one or more of the reagents contact a pretreatment column. Reacting the pretreated reaction mixture or mixture of pretreated reactant with untreated reactant then occurs by contacting with the reaction catalyst. Reacting can include contacting the reaction mixture with the reaction catalyst at a controlled and predetermined flow rate and/or for a predetermined time. Reacting produces peroxycarboxylic acid. The method can also include using or storing the peroxycarboxylic acid.

In an embodiment, the method includes pretreating one or more reagents independently of the others. Mixing of the one or more pretreated reagents with an untreated reagent can then occur before pretreating the mixed reagents. Alternatively, each reagent can be pretreated independently and then mixed and contacted with the reaction catalyst. Each pretreatment takes place for a predetermined time to provide the desired amount of contaminant removal from the pretreated composition.

Pretreating can employ a plurality of (e.g., two) pretreatment columns coupled in parallel. One column can be idle while the other column is pretreating. The method can include switching flow from a used pretreatment column to a pretreatment column that is ready for use. The method can include replacing, maintaining, washing, or the like the pretreatment column that is not being used. Washing can include washing with, for example, a dilute strong mineral acid, such as sulfuric acid. Washing can include back flushing the pretreatment column. The method can continue while one of the pretreatment columns is being maintained or replaced. Changing columns can be done according to a predetermined schedule. Alternatively, the method can include monitoring the safety of the pretreatment column and replacing it when the monitoring finds a predetermined condition.

Contacting the reaction mixture with the reaction catalyst can occur in one or more beds, bags, or columns, which can be coupled in series, in parallel, or with some in series and some in parallel. The method can employ contacting with four columns containing reaction catalyst and connected in series. Reacting can employ a bed, bag, or column until that bed, bag, or column has received sufficient use or is in a condition that indicates it is no longer fit for use. During reacting on a first bed, bag, or column, a second bed, bag, or column can remain ready for use. The method can include switching flow from the first bed, bag, or column to the second bed, bag, or column when the first is no longer to be used.

The condition of the bed, bag, or column that is in use can be measured by the safety system, which can also control the valve system. Changing reaction catalysts can be done according to a predetermined schedule. Alternatively, the method can include monitoring the safety of the reaction catalyst and replacing it when the monitoring finds a predetermined condition. The method can include washing the reaction catalyst. Washing can include washing with, for example, a dilute strong mineral acid, such as sulfuric acid. Washing can include back flushing a bed, bag, or column of the reagent catalyst.

Monitoring safety can include measuring one or more properties of the pretreatment column, of the reaction catalyst, or both. Monitoring safety can include measuring, for example, pressure (e.g., increased pressure), temperature (e.g., increased temperature), or both. In an embodiment, measuring can include measuring a difference in temperature between two points in or around (e.g., before and after or before and in) the pretreatment column. Measuring an increase in the difference in temperature or difference in pressure for two points in or around a pretreatment column can result in the system providing a perceptible signal if the increase is above a predetermined level. Measuring a change above the predetermined level can trigger (manual or automated) actuating a pressure release valve, stopping flow of one or more reagents, causing water to flow into the pretreatment column, causing carboxylic acid composition to flow into the pretreatment column, shutting down the method, or a combination thereof. Triggering can also result in switching to another pretreatment column or bed or column of reaction catalyst.

Monitoring safety can include measuring conditions at an inlet or outlet of a pretreatment column, within that column (e.g., near the entrance of the column, in the interior of the column, or near the exit from the column), or in a conduit entering or leaving the pretreatment column. Monitoring can include measuring temperature at the entrance to the pretreatment column and in the first 25% of the pretreatment column.

The method can also include storing, handling, diluting, and formulating the composition made by the method. For example, the method can include using or storing the peroxycarboxylic acid. The method can include diluting and/or formulating the composition from the reaction catalyst or storage. The method can include diluting a concentrate fore use. Diluting can add and/or mix a diluent or carrier, such as water, into the peroxycarboxylic acid to achieve a diluted composition containing, for example, a desired use concentration of peroxycarboxylic acid. The desired concentration can be, for example, about 2 to about 5000 ppm. Diluting can include adding another ingredient to the peroxycarboxylic acid composition. Formulating can include dispensing a desired amount of an added ingredient into the composition or diluted composition.

Storing can include monitoring the condition of the composition during storage. Monitoring can measure the content of peroxycarboxylic acid, carboxylic acid, and/or hydrogen peroxide in the composition, for example, in a stored use composition. In an embodiment, the method includes replenishing system a stored use composition. Replenishing can include monitoring the content of the use composition. If, for example, the concentration of peroxycarboxylic acid decreases below a predetermined level or the concentration of carboxylic acid increases above a predetermined level, replenishing then includes adding more concentrated peroxycarboxylic acid composition to the use composition or emptying the vessel of the spent use composition.

The method can also include controlling reagent flow. Controlling reagent flow can include monitoring the peroxycarboxylic acid composition after the reaction catalyst, for example, at an outlet from the last reaction catalyst column. Monitoring can determine whether the composition includes the desired concentration of peroxycarboxylic acid (e.g., the equilibrium concentration). If the composition includes less than the desired concentration, the controlling can include slowing the flow rate of the reaction mixture through the reaction catalyst to a flow rate that results in the desired concentration. Controlling can include calculating the change in flow rate employing factors including the temperature of the composition and the concentration of peroxycarboxylic acid.

The present invention includes a method for making a composition including one peroxycarboxylic acid. The method includes contacting a carboxylic acid with a pretreatment column, mixing the pretreated carboxylic acid with hydrogen peroxide, and contacting the reaction mixture with a reaction catalyst to produce the peroxycarboxylic acid. The peroxycarboxylic acid can be a short chain peroxycarboxylic acid (e.g., peroxyacetic acid) or a medium chain peroxycarboxylic acid (e.g., peroxyoctanoic acid).

The present invention includes a method for making a composition of mixed peroxycarboxylic acids. The method includes contacting a short chain carboxylic acid with a first pretreatment column, mixing the pretreated short chain carboxylic acid with hydrogen peroxide, and contacting the first reaction mixture with a first reaction catalyst to produce the short chain peroxycarboxylic acid. The method includes contacting a medium chain carboxylic acid with a second pretreatment column, mixing the pretreated medium chain carboxylic acid with hydrogen peroxide, and contacting the second reaction mixture with a second reaction catalyst to produce the medium chain peroxycarboxylic acid. Mixing the short chain peroxycarboxylic acid and the medium chain peroxycarboxylic acid produces the mixed peroxycarboxylic acid composition.

Methods Conducted at the Site of Use

The present invention also relates to methods of making a peroxycarboxylic acid at the site of its use. For example, the method of making peroxycarboxylic acid described above can be conducted at a plant, e.g. a beverage plant, where the peroxycarboxylic acid will be used. The site of use can be any of a variety of production facilities where a peroxycarboxylic acid might be used. Sites of use include a beverage plant, a food processing plant, a disassembly plant, a meat processing plant, or the like. At the site of use, the peroxycarboxylic acid composition can be applied to objects including equipment, containers, and food products. Food products include, for example, plant product, product, meat, meat product, poultry, and the like. In an embodiment, the method can include applying the present peroxycarboxylic acid composition to a beverage container, e.g., a plastic bottle or a can.

For example, the method of making peroxycarboxylic acid described above can be conducted at a wood pulp producing or paper plant where the peroxycarboxylic acid will be used. By way of further example, the method of making peroxycarboxylic acid described above can be conducted at a waste treatment plant where the peroxycarboxylic acid will be used. Sites of use include any of a variety of plants that process, use or handle (e.g., bleach) pulp or make paper, plants that handle waste, such as industrial waste, food production waste, waste from a beverage plant, waste from a food processing plant, waste from a disassembly plant, waste from a meat processing plant, or the like. At the site of use, the peroxycarboxylic acid composition can be applied to objects including equipment, pulp, waste, plant surfaces and buildings, other objects in the plant or facility, or the like. In an embodiment, the method can include applying the present peroxycarboxylic acid composition to pulp, to waste, to a waste treatment facility, or to waste treatment equipment.

The method can include providing carboxylic acid (e.g., acetic acid and/or octanoic acid) and/or oxidizing agent (e.g., hydrogen peroxide) at the site of use (e.g., a beverage plant, a pulp processing plant, or a waste treatment plant) and conducting the present method with those reagents at the site of use. The method can include shipping the carboxylic acid (e.g., acetic acid and/or octanoic acid) and/or oxidizing agent (e.g., hydrogen peroxide) to the site of use (e.g., a beverage plant, a pulp processing plant, or a waste treatment plant) for conducting the present method with those reagents at the site of use. The method can include plant or plant organization personnel requesting or ordering the carboxylic acid (e.g., acetic acid and/or octanoic acid) and/or oxidizing agent (e.g., hydrogen peroxide) for delivery to the site of use (e.g., a beverage plant, a pulp processing plant, or a waste treatment plant) for conducting the present method with those reagents at the site of use.

An Embodiment of the Method

In an embodiment, the method includes contacting a reaction mixture with a reaction catalyst and monitoring the safety of the method and the apparatus carrying it out. The reaction mixture can include a mixture of hydrogen peroxide and carboxylic acid. Contacting with the reaction catalyst can include contacting the catalyst with carboxylic acid (or suitable precursor) and oxidizing agent (e.g., a peroxide) to form a peroxycarboxylic acid. The reaction catalyst can be a strong acid (e.g., a polystyrene sulfonic acid) to catalyze reaction of hydrogen peroxide with carboxylic acid to form peroxycarboxylic acid.

Monitoring safety can include monitoring and/or regulating one or more conditions of the reaction catalyst. Monitoring can include monitoring and/or regulating pressure, temperature, metal content, and/or presence of gas resulting from decay of peroxide (e.g., oxygen). Measuring of one or more of these parameters can take place at or in the reaction catalyst, for example, for the reaction mixture before, in, or after the reaction catalyst, or more than one of these (a combination thereof). Measuring can include determining a difference in one or more of these parameters between any two points, for example, between any two of the listed locations.

Monitoring safety can include measuring one or more properties of the reaction catalyst. Monitoring safety can include measuring, for example, pressure (e.g., increased pressure), temperature (e.g., increased temperature), or both. In an embodiment, measuring can include measuring a difference in temperature between two points in or around (e.g., before and after or before and in) the reaction catalyst. Measuring an increase in the difference in temperature or difference in pressure for two points in or around the reaction catalyst can result in the system providing a perceptible signal if the increase is above a predetermined level. Measuring a change above the predetermined level can trigger (manual or automated) actuating a pressure release valve, stopping flow of one or more reagents, causing water to flow into the reaction catalyst, causing carboxylic acid composition to flow into the reaction catalyst, shutting down the method, or a combination thereof. Triggering can also result in switching to another bed or column of reaction catalyst.

Monitoring safety can include measuring conditions at an inlet or outlet of a column, bed, or bag of reaction catalyst, within the column, bed, or bag of reaction catalyst (e.g., near the entrance, in the interior, or near the exit), or in a conduit entering or leaving the reaction catalyst. Monitoring can include measuring temperature at the entrance to the reaction catalyst and in the first 25% of the reaction catalyst.

This embodiment need not include pretreating the reagents in with material outside the column, bed, or bag of reaction catalyst.

Peroxycarboxylic Acid Compositions

The present method and apparatus can be employed to make any of a variety of peroxycarboxylic acid compositions. In an embodiment, the present method includes a peroxycarboxylic acid composition made by the method and/or apparatus described hereinabove. A peroxycarboxylic acid composition according to the present invention can have advantageous stability, which can be due to a low level of metal ion (e.g., less than about 10 ppm or less than about 10 ppb metal ion). The low level of metal ion can be achieved and maintained in the present compositions without added stabilizer or chelating agent. Accordingly, the present invention relates to a stable peroxycarboxylic acid composition lacking or substantially free of stabilizer or chelating agent. The present invention also includes a stable peroxycarboxylic acid composition that includes only volatile compounds. The present invention also includes a peroxycarboxylic acid composition that includes only volatile compounds.

The term "stable" as applied herein to a peroxycarboxylic acid composition means a composition that retains about 90% of the peroxycarboxylic acid for at least about 6 months, that retains about 90% of the peroxycarboxylic acid for at least about 7 days, or that retains about 90% of the peroxycarboxylic acid for at least about 1 day. The stable composition can be one that retains about 95% of the peroxycarboxylic acid for at least about 14 days, that retains about 95% of the peroxycarboxylic acid for at least about 7 days, or that retains about 95% of the peroxycarboxylic acid for at least about 3 days. Being depleted of trace metals by the generator, the "90%" stability threshold is generally speaking a function of the equilibrium percarboxylic acid concentration. The higher concentrations tending to decompose more rapidly.

In certain embodiments, the present peroxycarboxylic acid composition includes metal ion at a level less than about 10 ppm, less than about 1 ppm, less than about 100 ppb, less than about 10 ppb, or less than about 1 ppb ppm. Such metal ion can include Fe, Cu, Mn, Ni, Ti, Co, a mixture thereof, or any of the transition metal ions.

In certain embodiments, the composition at equilibrium includes about 35 wt-% peroxycarboxylic acid and about 15 wt-% hydrogen peroxide; about 15 (e.g., 17) wt-% peroxycarboxylic acid and about 15 (e.g., 13) wt-% hydrogen peroxide; about 10 (e.g., 9.7) wt-% peroxycarboxylic acid and about 25 (e.g., 24) wt-% hydrogen peroxide; about 15 (e.g., 13) wt-% peroxycarboxylic acid and about 2 (e.g., 1.9) wt-% hydrogen peroxide, or about 0.5 wt-% peroxycarboxylic acid and about 5 (e.g., 4.8) wt-% hydrogen peroxide.

In certain embodiments, the composition at equilibrium includes about 35 wt-% short chain peroxycarboxylic acid and about 15 wt-% hydrogen peroxide; about 15 (e.g., 17) wt-% short chain peroxycarboxylic acid and about 15 (e.g., 13) wt-% hydrogen peroxide; about 10 (e.g., 9.7) wt-% short chain peroxycarboxylic acid and about 25 (e.g., 24) wt-% hydrogen peroxide; about 15 (e.g., 13) wt-% short chain peroxycarboxylic acid and about 2 (e.g., 1.9) wt-% hydrogen peroxide, or about 0.5 wt-% short chain peroxycarboxylic acid and about 5 (e.g., 4.8) wt-% hydrogen peroxide.

In certain embodiments, the composition at equilibrium includes about 20 (e.g., 19) wt-% medium chain peroxycarboxylic acid and about 30 (e.g., 32) wt-% hydrogen peroxide; about 5 (e.g., 6.8) wt-% medium chain peroxycarboxylic acid and about 20 wt-% hydrogen peroxide; about 2 (e.g., 2.1) wt-% medium chain peroxycarboxylic acid and about 20 (e.g., 21) wt-% hydrogen peroxide; or about 1 (e.g., 1.2) wt-% medium chain peroxycarboxylic acid and about 20 (e.g., 22) wt-% hydrogen peroxide.

In certain embodiments, the composition at equilibrium includes about 15 (e.g., 14) wt-% short chain peroxycarboxylic acid, about 5 (e.g., 5.7) wt-% medium chain peroxycarboxylic acid, and about 3 (e.g., 2.8) wt-% hydrogen peroxide; about 20 (e.g., 19) wt-% short chain peroxycarboxylic acid, about 3 (e.g., 2.7) wt-% medium chain peroxycarboxylic acid, and about 4 wt-% hydrogen peroxide; about 20 (e.g., 22) wt-% short chain peroxycarboxylic acid, about 1 (e.g., 0.7) wt-% medium chain peroxycarboxylic acid, and about 5 (e.g., 4.6) wt-% hydrogen peroxide; about 15 (e.g., 17.4) wt-% short chain peroxycarboxylic acid, about 0.4 wt-% medium chain peroxycarboxylic acid, and about 15 (e.g., 13) wt-% hydrogen peroxide.

In certain embodiments, the present composition includes peroxycarboxylic acid and hydrogen peroxide in a ratio of about 2:1 (e.g., 2.4:1); peroxycarboxylic acid and hydrogen peroxide in a ratio of about 1.4:1; peroxycarboxylic acid and hydrogen peroxide in a ratio of 0.5:1 (e.g., 0.4:1); or peroxycarboxylic acid and hydrogen peroxide in a ratio of about 7:1.

The present apparatus and method can be employed to make any of a variety of peroxycarboxylic acid compositions. Compositions that can be made by the present apparatus and method (which can include adding materials such as adjuvant, stabilizing agent, chelating agent, or the like after forming the peroxycarboxylic acid) include compositions disclosed in U.S. Pat. Nos. 5,200,189, 5,314,687, 5,718,910, and 6,183,807 and in pending U.S. application Ser. No. 09/614,631, filed Jul. 12, 2000, Ser. No. 10/754,426, filed Jan. 9, 2004, and Ser. No. 11/030,641, filed Jan. 4, 2005, the disclosures of which are incorporated herein by reference for disclosure of peroxycarboxylic acid compositions.

Embodiments of the Invention

Embodiments of the invention include, but are not limited to:

In an embodiment, the present invention includes an apparatus for making peroxycarboxylic acid. This embodiment of the apparatus can include a first pretreatment column, a first reaction catalyst column, a first and a second reagent vessel, a safety system, a reagent conduit, a reaction mixture conduit, and a peracid conduit. The first and second reagent vessels can be in fluid communication through the reagent conduit with the first pretreatment column. The first reagent vessel can be configured for containing a liquid oxidizing agent composition and the second reagent vessel can be configured for containing a liquid carboxylic acid composition. The reagent conduit can define mixing chamber for the reagents.

The first pretreatment column can be in fluid communication through the reaction mixture conduit with the first reaction catalyst column. The first pretreatment column can be configured for removing metal ion from a mixture of the carboxylic acid composition and the oxidizing agent composition. The first reaction catalyst column can be configured for catalyzing a reaction of the carboxylic acid and the oxidizing agent to produce peroxycarboxylic acid. The first reaction catalyst column can be in fluid communication through the peracid conduit with a site of storage or use of a peroxycarboxylic acid composition. The safety system including a processor, a first condition sensor, and a second condition sensor. The first condition sensor can be disposed in or on the mixing chamber and can be configured for measuring a condition of the reagents. The second condition sensor can be disposed at or in the first pretreatment column or in the reaction mixture conduit proximal an exit from the first pretreatment column and can be configured for measuring the condition of the reagents. The processor can be configured for determining a difference between the condition measured by the first condition sensor and the condition measured by the second condition sensor and providing a detectable signal if the difference meets or exceeds a predetermined value.

In an embodiment, the first pretreatment column includes a strong cation exchanger in acid form or in inert metal form.

The apparatus can also include a second pretreatment column. The second pretreatment column can be in fluid communication through the reagent conduit with the second reagent vessel and the first pretreatment column. The second pretreatment column can be configured for removing metal ion from the carboxylic acid composition. In an embodiment, the second pretreatment column can include a strong cation exchanger in acid form or in inert metal form.

The apparatus can also include a third pretreatment column. The third pretreatment column can be in fluid communication through the reagent conduit with the first reagent vessel and the first pretreatment column. The third pretreatment column can be configured for removing metal ion from the oxidizing agent composition. In an embodiment, the third pretreatment column can include a strong cation exchanger in acid form or in inert metal form.

The apparatus can also include a second, a third, and a fourth reaction catalyst column. The first, second, third, and fourth reaction catalyst columns can be coupled in series and can be in fluid communication through the peracid conduit with the site of storage or use of the peroxycarboxylic acid composition.

In an embodiment, the reaction catalyst includes a strong acid catalyst that can be physically removed from the reaction mixture. In an embodiment, the reaction catalyst includes a strong cation exchanger in acid form. In an embodiment, the reaction catalyst includes an inorganic compound including an insoluble strong acid.

The first and second condition sensors can be configured to measure temperature, pressure, metal content, or combination thereof. For example, the first and second condition sensors are configured to measure temperature.

In an embodiment, the safety system is configured to provide a detectable signal if the temperature difference is greater than 10° C., equal to 10° C., or greater than or equal to 10° C.

The detectable signal can actuates interruption of operation of the apparatus. For example, the detectable signal can actuate interruption of operation of the apparatus by: actuating a pressure release valve to release pressure in the first pretreatment column; stopping flow of one or more reagents into the columns; causing water to flow through the reagent conduit, the first pretreatment column, and the reaction mixture conduit; causing carboxylic acid composition to flow through the reagent conduit, the first pretreatment column, and the reaction mixture conduit; shutting down the apparatus; or a combination thereof.

The apparatus can also include a peracid vessel, a dilution system, a dilute tank, a replenishing system, and an output conduit. The peracid vessel can be in fluid communication with the peracid conduit and can be configured to receive and contain the peroxycarboxylic acid composition. The peracid vessel can be in fluid communication through the output conduit with the dilution system. The dilution system can be configured to mix the peroxycarboxylic acid composition and a predetermined amount of carrier to form a diluted composition of a predetermined concentration of peroxycarboxylic acid in the dilute tank. The replenishing system can be configured to monitor a concentration of peroxycarboxylic acid, carboxylic acid, oxidizing agent, or combination thereof in the diluted composition and to add peroxycarboxylic acid composition to the diluted composition if the concentration of peroxycarboxylic acid, carboxylic acid, oxidizing agent, or combination thereof is less than a predetermined value, equal to a predetermined value, or less than or equal to a predetermined value.

In yet another embodiment, the apparatus can also include a fourth pretreatment column, a fifth reaction catalyst column, a third and a fourth reagent vessel, a medium reagent conduit, a medium reaction mixture conduit, and a medium peracid conduit. The third and fourth reagent vessels can be in fluid communication through the medium reagent conduit with the fourth pretreatment column. The third reagent vessel can be configured for containing a liquid composition of oxidizing agent, the fourth reagent vessel can be configured for containing a liquid composition of medium chain carboxylic acid. The medium reagent conduit can define medium mixing chamber for the medium reagents. The fourth pretreatment column can be in fluid communication through the medium reaction mixture conduit with the fifth reaction catalyst column. The fourth pretreatment column can be configured for removing metal ion from a mixture of the liquid composition of medium chain carboxylic acid and the oxidizing agent composition. The fifth reaction catalyst column can be configured for catalyzing a reaction of the medium chain carboxylic acid and the oxidizing agent to produce medium chain peroxycarboxylic acid. The fifth reaction catalyst column can be in fluid communication through the medium peracid conduit with a site of storage or use of a medium chain peroxycarboxylic acid composition. The fourth pretreatment column can include a strong cation exchanger in acid form or in inert metal form.

In this or another embodiment, the safety system can also include a third condition sensor and a fourth condition sensor. The third condition sensor can be disposed in or on the medium mixing chamber and can be configured for measuring a condition of the medium reagents. The fourth condition sensor can be disposed at or in the fourth pretreatment column or in the medium reaction mixture conduit proximal an exit from the fourth pretreatment column and can be configured for measuring the condition of the medium reagents. The processor can be configured for determining a difference between the condition measured by the third condition sensor and the condition measured by the fourth condition sensor and providing a detectable signal if the difference meets or exceeds a predetermined value.

In this or another embodiment, the second reagent vessel is configured for containing a liquid composition of a short chain carboxylic acid. The first pretreatment column is configured for removing metal ion from a mixture of the short chain carboxylic acid composition and the oxidizing agent composition. The first reaction catalyst column is configured for catalyzing a reaction of the short chain carboxylic acid and the oxidizing agent to produce short chain peroxycarboxylic acid.

In this embodiment, the third and fourth condition sensors can be configured to measure temperature, pressure, metal content, or combination thereof. For example, the third and fourth condition sensors can be configured to measure temperature.

This or another embodiment can also include a fifth pretreatment column. The fifth pretreatment column can be in fluid communication through the medium reagent conduit with the fourth reagent vessel and the fourth pretreatment column. The fifth pretreatment column can be configured for removing metal ion from the liquid composition of medium chain carboxylic acid. The fifth pretreatment column can include a strong cation exchanger in acid form or in inert metal form.

This or another embodiment can also include a sixth pretreatment column. The sixth pretreatment column can be in fluid communication through the medium reagent conduit with the third reagent vessel and the fourth pretreatment column. The sixth pretreatment column can be configured for removing metal ion from the liquid composition of oxidizing agent. The sixth pretreatment column can include a strong cation exchanger in acid form or in inert metal form.

In this or another embodiment, the reaction catalyst can include a strong acid catalyst that can be physically removed from the reaction mixture; a strong cation exchanger in acid form; or an inorganic compound including an insoluble strong acid.

This embodiment of the apparatus can also include a sixth, a seventh, and an eighth reaction catalyst column. The fifth, sixth, seventh, and eighth reaction catalyst columns can be coupled in series and can be in fluid communication through the medium peracid conduit with the site of storage or use of the medium chain peroxycarboxylic acid composition.

In this embodiment, the peracid vessel can be in fluid communication with the medium peracid conduit and can be configured to receive and contain the medium chain peroxycarboxylic acid composition.

This or another embodiment can also include a second processor. The second processor can be configured for determining a difference between the condition measured by the third condition sensor and the condition measured by the fourth condition sensor and providing a detectable signal if the difference meets or exceeds a predetermined value.

In an embodiment, the first reaction catalyst column has a volume of about 9.6 L. In certain embodiments, each reaction catalyst column has a volume of about 9.6 L. In an embodiment, the fifth reaction catalyst column has a volume of about 9.6 L.

In an embodiment, the first pretreatment column has a volume of about 4.6 L. In an embodiment, the second pretreatment column has a volume of about 4.6 L. In an embodiment, the third pretreatment column has a volume of about 4.6 L. In an embodiment, the fourth pretreatment column has a volume of about 4.6 L. In an embodiment, the fifth pretreatment column has a volume of about 4.6 L. In an embodiment, the sixth pretreatment column has a volume of about 4.6 L.

In an embodiment, the first reagent vessel contains about 35 to about 45 wt-% hydrogen peroxide. In an embodiment, the second reagent vessel contains about 80 to about 98 wt-% acetic acid. In an embodiment, the third reagent vessel contains about 35 to about 45 wt-% hydrogen peroxide. In an embodiment, the second reagent vessel contains about 1 to about 10 wt-% octanoic acid.

The present apparatus can also include a third reagent vessel configured to contain a liquid medium chain carboxylic acid composition and in fluid communication through the reagent conduit with the first pretreatment column. Such an embodiment can also include a fourth pretreatment column. The fourth pretreatment column can be in fluid communication through the reagent conduit with the third reagent vessel and the first pretreatment column. The third reagent vessel can contains about 1 to about 10 wt-% octanoic acid.

The present invention also includes a method for making a peroxycarboxylic acid. This method can include: providing a liquid composition of a carboxylic acid and an oxidizing agent; pretreating the liquid composition with a pretreatment column to remove metal ion from the mixed composition; measuring a condition of the liquid composition i) before pretreating and ii) at site of pretreating during pretreating; determining a difference between i) and ii); providing a detectable signal if the difference meets or exceeds a predetermined value; reacting the pretreated composition in the presence of a reaction catalyst that can be physically removed from reaction mixture to produce a peroxycarboxylic acid composition; and recovering the peroxycarboxylic acid composition.

In an embodiment, pretreating includes contacting the mixed composition and a strong cation exchanger in acid form or in inert metal form.

This method can also include: pretreating a liquid composition of carboxylic acid to remove metal ion from the liquid composition of carboxylic acid; and mixing the pretreated liquid composition of carboxylic acid and oxidizing agent to form the liquid composition of a carboxylic acid and an oxidizing agent. In this embodiment, pretreating can include contacting the liquid composition of carboxylic acid and a strong cation exchanger in acid form or in inert metal form.

This method can also include: pretreating a liquid composition of oxidizing agent to remove metal ion from the liquid composition of oxidizing agent; and mixing the pretreated liquid composition of oxidizing agent and carboxylic acid to form the liquid composition of a carboxylic acid and an oxidizing agent. In this embodiment, pretreating can include contacting the liquid composition of oxidizing agent and a strong cation exchanger in acid form or in inert metal form.

The method can include reacting in a column of insoluble reaction catalyst. This embodiment can also include reacting in a second, a third, and a fourth column of insoluble reaction catalyst. The first, second, third, and fourth reaction catalyst columns can be coupled in series.

In the method, reacting can include contacting the pretreated composition and an insoluble strong acid catalyst. In an embodiment, reacting can include contacting the pretreated composition and a strong cation exchanger in acid form. In an embodiment, reacting can include contacting the pretreated composition and an inorganic compound including an insoluble strong acid.

The method can include measuring temperature, pressure, metal content, or combination thereof of the mixed composition. In an embodiment, the method includes measuring temperature of the mixed composition.

The method can include providing a detectable signal if the temperature difference is greater than 10° C., equal to 10° C., or greater than or equal to 10° C.

The method can also include, if the difference meets or exceeds a predetermined value, interrupting of operation of the apparatus by: actuating a pressure release valve to release pressure in an apparatus carrying out the method; stopping flow of one or more reagents into the apparatus; causing water to flow into the site of pretreating; causing carboxylic acid composition into the site of pretreating; shutting down the apparatus; or a combination thereof.

The method can also include mixing the peroxycarboxylic acid composition and a predetermined amount of carrier to form a diluted composition of a predetermined concentration of peroxycarboxylic acid; storing the diluted composition; monitoring concentration of peroxycarboxylic acid, carboxylic acid, oxidizing agent, or combination thereof in the diluted composition. If the concentration of peroxycarboxylic acid, carboxylic acid, oxidizing agent, or combination thereof is less than a predetermined value, equal to a predetermined value, or less than or equal to a predetermined value, the method can include adding peroxycarboxylic acid composition to the diluted composition.

The method can also include mixing liquid composition of carboxylic acid and oxidizing agent to form the liquid composition of a carboxylic acid and an oxidizing agent. This can form a liquid composition of carboxylic acid that includes about 80 to about 98 wt-% acetic acid. In an embodiment, the oxidizing agent includes about 35 to about 45 wt-% hydrogen peroxide. In an embodiment, the liquid composition of carboxylic acid includes about 1 to about 20 wt-% octanoic acid.

The method can include providing a liquid composition of a plurality of carboxylic acids and an oxidizing agent. In an embodiment, the method can also include mixing a first liquid composition of carboxylic acid, a second liquid composition of carboxylic acid, and oxidizing agent to form the liquid composition of a plurality of carboxylic acids and an oxidizing agent. In an embodiment, the first liquid composition of carboxylic acid includes about 80 to about 98 wt-% acetic acid. In an embodiment, the oxidizing agent includes about 35 to about 45 wt-% hydrogen peroxide. In an embodiment, the second liquid composition of carboxylic acid includes about 1 to about 20 wt-% octanoic acid.

This or another embodiment of the method can also include pretreating a first liquid composition of carboxylic acid to remove metal ion from the first liquid composition of carboxylic acid; and including the pretreated first liquid composition of carboxylic acid in the liquid composition of a plurality of carboxylic acids and an oxidizing agent.

This or another embodiment of the method can also include pretreating a liquid composition of oxidizing agent to remove metal ion from the liquid composition of oxidizing agent; and including the pretreated liquid composition of oxidizing agent in the liquid composition of a plurality of carboxylic acids and an oxidizing agent.

This or another embodiment of the method can also include pretreating a second liquid composition of carboxylic acid to remove metal ion from the second liquid composition of carboxylic acid; and including the pretreated second liquid composition of carboxylic acid in the liquid composition of a plurality of carboxylic acids and an oxidizing agent.

In an embodiment, the liquid composition of a carboxylic acid and an oxidizing agent includes about 40 to about 50 wt-% acetic acid and about 15 to about 25 wt-% hydrogen peroxide. In an embodiment, the liquid composition of a carboxylic acid and an oxidizing agent includes about 25 to about 35 wt-% acetic acid, about 10 to about 20 wt-% hydrogen peroxide, and about 2 to about 4 wt-% octanoic acid.

The method can include carrying out providing, pretreating, measuring, determining, providing, reacting, and recovering at a site at which the peroxycarboxylic acid composition will be used to reduce the population of a microbe on an object. This embodiment of the method can also include delivering carboxylic acid and oxidizing agent to the site. In an embodiment, the method includes delivering a plurality of carboxylic acids to the site. In an embodiment, the method also includes requesting delivery of the carboxylic acid and the oxidizing agent from the site.

In an embodiment, the method also includes applying the peroxycarboxylic acid composition to a beverage container at a beverage plant.

The invention also includes a method for making a peroxycarboxylic acid, including. This method includes delivering carboxylic acid and oxidizing agent to a site at which a peroxycarboxylic acid composition will be made and used; providing a liquid composition of the carboxylic acid and oxidizing agent; pretreating the liquid composition with a pretreatment column to remove metal ion from the mixed composition; reacting the pretreated composition in the presence of a reaction catalyst that can be physically removed from reaction mixture to produce the peroxycarboxylic acid composition; recovering the peroxycarboxylic acid composition; and applying the peroxycarboxylic acid composition to an object to reduce the population of microbe on the object.

In an embodiment, the method includes delivering a plurality of carboxylic acids to the site. In an embodiment, the method also includes requesting delivery of the carboxylic acid and the oxidizing agent from the site.

In an embodiment, the method also includes applying the peroxycarboxylic acid composition to a beverage container at a beverage plant.

The present invention also includes a method for making a mixed peroxycarboxylic acid composition. The method includes providing a liquid composition of a short chain carboxylic acid and an oxidizing agent; pretreating the mixed short chain composition with a pretreatment column to remove metal ion from the short chain mixed composition; reacting the pretreated short chain composition in the presence of an insoluble reaction catalyst to produce a short chain peroxycarboxylic acid composition; providing a liquid composition of a medium chain carboxylic acid and an oxidizing agent; pretreating the mixed medium chain composition with a pretreatment column to remove metal ion from the mixed medium chain composition; reacting the pretreated medium chain composition in the presence of an insoluble reaction catalyst to produce a medium peroxycarboxylic acid composition; mixing the short chain peroxycarboxylic acid composition and the medium chain peroxycarboxylic acid composition to produce a mixed peroxycarboxylic acid composition; measuring a condition of the short chain composition i) before pretreating and ii) at site of pretreating during pretreating; determining a difference between i) and ii); and providing a detectable signal if the difference between i) and ii) meets or exceeds a predetermined value; measuring a condition of the mixed medium chain composition iii) before pretreating and iv) at site of pretreating during pretreating; determining a difference between iii) and iv); and providing a detectable signal if the difference between iii) and iv), or both differences meets or exceeds a predetermined value.

The present invention also includes a peroxycarboxylic acid composition made by a method according to the invention. The method can include providing a liquid composition of a carboxylic acid and an oxidizing agent; pretreating the liquid composition with a pretreatment column to remove metal ion from the mixed composition; measuring a condition of the liquid composition i) before pretreating and ii) at site of pretreating during pretreating; determining a difference between i) and ii); providing a detectable signal if the difference meets or exceeds a predetermined value; reacting the pretreated composition in the presence of an reaction catalyst that can be physically removed from reaction mixture to produce a peroxycarboxylic acid composition; and recovering the peroxycarboxylic acid composition.

The invention includes a peroxycarboxylic acid composition. The composition can include about 1 to about 35 wt-% peroxycarboxylic acid; about 5 to about 30 wt-% hydrogen peroxide; and less than about 10 ppb metal. In an embodiment, the composition retains 85% of the peroxycarboxylic acid for at least about 13 days at 140° F. In an embodiment, the composition retains 95% of the peroxycarboxylic acid for at least about 7 days at 140° F. In an embodiment, the composition includes about 0.5 to about 35 wt-% short chain peroxycarboxylic acid. In an embodiment, the composition includes about 0.5 to about 20 wt-% medium chain peroxycarboxylic acid. In an embodiment, the composition includes about 0.5 to about 35 wt-% short chain peroxycarboxylic acid; and about 0.5 to about 20 wt-% medium chain peroxycarboxylic acid. In an embodiment, the composition includes peroxycarboxylic acid and hydrogen peroxide in a ratio of about 0.5:1 to about 7:1. In an embodiment, the composition includes only volatile compounds.

The present invention also includes a system. The system can include a peroxycarboxylic acid generator that outputs a peroxycarboxylic acid concentrate; a use composition vessel that stores a use composition included of diluted peroxycarboxylic acid concentrate; and a controller that receives concentration data concerning the concentrations of peroxycarboxylic acid and hydrogen peroxide in the use composition and manages replenishing of the use composition when these concentrations do not satisfy predetermined criteria.

In an embodiment, the controller compares the concentration of peroxycarboxylic acid to predetermined POAA target criteria and manages addition of peroxycarboxylic acid concentrate to the use composition when the concentration data indicates that the peroxycarboxylic acid concentration in the use composition is too low.

In an embodiment, the controller compares the concentration of peroxycarboxylic acid to predetermined POAA target criteria and manages addition of diluent to the use composition when the concentration data indicates that the peroxycarboxylic acid concentration in the use composition is too high.

In an embodiment, the controller compares the concentration of hydrogen peroxide to predetermined $H_2O_2$ target criteria and manages emptying of the use composition vessel and production of a new use composition when the concentration data indicates that the hydrogen peroxide concentration in the use composition is too high.

In an embodiment, the controller compares the concentration of peroxycarboxylic acid to an expected POAA target concentration and regulates operating parameters of the peroxycarboxylic acid generator to affect the concentration of peroxycarboxylic acid in the peroxycarboxylic acid concentrate output by the peroxycarboxylic acid generator.

The present invention also includes a method. The method can include receiving concentration data concerning the concentrations of peroxycarboxylic acid and hydrogen peroxide in a use composition; comparing the concentration of peroxycarboxylic acid with predetermined POAA target criteria; and automatically replenishing the use composition when the peroxycarboxylic acid concentration does not satisfy the predetermined POAA target criteria.

In an embodiment of this method, automatically replenishing the use composition also includes automatically adding peroxycarboxylic acid concentrate to the use composition when the concentration data indicates that the peroxycarboxylic acid concentration in the use composition is too low.

In an embodiment of this method, automatically replenishing the use composition also includes automatically adding diluent to the use composition when the concentration data indicates that the peroxycarboxylic acid concentration in the use composition is too high.

In an embodiment of this method, automatically replenishing the use composition also includes automatically emptying the use composition vessel and producing a new use composition when the concentration data indicates that the hydrogen peroxide concentration in the use composition is too high.

In an embodiment, the method also includes comparing the concentration of peroxycarboxylic acid to an expected POAA target concentration and regulating operating parameters of the peroxycarboxylic acid generator to affect the peroxycarboxylic acid concentration in the peroxycarboxylic acid concentrate output by a peroxycarboxylic acid generator.

Carboxylic Acids, Peroxycarboxylic Acids, and Additional Ingredients

Peroxycarboxylic (or percarboxylic) acids generally have the formula $R(CO_3H)_n$, where, for example, R is an alkyl, arylalkyl, cycloalkyl, aromatic, or heterocyclic group, and n is one, two, or three, and named by prefixing the parent acid with peroxy. The R group can be saturated or unsaturated as well as substituted or unsubstituted. Peroxy forms of carboxylic acids with more than one carboxylate moiety can have one or more of the carboxyl moieties present as peroxycarboxyl moieties.

The methods of the invention can employ peroxycarboxylic acids containing, for example, 2 to 12 carbon atoms. For example, peroxycarboxylic (or percarboxylic) acids can have the formula $R(CO_3H)_n$, where R is a $C_1$-$C_{11}$ alkyl group, a $C_1$-$C_{11}$ cycloalkyl, a $C_1$-$C_{11}$ arylalkyl group, $C_1$-$C_{11}$ aryl group, or a $C_1$-$C_{11}$ heterocyclic group; and n is one, two, or three. The methods of the invention can employ a medium chain peroxycarboxylic acid containing, for example, 6 to 12 carbon atoms. For example, medium chain peroxycarboxylic (or percarboxylic) acids can have the formula $R(CO_3H)_n$, where R is a $C_5$-$C_{11}$ alkyl group, a $C_5$-$C_{11}$ cycloalkyl, a $C_5$-$C_{11}$ arylalkyl group, $C_5$-$C_{11}$ aryl group, or a $C_5$-$C_{11}$ heterocyclic group; and n is one, two, or three. The methods of the invention can employ a short chain peroxycarboxylic acid containing, for example, 1 to 4 carbon atoms. For example, short chain peroxycarboxylic (or percarboxylic) acids can have the formula $R(CO_3H)_n$, where R is H, a $C_1$-$C_3$ alkyl group, or a $C_3$ cycloalkyl and n is one or two. The mixed peroxycarboxylic acid composition employed in the present invention can include one or more short chain peroxycarboxylic acids and one or more medium chain peroxycarboxylic acids.

Peroxycarboxylic acids can be made by the direct action of an oxidizing agent on a carboxylic acid, by autoxidation of aldehydes, or from acid chlorides, and hydrides, or carboxylic anhydrides with hydrogen or sodium peroxide. In an embodiment, percarboxylic acid can be made by the direct, acid catalyzed equilibrium action of hydrogen peroxide on the carboxylic acid. Scheme 1 illustrates an equilibrium between carboxylic acid and oxidizing agent (Ox) on one side and peroxycarboxylic acid and reduced oxidizing agent ($Ox_{red}$) on the other:

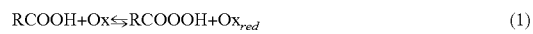

$$RCOOH + Ox \leftrightarrows RCOOOH + Ox_{red} \qquad (1)$$

Scheme 2 illustrates an embodiment of the equilibrium of scheme 1 in which the oxidizing agent is hydrogen peroxide on one side and peroxycarboxylic acid and water on the other:

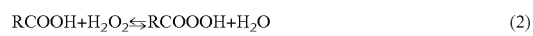

$$RCOOH + H_2O_2 \leftrightarrows RCOOOH + H_2O \qquad (2)$$

In conventional mixed peroxycarboxylic acid compositions it is believed that the equilibrium constant for the reaction illustrated in scheme 2 is about 2.7, which may reflect the equilibrium for acetic acid.

Peroxycarboxylic acids useful in the methods of the present invention include peroxyformic, peroxyacetic, peroxypropionic, peroxybutanoic, peroxypentanoic, peroxyhexanoic, peroxyheptanoic, peroxyoctanoic, peroxynonanoic, peroxydecanoic, peroxyundecanoic, peroxydodecanoic, peroxylactic, peroxymaleic, peroxyascorbic, peroxyhydroxyacetic, peroxyoxalic, peroxymalonic, peroxysuccinic, peroxyglutaric, peroxyadipic, peroxypimelic, peroxysubric acid, or mixtures thereof. Medium chain peroxycarboxylic acids useful in the compositions and methods of the present invention include peroxypentanoic, peroxyhexanoic, peroxyheptanoic, peroxyoctanoic, peroxynonanoic, peroxydecanoic, peroxyundecanoic, peroxydodecanoic, peroxyascorbic, peroxyadipic, peroxycitric, peroxypimelic, or peroxysuberic acid, mixtures thereof, or the like. Short chain peroxycarboxylic acids useful in the compositions and methods of the present invention include peroxyformic, peroxyacetic, peroxypropionic, peroxybutanoic, peroxyoxalic, peroxymalonic, peroxysuccinic acid, mixtures thereof, or the like. The alkyl backbones of these peroxycarboxylic acids can be straight chain, branched, or a mixture thereof. Peroxy forms of carboxylic acids with more than one carboxylate moiety can have one or more (e.g., at least one) of the carboxyl moieties present as peroxycarboxyl moieties.

In an embodiment, the methods of the present invention employ peroxyacetic acid. Peroxyacetic (or peracetic) acid is a peroxycarboxylic acid having the formula: $CH_3COOOH$.

Generally, peroxyacetic acid is a liquid having an acrid odor at higher concentrations and is freely soluble in water, alcohol, ether, and sulfuric acid. A 50% solution of peroxyacetic acid can be obtained by combining acetic anhydride, hydrogen peroxide and sulfuric acid.

Peroxyoctanoic (or peroctanoic) acid is a peroxycarboxylic acid having the formula, for example, of n-peroxyoctanoic acid: $CH_3(CH_2)_6COOOH$. Peroxyoctanoic acid can be an acid with a straight chain alkyl moiety, an acid with a branched alkyl moiety, or a mixture thereof. Peroxyoctanoic acid is surface active and can assist in wetting hydrophobic surfaces, such as those of an arthropod.

In an embodiment, the method of the invention utilizes a combination of several different peroxycarboxylic acids. Such a combination can include one or more short chain, e.g., $C_2$-$C_4$, peroxycarboxylic acids and one or more medium chain, e.g., $C_7$-$C_9$, peroxycarboxylic acids. For example, the short chain peroxycarboxylic acid can be peroxyacetic acid and the medium chain peroxycarboxylic acid can be peroxyoctanoic acid. In an embodiment, the methods of the present invention employ a composition including peroxyoctanoic acid, peroxynonanoic acid, or peroxyheptanoic acid, e.g., peroxyoctanoic acid. In an embodiment, the present method employs a composition including acetic acid, octanoic acid, peroxyacetic acid, and peroxyoctanoic acid. Such a composition can also include a chelating agent.

The present compositions and methods can include a medium chain peroxycarboxylic acid. The medium chain peroxycarboxylic acid can include or be a C6 to C12 peroxycarboxylic acid. The C6 to C12 peroxycarboxylic acid can include or be peroxyhexanoic acid, peroxyheptanoic acid, peroxyoctanoic acid, peroxynonanoic acid, peroxydecanoic acid, peroxyundecanoic acid, peroxydodecanoic acid, or mixture thereof. The medium chain peroxycarboxylic acid can include or be a C7 to C12 peroxycarboxylic acid. The C7 to C12 peroxycarboxylic acid can include or be peroxyheptanoic acid, peroxyoctanoic acid, peroxynonanoic acid, peroxydecanoic acid, peroxyundecanoic acid, peroxydodecanoic acid, or mixture thereof. The medium chain peroxycarboxylic acid can include or be a C6 to C10 peroxycarboxylic acid. The C6 to C10 peroxycarboxylic acid can include or be peroxyhexanoic acid, peroxyheptanoic acid, peroxyoctanoic acid, peroxynonanoic acid, peroxydecanoic acid, or mixture thereof. The medium chain peroxycarboxylic acid can include or be a C8 to C10 peroxycarboxylic acid. The C8 to C10 peroxycarboxylic acid can include or be peroxyoctanoic acid, peroxynonanoic acid, peroxydecanoic acid, or mixture thereof. In certain embodiments, the medium chain peroxyoctanoic acid includes or is peroxyoctanoic acid, peroxydecanoic acid, or mixture thereof. In an embodiment, the medium chain peroxycarboxylic acid includes or is peroxyoctanoic acid.

The composition of the present invention can include a carboxylic acid. Generally, carboxylic acids have the formula R—COOH wherein the R can represent any number of different groups including aliphatic groups, alicyclic groups, aromatic groups, heterocyclic groups, all of which can be saturated or unsaturated as well as substituted or unsubstituted. Carboxylic acids can have one, two, three, or more carboxyl groups. The composition and methods of the invention can employ carboxylic acids containing as many as 18 carbon atoms.

Suitable carboxylic acids include those having one or two carboxyl groups where the R group is a primary alkyl chain having a length of $C_2$ to $C_{12}$. The primary alkyl chain is that carbon chain of the molecule having the greatest length of carbon atoms and directly appending carboxyl functional groups. For example, carboxylic acids can have the formula R—COOH in which R can be a C1-$C_{12}$ alkyl group, a $C_1$-$C_{11}$ cycloalkyl group, a $C_1$-$C_{12}$ arylalkyl group, $C_1$-$C_{11}$ aryl group, or a $C_1$-$C_{11}$ heterocyclic group. The methods of the invention can employ medium chain carboxylic acids containing, for example, 6 to 12 carbon atoms. For example, medium chain carboxylic acids can have the formula R—COOH in which R can be a $C_5$-$C_{11}$ alkyl group, a $C_5$-$C_{11}$ cycloalkyl group, a $C_5$-$C_{11}$ arylalkyl group, $C_5$-$C_{11}$ aryl group, or a $C_5$-$C_{11}$ heterocyclic group. For example, short chain carboxylic acids can have the formula R—COOH in which R is H, a $C_1$-$C_3$ alkyl group, or a $C_3$ cycloalkyl and n is one or two.

Suitable carboxylic acids include formic, acetic, propionic, butanoic, pentanoic, hexanoic, heptanoic, octanoic, nonanoic, decanoic, undecanoic, dodecanoic, lactic, maleic, ascorbic, citric, hydroxyacetic, neopentanoic, neoheptanoic, neodecanoic, oxalic, malonic, succinic, glutaric, adipic, pimelic, subric acid, mixtures thereof, or the like. Suitable medium chain carboxylic acids include pentanoic, hexanoic, heptanoic, octanoic, nonanoic, decanoic, undecanoic, dodecanoic, ascorbic, citric, adipic, pimelic, suberic acid, mixtures thereof, or the like. Suitable short chain carboxylic acids include formic, acetic, propionic, butanoic, hydroxyacetic, oxalic, malonic, succinic acid, mixtures thereof, or the like. The alkyl backbones of these carboxylic acids can be straight chain, branched, or a mixture thereof. Carboxylic acids which are generally useful are those having one or two carboxyl groups where the R group is a primary alkyl chain having a length of $C_4$ to $C_{11}$. The primary alkyl chain is that carbon chain of the molecule having the greatest length of carbon atoms and directly appending carboxyl functional groups.

In an embodiment, the present compositions and methods include a medium chain carboxylic acid. The medium chain carboxylic acid can include or be a C6 to C12 carboxylic acid. The C6 to C12 carboxylic acid can include or be hexanoic acid, heptanoic acid, octanoic acid, nonanoic acid, decanoic acid, undecanoic acid, dodecanoic acid, or mixture thereof. The medium chain carboxylic acid can include or be a C7 to C12 carboxylic acid. The C7 to C12 carboxylic acid can include or be heptanoic acid, octanoic acid, nonanoic acid, decanoic acid, undecanoic acid, dodecanoic acid, or mixture thereof. The medium chain peroxycarboxylic acid can include or be a C6 to C10 carboxylic acid. The C6 to C10 carboxylic acid can include or be hexanoic acid, heptanoic acid, octanoic acid, nonanoic acid, decanoic acid, or mixture thereof. The medium chain carboxylic acid can include or be a C8 to C10 carboxylic acid. The C8 to C10 carboxylic acid can include or be octanoic acid, nonanoic acid, decanoic acid, or mixture thereof. In certain embodiments, the medium chain carboxylic acid includes or is octanoic acid, decanoic acid, or mixture thereof. In an embodiment, the medium chain carboxylic acid includes or is octanoic acid.

In an embodiment, the compositions and methods include mixed peroxycarboxylic acids and the corresponding mixed carboxylic acids.

In an embodiment, the present composition includes an amount of mixed peroxycarboxylic acid effective for killing one or more (e.g., at least one) of the food-borne pathogenic bacteria associated with a food product, such as *Salmonella typhimurium, Salmonella javiana, Campylobacter jejuni, Listeria monocytogenes,* and *Escherichia coli* O157:H7, yeast, mold, and the like. In an embodiment, the present composition includes an amount of mixed peroxycarboxylic acid effective for killing one or more (e.g., at least one) of the pathogenic bacteria associated with a health care surfaces and environments, such as *Salmonella typhimurium, Staphylo-* coccus aureus, Salmonella choleraesurus, Pseudomonas aeruginosa, Escherichia coli, mycobacteria, yeast, mold, and the like. The compositions and methods of the present invention have activity against a wide variety of microorganisms such as Gram positive (for example, Listeria monocytogenes or Staphylococcus aureus) and Gram negative (for example, Escherichia coli or Pseudomonas aeruginosa) bacteria, yeast, molds, bacterial spores, viruses, etc. The compositions and methods of the present invention, as described above, have activity against a wide variety of human pathogens. The present compositions and methods can kill a wide variety of microorganisms on a food processing surface, on the surface of a food product, in water used for washing or processing of food product, on a health care surface, or in a health care environment.

Carrier

The composition of the invention can also include a carrier. The carrier provides a medium which dissolves, suspends, or carries the other components of the composition. For example, the carrier can provide a medium for solubilization, suspension, or production of peroxycarboxylic acid and for forming an equilibrium mixture. The carrier can also function to deliver and wet the antimicrobial composition of the invention on an object. To this end, the carrier can contain any component or components that can facilitate these functions.

Generally, the carrier includes primarily water which can promote solubility and work as a medium for reaction and equilibrium. The carrier can include or be primarily an organic solvent, such as simple alkyl alcohols, e.g., ethanol, isopropanol, n-propanol, and the like. Polyols are also useful carriers, including glycerol, sorbitol, and the like.

Suitable carriers include glycol ethers. Suitable glycol ethers include diethylene glycol n-butyl ether, diethylene glycol n-propyl ether, diethylene glycol ethyl ether, diethylene glycol methyl ether, diethylene glycol t-butyl ether, dipropylene glycol n-butyl ether, dipropylene glycol methyl ether, dipropylene glycol ethyl ether, dipropylene glycol propyl ether, dipropylene glycol tert-butyl ether, ethylene glycol butyl ether, ethylene glycol propyl ether, ethylene glycol ethyl ether, ethylene glycol methyl ether, ethylene glycol methyl ether acetate, propylene glycol n-butyl ether, propylene glycol ethyl ether, propylene glycol methyl ether, propylene glycol n-propyl ether, tripropylene glycol methyl ether and tripropylene glycol n-butyl ether, ethylene glycol phenyl ether (commercially available as DOWANOL EPH™ from Dow Chemical Co.), propylene glycol phenyl ether (commercially available as DOWANOL PPH™ from Dow Chemical Co.), and the like, or mixtures thereof. Additional suitable commercially available glycol ethers (all of which are available from Union Carbide Corp.) include Butoxyethyl PROPASOL™, Butyl CARBITOL™ acetate, Butyl CARBITOL™, Butyl CELLOSOLVE™ acetate, Butyl CELLOSOLVE™, Butyl DIPROPASOL™, Butyl PROPASOL™, CARBITOL™ PM-600, CARBITOL™ Low Gravity, CELLOSOLVE™ acetate, CELLOSOLVE™, Ester EEP™, FILMER IBT™, Hexyl CARBITOL™, Hexyl CELLOSOLVE™, Methyl CARBITOL™, Methyl CELLOSOLVE™ acetate, Methyl CELLOSOLVE™, Methyl DIPROPASOL™, Methyl PROPASOL™ acetate, Methyl PROPASOL™, Propyl CARBITOL™, Propyl CELLOSOLVE™, Propyl DIPROPASOL™ and Propyl PROPASOL™.

Generally, the carrier makes up a large portion of the composition of the invention and may be the balance of the composition apart from the active antimicrobial components, solubilizer, oxidizing agent, adjuvants, and the like. Here again, the carrier concentration and type will depend upon the nature of the composition as a whole, the environmental storage, and method of application including concentration of the peroxycarboxylic acid, among other factors. Notably the carrier should be chosen and used at a concentration which does not inhibit the antimicrobial efficacy of the peroxycarboxylic acid in the composition of the invention.

In certain embodiments, the present composition includes about 0 to about 98 wt-% carrier, about 0.001 to about 99.99 wt-% carrier, about 0.2 to about 60 wt-% carrier, about 1 to about 98 wt-% carrier, about 5 to about 99.99 wt-% carrier, about 5 to about 97 wt-% carrier, about 5 to about 90 wt-% carrier, about 5 to about 70 wt-% carrier, about 5 to about 20 wt-% carrier, about 10 to about 90 wt-% carrier, about 10 to about 80 wt-% carrier, about 10 to about 50 wt-% carrier, about 10 to about 20 wt-% carrier, about 15 to about 70 wt-% carrier, about 15 to about 80 wt-% carrier, about 20 to about 70 wt-% carrier, about 20 to about 50 wt-% carrier, about 20 to about 40 wt-% carrier, about 20 to about 30 wt-% carrier, about 30 to about 75 wt-% carrier, about 30 to about 70 wt-% carrier, about 40 to about 99.99 wt-% carrier, about 40 to about 90 wt-% carrier, or about 60 to about 70 wt-% carrier. The composition can include any of these ranges or amounts not modified by about.

Oxidizing Agent

The present compositions and methods can include any of a variety of oxidizing agents. The oxidizing agent can be used for maintaining or generating peroxycarboxylic acids.

Examples of inorganic oxidizing agents include the following types of compounds or sources of these compounds, or alkali metal salts including these types of compounds, or forming an adduct therewith:

hydrogen peroxide;

group 1 (IA) oxidizing agents, for example lithium peroxide, sodium peroxide, and the like;

group 2 (IIA) oxidizing agents, for example magnesium peroxide, calcium peroxide, strontium peroxide, barium peroxide, and the like;

group 12 (IIB) oxidizing agents, for example zinc peroxide, and the like;

group 13 (IIIA) oxidizing agents, for example boron compounds, such as perborates, for example sodium perborate hexahydrate of the formula $Na_2[Br_2(O_2)_2(OH)_4] \cdot 6H_2O$ (also called sodium perborate tetrahydrate and formerly written as $NaBO_3 \cdot 4H_2O$); sodium peroxyborate tetrahydrate of the formula $Na_2Br_2(O_2)_2[(OH)_4] \cdot 4H_2O$ (also called sodium perborate trihydrate, and formerly written as $NaBO_3 \cdot 3H_2O$); sodium peroxyborate of the formula $Na_2[B_2(O_2)_2(OH)_4]$ (also called sodium perborate monohydrate and formerly written as $NaBO_3 \cdot H_2O$); and the like; in an embodiment, perborate;

group 14 (IVA) oxidizing agents, for example persilicates and peroxycarbonates, which are also called percarbonates, such as persilicates or peroxycarbonates of alkali metals; and the like; in an embodiment, percarbonate; in an embodiment, persilicate;

group 15 (VA) oxidizing agents, for example peroxynitrous acid and its salts; peroxyphosphoric acids and their salts, for example, perphosphates; and the like; in an embodiment, perphosphate;

group 16 (VIA) oxidizing agents, for example peroxysulfuric acids and their salts, such as peroxymonosulfuric and peroxydisulfuric acids, and their salts, such as persulfates, for example, sodium persulfate; and the like; in an embodiment, persulfate;

group VIIa oxidizing agents such as sodium periodate, potassium perchlorate and the like.

Other active inorganic oxygen compounds can include transition metal peroxides; and other such peroxygen compounds, and mixtures thereof.

In an embodiment, the compositions and methods of the present invention employ one or more of the inorganic oxidizing agents listed above. Suitable inorganic oxidizing agents include ozone, hydrogen peroxide, hydrogen peroxide adduct, group IIIA oxidizing agent, group VIA oxidizing agent, group VA oxidizing agent, group VIIA oxidizing agent, or mixtures thereof. Suitable examples of such inorganic oxidizing agents include percarbonate, perborate, persulfate, perphosphate, persilicate, or mixtures thereof.

Hydrogen peroxide presents one suitable example of an inorganic oxidizing agent. Hydrogen peroxide can be provided as a mixture of hydrogen peroxide and water, e.g., as liquid hydrogen peroxide in an aqueous solution. Hydrogen peroxide is commercially available at concentrations of 35%, 70%, and 90% in water. For safety, the 35% is commonly used. The present compositions can include, for example, about 2 to about 30 wt-% or about 5 to about 20 wt-% hydrogen peroxide.

In an embodiment, the inorganic oxidizing agent includes hydrogen peroxide adduct. For example, the inorganic oxidizing agent can include hydrogen peroxide, hydrogen peroxide adduct, or mixtures thereof. Any of a variety of hydrogen peroxide adducts are suitable for use in the present compositions and methods. For example, suitable hydrogen peroxide adducts include percarbonate salt, urea peroxide, peracetyl borate, an adduct of $H_2O_2$ and polyvinyl pyrrolidone, sodium percarbonate, potassium percarbonate, mixtures thereof, or the like. Suitable hydrogen peroxide adducts include percarbonate salt, urea peroxide, peracetyl borate, an adduct of $H_2O_2$ and polyvinyl pyrrolidone, or mixtures thereof. Suitable hydrogen peroxide adducts include sodium percarbonate, potassium percarbonate, or mixtures thereof, for example sodium percarbonate.

In an embodiment, the present compositions and methods can include hydrogen peroxide as oxidizing agent. Hydrogen peroxide in combination with the percarboxylic acid can provide certain antimicrobial action against microorganisms. Additionally, hydrogen peroxide can provide an effervescent action which can irrigate any surface to which it is applied. Hydrogen peroxide can work with a mechanical flushing action once applied which further cleans the surface of an object. An additional advantage of hydrogen peroxide is the food compatibility of this composition upon use and decomposition.

In certain embodiments, the present composition includes about 0.001 to about 30 wt-% oxidizing agent, about 0.001 to about 10 wt-% oxidizing agent, 0.002 to about 10 wt-% oxidizing agent, about 2 to about 30 wt-% oxidizing agent, about 2 to about 25 wt-% oxidizing agent, about 2 to about 20 wt-% oxidizing agent, about 4 to about 20 wt-% oxidizing agent, about 5 to about 10 wt-% oxidizing agent, or about 6 to about 10 wt-% oxidizing agent. The composition can include any of these ranges or amounts not modified by about.

Optional Ingredients
Acidulant

In an embodiment, the present composition can include an acidulant. The acidulant can act as a catalyst for conversion of carboxylic acid to peroxycarboxylic acid. The acidulant can be effective to form a concentrate composition with pH of about 1 or less. The acidulant can be effective to form a use composition with pH of about 5, about 5 or less, about 4, about 4 or less, about 3, about 3 or less, about 2, about 2 or less, or the like. In an embodiment, the acidulant includes an inorganic acid. Suitable inorganic acids include sulfuric acid, phosphoric acid, nitric acid, hydrochloric acid, methane sulfonic acid, ethane sulfonic acid, propane sulfonic acid, butane sulfonic acid, xylene sulfonic acid, benzene sulfonic acid, mixtures thereof, or the like.

In an embodiment, the acidulant includes a carboxylic acid with $pK_a$ less than 4. Suitable carboxylic acids with $pK_a$ less than 4 include hydroxyacetic acid, hydroxypropionic acid, other hydroxycarboxylic acids, mixtures thereof, or the like. Such an acidulant is present at a concentration where it does not act as a solubilizer.

In certain embodiments, the present composition includes about 0.001 to about 50 wt-% acidulant, about 0.001 to about 30 wt-% acidulant, about 1 to about 50 wt-% acidulant, about 1 to about 30 wt-% acidulant, about 2 to about 40 wt-% acidulant, about 2 to about 10 wt-% acidulant, about 3 to about 40 wt-% acidulant, about 5 to about 40 wt-% acidulant, about 5 to about 25 wt-% acidulant, about 10 to about 40 wt-% acidulant, about 10 to about 30 wt-% acidulant, about 15 to about 35 wt-% acidulant, about 15 to about 30 wt-% acidulant, or about 40 to about 60 wt-% acidulant. The composition can include any of these ranges or amounts not modified by about.

Stabilizing Agent

One or more stabilizing agents can be added to the composition of the invention, for example, to stabilize the peracid and hydrogen peroxide and prevent the premature oxidation of this constituent within the composition of the invention.

Suitable stabilizing agents include chelating agents or sequestrants. Suitable sequestrants include organic chelating compounds that sequester metal ions in solution, particularly transition metal ions. Such sequestrants include organic amino- or hydroxy-polyphosphonic acid complexing agents (either in acid or soluble salt forms), carboxylic acids (e.g., polymeric polycarboxylate), hydroxycarboxylic acids, or aminocarboxylic acids.

The sequestrant can be or include phosphonic acid or phosphonate salt. Suitable phosphonic acids and phosphonate salts include 1-hydroxy ethylidene-1,1-diphosphonic acid $(CH_3C(PO_3H_2)_2OH)$ (HEDP); ethylenediamine tetrakis methylenephosphonic acid (EDTMP); diethylenetriamine pentakis methylenephosphonic acid (DTPMP); cyclohexane-1,2-tetramethylene phosphonic acid; amino[tri(methylene phosphonic acid)]; (ethylene diamine[tetra methylene-phosphonic acid)]; 2-phosphene butane-1,2,4-tricarboxylic acid; or salts thereof, such as the alkali metal salts, ammonium salts, or alkyloyl amine salts, such as mono, di, or tetra-ethanolamine salts; or mixtures thereof.

Suitable organic phosphonates include HEDP.

Commercially available food additive chelating agents include phosphonates sold under the trade name DEQUEST® including, for example, 1-hydroxyethylidene-1,1-diphosphonic acid, available from Monsanto Industrial Chemicals Co., St. Louis, Mo., as DEQUEST® 2010; amino (tri(methylenephosphonic acid)), $(N[CH_2PO_3H_2]_3)$, available from Monsanto as DEQUEST® 2000; ethylenediamine [tetra(methylenephosphonic acid)] available from Monsanto as DEQUEST® 2041; and 2-phosphonobutane-1,2,4-tricarboxylic acid available from Mobay Chemical Corporation, Inorganic Chemicals Division, Pittsburgh, Pa., as Bayhibit AM.

The sequestrant can be or include aminocarboxylic acid type sequestrant. Suitable aminocarboxylic acid type sequestrants include the acids or alkali metal salts thereof, e.g., amino acetates and salts thereof. Suitable aminocarboxylates include N-hydroxyethylaminodiacetic acid; hydroxyethylenediaminetetraacetic acid, nitrilotriacetic acid (NTA); ethylenediaminetetraacetic acid (EDTA); N-hydroxyethylethylenediaminetriacetic acid (HEDTA); diethylenetriaminepentaacetic acid (DTPA); and alanine-N,N-diacetic acid; and the like; and mixtures thereof.

The sequestrant can be or include a polycarboxylate. Suitable polycarboxylates include, for example, polyacrylic acid, maleic/olefin copolymer, acrylic/maleic copolymer, polymethacrylic acid, acrylic acid-methacrylic acid copolymers, hydrolyzed polyacrylamide, hydrolyzed polymethacrylamide, hydrolyzed polyamide-methacrylamide copolymers, hydrolyzed polyacrylonitrile, hydrolyzed polymethacrylonitrile, hydrolyzed acrylonitrile-methacrylonitrile copolymers, polymaleic acid, polyfumaric acid, copolymers of acrylic and itaconic acid, phosphino polycarboxylate, acid or salt forms thereof, mixtures thereof, and the like.

In certain embodiments, the present composition includes about 0.5 to about 50 wt-% sequestrant, about 1 to about 50 wt-% sequestrant, about 1 to about 30 wt-% sequestrant, about 1 to about 15 wt-% sequestrant, about 1 to about 5 wt-% sequestrant, about 1 to about 4 wt-% sequestrant, about 2 to about 10 wt-% sequestrant, about 2 to about 5 wt-% sequestrant, or about 5 to about 15 wt-% sequestrant. The composition can include any of these ranges or amounts not modified by about.

In certain embodiments, the present composition includes about 0.001 to about 50 wt-% stabilizing agent, about 0.001 to about 5 wt-% stabilizing agent, about 0.5 to about 50 wt-% stabilizing agent, about 1 to about 50 wt-% stabilizing agent, about 1 to about 30 wt-% stabilizing agent, about 1 to about 10 wt-% stabilizing agent, about 1 to about 5 wt-% stabilizing agent, about 1 to about 3 wt-% stabilizing agent, about 2 to about 10 wt-% stabilizing agent, about 2 to about 5 wt-% stabilizing agent, or about 5 to about 15 wt-% stabilizing agent. The composition can include any of these ranges or amounts not modified by about.

Surfactants
Nonionic Surfactants

Suitable nonionic surfactants for use as solvents include alkoxylated surfactants. Suitable alkoxylated surfactants include EO/PO copolymers, capped EO/PO copolymers, alcohol alkoxylates, capped alcohol alkoxylates, mixtures thereof, or the like. Suitable alkoxylated surfactants for use as solvents include EO/PO block copolymers, such as the Pluronic and reverse Pluronic surfactants; alcohol alkoxylates, such as Dehypon LS-54 (R-(EO)$_5$(PO)$_4$) and Dehypon LS-36 (R-(EO)$_3$(PO)$_6$); and capped alcohol alkoxylates, such as Plurafac LF221 and Tegoten EC11; mixtures thereof, or the like. When employed as a solvent a surfactant, such as a nonionic surfactant, can be at concentrations higher than those conventionally employed as surfactant.

Semi-Polar Nonionic Surfactants

The semi-polar type of nonionic surface active agents are another class of nonionic surfactant useful in compositions of the present invention. Semi-polar nonionic surfactants include the amine oxides, phosphine oxides, sulfoxides and their alkoxylated derivatives.

Amine oxides are tertiary amine oxides corresponding to the general formula:

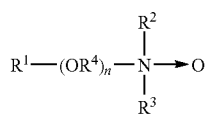

wherein the arrow is a conventional representation of a semi-polar bond; and, $R^1$, $R^2$, and $R^3$ may be aliphatic, aromatic, heterocyclic, alicyclic, or combinations thereof. Generally, for amine oxides of detergent interest, $R^1$ is an alkyl radical of from about 8 to about 24 carbon atoms; $R^2$ and $R^3$ are alkyl or hydroxyalkyl of 1-3 carbon atoms or a mixture thereof, $R^2$ and $R^3$ can be attached to each other, e.g. through an oxygen or nitrogen atom, to form a ring structure; $R^4$ is an alkylene or a hydroxyalkylene group containing 2 to 3 carbon atoms; and n ranges from 0 to about 20. An amine oxide can be generated from the corresponding amine and an oxidizing agent, such as hydrogen peroxide.

Useful water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylaine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

Anionic Surfactants

The present composition can include an anionic surfactant as solubilizer. Suitable anionic surfactants include organic sulfonate surfactant, organic sulfate surfactant, phosphate ester surfactant, carboxylate surfactant, mixtures thereof, or the like. In an embodiment, the anionic surfactant includes alkyl sulfonate, alkylaryl sulfonate, alkylated diphenyl oxide disulfonate, alkylated naphthalene sulfonate, alcohol alkoxylate carboxylate, sarcosinate, taurate, acyl amino acid, alkanoic ester, phosphate ester, sulfuric acid ester, salt or acid form thereof, or mixture thereof. The particular salts will be suitably selected depending upon the particular formulation and the needs therein.

Suitable anionic surfactants include sulfonic acids (and salts), such as isethionates (e.g. acyl isethionates), alkylaryl sulfonic acids and salts thereof, alkyl sulfonates, and the like.

Examples of suitable synthetic, water soluble anionic detergent compounds include the ammonium and substituted ammonium (such as mono-, di- and triethanolamine) and alkali metal (such as sodium, lithium and potassium) salts of the alkyl mononuclear aromatic sulfonates such as the alkyl benzene sulfonates containing from about 5 to about 18 carbon atoms in the alkyl group in a straight or branched chain, e.g., the salts of alkyl benzene sulfonates or of alkyl toluene, xylene, cumene and phenol sulfonates; alkyl naphthalene sulfonate, diamyl naphthalene sulfonate, and dinonyl naphthalene sulfonate and alkoxylated derivatives or their free acids. Suitable sulfonates include olefin sulfonates, such as long chain alkene sulfonates, long chain hydroxyalkane sulfonates or mixtures of alkenesulfonates and hydroxyalkanesulfonates.

In certain embodiments, the present compositions including an anionic surfactant, such as a normal C8 sulfonate, can be non-foam or low foam compositions. Such compositions can be advantageous for applications such as clean in place, machine warewashing, destaining, and sanitizing, laundry washing, destaining, and sanitizing, etc.

For applications in which foaming is desirable, a foaming agent can be added as part of the present composition or separately. In a two-step offering, a foaming agent can be combined with a dilution of the non-foam or low foam composition to form a foaming use solution. In a one-step offering, the foaming agent can be incorporated into the concentrated composition. One suitable foaming agent is LAS acid. LAS acid can form a microemulsion in the present compositions. LAS acid can form a viscoelastic gel or liquid in the present compositions.

Anionic sulfate surfactants suitable for use in the present compositions include alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, the $C_5$-$C_{17}$ acyl-N—($C_1$-$C_4$ alkyl) and —N—($C_1$-$C_2$ hydroxyalkyl) glucamine sulfates, and sulfates of alkylpolysaccharides such as the sulfates of alkylpolyglucoside, and the like. Also included are the alkyl sulfates, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic carboxylate surfactants suitable for use in the present compositions include carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylgluamates, acyl peptides, sarcosinates (e.g. N-acyl sarcosinates), taurates (e.g. N-acyl taurates and fatty acid amides of methyl tauride), and the like.

Suitable anionic surfactants include alkyl or alkylaryl ethoxy carboxylates of Formula 3:

$$R—O—(CH_2CH_2O)_n(CH_2)_m—CO_2X \quad (3)$$

in which R is a $C_8$ to $C_{22}$ alkyl group or

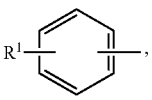

in which $R^1$ is a $C_4$-$C_{16}$ alkyl group; n is an integer of 1-20; m is an integer of 1-3; and X is a counter ion, such as hydrogen, sodium, potassium, lithium, ammonium, or an amine salt such as monoethanolamine, diethanolamine or triethanolamine. In an embodiment, in Formula 3, n is an integer of 4 to 10 and m is 1. In an embodiment, in Formula 3, R is a $C_8$-$C_{16}$ alkyl group. In an embodiment, in Formula 3, R is a $C_{12}$-$C_{14}$ alkyl group, n is 4, and m is 1.

In an embodiment, in Formula 3, R is

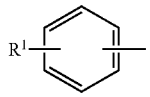

and $R^1$ is a $C_6$-$C_{12}$ alkyl group. In an embodiment, in Formula 3, $R^1$ is a $C_9$ alkyl group, n is 10 and m is 1. Such alkyl and alkylaryl ethoxy carboxylates are commercially available. These ethoxy carboxylates are typically available as the acid forms, which can be readily converted to the anionic or salt form. Commercially available carboxylates include, Neodox 23-4, a $C_{12-13}$ alkyl polyethoxy (4) carboxylic acid (Shell Chemical), and Emcol CNP-110, a $C_9$ alkylaryl polyethoxy (10) carboxylic acid (Witco Chemical). Carboxylates are also available from Clariant, e.g. the product Sandopan® DTC, a $C_{13}$ alkyl polyethoxy (7) carboxylic acid.

Amphoteric Surfactants

Amphoteric, or ampholytic, surfactants contain both a basic and an acidic hydrophilic group and an organic hydrophobic group. These ionic entities may be any of anionic or cationic groups described herein for other types of surfactants. A basic nitrogen and an acidic carboxylate group are the typical functional groups employed as the basic and acidic hydrophilic groups. In a few surfactants, sulfonate, sulfate, phosphonate or phosphate provide the negative charge.

Amphoteric surfactants can be broadly described as derivatives of aliphatic secondary and tertiary amines, in which the aliphatic radical may be straight chain or branched and wherein one of the aliphatic substituents contains from about 8 to 18 carbon atoms and one contains an anionic water solubilizing group, e.g., carboxy, sulfo, sulfato, phosphato, or phosphono. Amphoteric surfactants are subdivided into two major classes known to those of skill in the art and described in "Surfactant Encyclopedia" *Cosmetics & Toiletries*, Vol. 104 (2) 69-71 (1989). The first class includes acyl/dialkyl ethylenediamine derivatives (e.g. 2-alkyl hydroxyethyl imidazoline derivatives) and their salts. The second class includes N-alkylamino acids and their salts. Some amphoteric surfactants can be envisioned as fitting into both classes.

Amphoteric surfactants can be synthesized by methods known to those of skill in the art. For example, 2-alkyl hydroxyethyl imidazoline is synthesized by condensation and ring closure of a long chain carboxylic acid (or a derivative) with dialkyl ethylenediamine. Commercial amphoteric surfactants are derivatized by subsequent hydrolysis and ring-opening of the imidazoline ring by alkylation—for example with chloroacetic acid or ethyl acetate. During alkylation, one or two carboxy-alkyl groups react to form a tertiary amine and an ether linkage with differing alkylating agents yielding different tertiary amines.

Long chain imidazole derivatives having application in the present invention generally have the general formula:

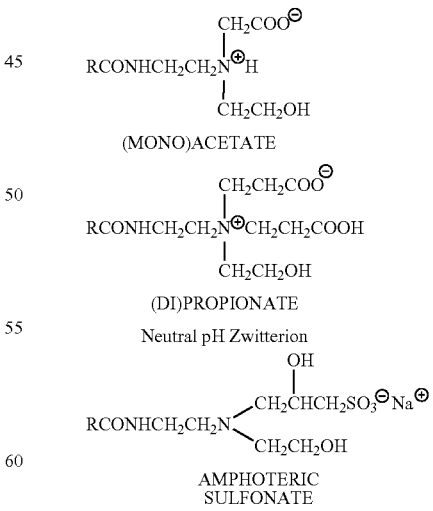

wherein R is an acyclic hydrophobic group containing from about 8 to 18 carbon atoms and M is a cation to neutralize the charge of the anion, generally sodium. Commercially prominent imidazoline-derived amphoterics that can be employed in the present compositions include for example: Cocoamphopropionate, Cocoamphocarboxy-propionate, Cocoamphoglycinate, Cocoamphocarboxy-glycinate, Cocoamphopropyl-sulfonate, and Cocoamphocarboxy-propionic acid. Amphocarboxylic acids can be produced from fatty imidazolines in which the dicarboxylic acid functionality of the amphodicarboxylic acid is diacetic acid and/or dipropionic acid.

The carboxymethylated compounds (glycinates) described herein above frequently are called betaines. Betaines are a special class of amphoteric discussed herein below in the section entitled, Zwitterion Surfactants.

Long chain N-alkylamino acids are readily prepared by reaction $RNH_2$, in which $R = C_8-C_{18}$ straight or branched chain alkyl, fatty amines with halogenated carboxylic acids. Alkylation of the primary amino groups of an amino acid leads to secondary and tertiary amines. Alkyl substituents may have additional amino groups that provide more than one reactive nitrogen center. Most commercial N-alkylamine acids are alkyl derivatives of beta-alanine or beta-N(2-carboxyethyl) alanine. Examples of commercial N-alkylamino acid ampholytes having application in this invention include alkyl beta-amino dipropionates, $RN(C_2H_4COOM)_2$ and $RNHC_2H_4COOM$. In an embodiment, R can be an acyclic hydrophobic group containing from about 8 to about 18 carbon atoms, and M is a cation to neutralize the charge of the anion.

Suitable amphoteric surfactants include those derived from coconut products such as coconut oil or coconut fatty acid. Additional suitable coconut derived surfactants include as part of their structure an ethylenediamine moiety, an alkanolamide moiety, an amino acid moiety, e.g., glycine, or a combination thereof, and an aliphatic substituent of from about 8 to 18 (e.g., 12) carbon atoms. Such a surfactant can also be considered an alkyl amphodicarboxylic acid. These amphoteric surfactants can include chemical structures represented as: $C_{12}$-alkyl-C(O)—NH—$CH_2$—$CH_2$—$N^+(CH_2$—$CH_2$—$CO_2Na)_2$—$CH_2$—$CH_2$—OH or $C_{12}$-alkyl-C(O)—N(H)—$CH_2$—$CH_2$—$N^+(CH_2$—$CO_2Na)_2$—$CH_2$—$CH_2$—OH. Disodium cocoampho dipropionate is one suitable amphoteric surfactant and is commercially available under the tradename Miranol™ FBS from Rhodia Inc., Cranbury, N.J. Another suitable coconut derived amphoteric surfactant with the chemical name disodium cocoampho diacetate is sold under the tradename Mirataine™ JCHA, also from Rhodia Inc., Cranbury, N.J.

A typical listing of amphoteric classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

Zwitterionic Surfactants

Zwitterionic surfactants can be thought of as a subset of the amphoteric surfactants and can include an anionic charge. Zwitterionic surfactants can be broadly described as derivatives of secondary and tertiary amines, derivatives of heterocyclic secondary and tertiary amines, or derivatives of quaternary ammonium, quaternary phosphonium or tertiary sulfonium compounds. Typically, a zwitterionic surfactant includes a positive charged quaternary ammonium or, in some cases, a sulfonium or phosphonium ion; a negative charged carboxyl group; and an alkyl group. Zwitterionics generally contain cationic and anionic groups which ionize to a nearly equal degree in the isoelectric region of the molecule and which can develop strong "inner-salt" attraction between positive-negative charge centers. Examples of such zwitterionic synthetic surfactants include derivatives of aliphatic quaternary ammonium, phosphonium, and sulfonium compounds, in which the aliphatic radicals can be straight chain or branched, and wherein one of the aliphatic substituents contains from 8 to 18 carbon atoms and one contains an anionic water solubilizing group, e.g., carboxy, sulfonate, sulfate, phosphate, or phosphonate. Betaine and sultaine surfactants are exemplary zwitterionic surfactants for use herein.

A general formula for these compounds is:

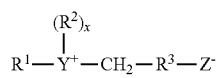

wherein $R^1$ contains an alkyl, alkenyl, or hydroxyalkyl radical of from 8 to 18 carbon atoms having from 0 to 10 ethylene oxide moieties and from 0 to 1 glyceryl moiety; Y is selected from the group consisting of nitrogen, phosphorus, and sulfur atoms; $R^2$ is an alkyl or monohydroxy alkyl group containing 1 to 3 carbon atoms; x is 1 when Y is a sulfur atom and 2 when Y is a nitrogen or phosphorus atom, $R^3$ is an alkylene or hydroxy alkylene or hydroxy alkylene of from 1 to 4 carbon atoms and Z is a radical selected from the group consisting of carboxylate, sulfonate, sulfate, phosphonate, and phosphate groups.

Examples of zwitterionic surfactants having the structures listed above include: 4-[N,N-di(2-hydroxyethyl)-N-octadecylammonio]-butane-1-carboxylate; 5-[S-3-hydroxypropyl-5-hexadecylsulfonio]-3-hydroxypentane-1-sulfate; 3-[P,P-diethyl-P-3,6,9-trioxatetracosanephosphonio]-2-hydroxypropane-1-phosphate; 3-[N,N-dipropyl-N-3-dodecoxy-2-hydroxypropyl-ammonio]-propane-1-phosphonate; 3-(N,N-dimethyl-N-hexadecylammonio)-propane-1-sulfonate; 3-(N,N-dimethyl-N-hexadecylammonio)-2-hydroxy-propane-1-sulfonate; 4-[N,N-di(2(2-hydroxyethyl)-N(2-hydroxydodecyl)ammonio]-butane-1-carboxylate; 3-[S-ethyl-S-(3-dodecoxy-2-hydroxypropyl)sulfonio]-propane-1-phosphate; 3-[P,P-dimethyl-P-dodecylphosphonio]-propane-1-phosphonate; and S[N,N-di(3-hydroxypropyl)-N-hexadecylammonio]-2-hydroxy-pentane-1-sulfate. The alkyl groups contained in said detergent surfactants can be straight or branched and saturated or unsaturated.

The zwitterionic surfactant suitable for use in the present compositions includes a betaine of the general structure:

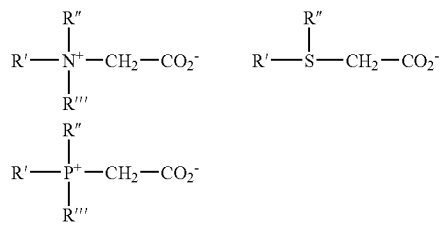

These surfactant betaines typically do not exhibit strong cationic or anionic characters at pH extremes nor do they show reduced water solubility in their isoelectric range. Unlike "external" quaternary ammonium salts, betaines are compatible with anionics. Examples of suitable betaines include coconut acylamidopropyldimethyl betaine; hexadecyl dimethyl betaine; $C_{12-14}$ acylamidopropylbetaine; $C_{8-14}$ acylamidohexyldiethyl betaine; 4-$C_{14-16}$ acylmethylamidodiethylammonio-1-carboxybutane; $C_{16-18}$ acylamidodimethylbetaine; $C_{12-16}$ acylamidopentanediethylbetaine; and $C_{12-16}$ acylmethylamidodimethylbetaine.

Sultaines useful in the present invention include those compounds having the formula $(R(R^1)_2 N^+R^2SO^{3-}$, in which R is a $C_6$-$C_{18}$ hydrocarbyl group, each $R^1$ is typically independently $C_1$-$C_3$ alkyl, e.g. methyl, and $R^2$ is a $C_1$-$C_6$ hydrocarbyl group, e.g. a $C_1$-$C_3$ alkylene or hydroxyalkylene group.

A typical listing of zwitterionic classes, and species of these surfactants, is given in U.S. Pat. No. 3,929,678 issued to Laughlin and Heuring on Dec. 30, 1975. Further examples are given in "Surface Active Agents and Detergents" (Vol. I and II by Schwartz, Perry and Berch).

In an embodiment, the composition of the present invention includes a betaine. For example, the composition can include cocoamidopropyl betaine.

Adjuvants

The antimicrobial composition of the invention can also include any number of adjuvants. Specifically, the composition of the invention can include antimicrobial solvent, antimicrobial agent, wetting agent, defoaming agent, thickener, a surfactant, foaming agent, solidification agent, aesthetic enhancing agent (i.e., colorant (e.g., pigment), odorant, or perfume), stabilizing agent (e.g., HEDP) among any number of constituents which can be added to the composition. Such adjuvants can be preformulated with the antimicrobial composition of the invention or added to the system simultaneously, or even after, the addition of the antimicrobial composition. The composition of the invention can also contain any number of other constituents as necessitated by the application, which are known and which can facilitate the activity of the present invention. The adjuvant(s) can be added to the present carboxylic acid composition in the day tank, in a line or conduit after the reaction catalyst, or in the apparatus or system using the peroxycarboxylic acid composition.

Antimicrobial Solvent

Any of a variety of solvents can be useful as antimicrobial solvents in the present compositions. Antimicrobial solvent can be added to use compositions before use. Suitable antimicrobial solvents include acetamidophenol; acetanilide; acetophenone; 2-acetyl-1-methylpyrrole; benzyl acetate; benzyl alcohol; benzyl benzoate; benzyloxyethanol; essential oils (e.g., benzaldehyde, pinenes, terpineols, terpinenes, carvone, cinnamealdehyde, borneol and its esters, citrals, ionenes, jasmine oil, limonene, dipentene, linalool and its esters); diester dicarboxylates (e.g., dibasic esters) such as dimethyl adipate, dimethyl succinate, dimethyl glutarate (including products available under the trade designations DBE, DBE-3, DBE-4, DBE-5, DBE-6, DBE-9, DBE-IB, and DBE-ME from DuPont Nylon), dimethyl malonate, diethyl adipate, diethyl succinate, diethyl glutarate, dibutyl succinate, and dibutyl glutarate; dimethyl sebacate, dimethyl pimelate, dimethyl suberate; dialkyl carbonates such as dimethyl carbonate, diethyl carbonate, dipropyl carbonate, diisopropyl carbonate, and dibutyl carbonate; organo-nitriles such as acetonitrile and benzonitrile; and phthalate esters such as dibutyl phthalate, diethylhexyl phthalate, and diethyl phthalate. Mixtures of antimicrobial solvents can be used if desired.

The antimicrobial solvent can be selected based upon the characteristics of the surface and microbes to which the antimicrobial composition will be applied and upon the nature of any coating, soil or other material that will be contacted by the antimicrobial composition and optionally removed from the surface. Polar solvents, and solvents that are capable of hydrogen bonding typically will perform well on a variety of surfaces and microbes and thus, for such applications, can be selected. In certain applications, the antimicrobial solvent can be selected for a high flashpoint (e.g., greater than about 30° C., greater than about 50° C., or greater than about 100° C.), low odor, and low human and animal toxicity.

In an embodiment, the antimicrobial solvent is compatible as an indirect or direct food additive or substance; especially those described in the Code of Federal Regulations (CFR), Title 21—Food and Drugs, parts 170 to 186. The compositions of the invention should contain sufficient antimicrobial solvent to provide the desired rate and type of microbial reduction.

The present composition can include an effective amount of antimicrobial solvent, such as about 0.01 wt-% to about 60 wt-% antimicrobial solvent, about 0.05 wt-% to about 15 wt-% antimicrobial solvent, or about 0.08 wt-% to about 5 wt-% antimicrobial solvent.

Additional Antimicrobial Agent

The antimicrobial compositions of the invention can contain an additional antimicrobial agent. Additional antimicrobial agent can be added to use compositions before use. Suitable antimicrobial agents include carboxylic esters (e.g., p-hydroxy alkyl benzoates and alkyl cinnamates), sulfonic acids (e.g., dodecylbenzene sulfonic acid), iodo-compounds or active halogen compounds (e.g., elemental halogens, halogen oxides (e.g., NaOCl, HOCl, HOBr, $ClO_2$), iodine, interhalides (e.g., iodine monochloride, iodine dichloride, iodine trichloride, iodine tetrachloride, bromine chloride, iodine monobromide, or iodine dibromide), polyhalides, hypochlorite salts, hypochlorous acid, hypobromite salts, hypobromous acid, chloro- and bromo-hydantoins, chlorine dioxide, and sodium chlorite), organic peroxides including benzoyl peroxide, alkyl benzoyl peroxides, ozone, singlet oxygen generators, and mixtures thereof, phenolic derivatives (e.g., o-phenyl phenol, o-benzyl-p-chlorophenol, tert-amyl phenol and $C_1$-$C_6$ alkyl hydroxy benzoates), quaternary ammonium compounds (e.g., alkyldimethylbenzyl ammonium chloride, dialkyldimethyl ammonium chloride and mixtures thereof), and mixtures of such antimicrobial agents, in an amount sufficient to provide the desired degree of microbial protection.

In an embodiment, the present composition can include added peroxycarboxylic acid and/or hydrogen peroxide.

The present composition can include an effective amount of antimicrobial agent, such as about 0.001 wt-% to about 60 wt-% antimicrobial agent, about 0.01 wt-% to about 15 wt-% antimicrobial agent, or about 0.08 wt-% to about 2.5 wt-% antimicrobial agent.

Hydrotrope

The composition employed in the methods of the invention may also include a hydrotrope coupler or solubilizer. Such materials can be used to ensure that the composition remains phase stable and in a single highly active aqueous form. Such hydrotrope solubilizers or couplers can be used at compositions which maintain phase stability but do not result in unwanted compositional interaction.

Representative classes of hydrotrope solubilizers or coupling agents include an anionic surfactant such as an alkyl sulfate, an alkyl or alkane sulfonate, a linear alkyl benzene or naphthalene sulfonate, a secondary alkane sulfonate, alkyl ether sulfate or sulfonate, an alkyl phosphate or phosphonate, dialkyl sulfosuccinic acid ester, sugar esters (e.g., sorbitan esters) and a $C_{8-10}$ alkyl glucoside.

Preferred coupling agents for use in the methods of the invention include n-octane sulfonate and aromatic sulfonates such as an alkyl aryl sulfonate (e.g., sodium xylene sulfonate or naphthalene sulfonate). Many hydrotrope solubilizers independently exhibit some degree of antimicrobial activity at low pH. Such action adds to the efficacy of the invention but is not a primary criterion used in selecting an appropriate solubilizing agent. Since the presence of the peroxycarboxylic acid material in the protonated neutral state provides beneficial biocidal or antimicrobial activity, the coupling agent should be selected not for its independent antimicrobial activity but for its ability to provide effective single phase composition stability in the presence of substantially insoluble peroxycarboxylic acid materials and the more soluble compositions of the invention. Generally, any number of surfactants may be used consistent with the purpose of this constituent.

Anionic surfactants useful with the invention include alkyl carboxylates, linear alkylbenzene sulfonates, paraffin sulfonates and secondary n-alkane sulfonates, sulfosuccinate esters and sulfated linear alcohols.

Zwitterionic or amphoteric surfactants useful with the invention include θ-N-alkylaminopropionic acids, n-alkyl-θ-iminodipropionic acids, imidazoline carboxylates, n-alky-Il-etaines, amine oxides, sulfobetaines and sultaines.

Nonionic surfactants useful in the context of this invention are generally polyether (also known as polyalkylene oxide, polyoxyalkylene or polyalkylene glycol) compounds. More particularly, the polyether compounds are generally polyoxypropylene or polyoxyethylene glycol compounds. Typically, the surfactants useful in the context of this invention are synthetic organic polyoxypropylene (PO)-polyoxyethylene (EO) block copolymers. These surfactants have a diblock polymer including an EO block and a PO block, a center block of polyoxypropylene units (PO), and having blocks of polyoxyethylene grated onto the polyoxypropylene unit or a center block of EO with attached PO blocks. Further, this surfactant can have further blocks of either polyoxyethylene or polyoxypropylene in the molecule. The average molecular weight of useful surfactants ranges from about 1000 to about 40,000 and the weight percent content of ethylene oxide ranges from about 10-80% by weight.

Also useful in the context of this invention are surfactants including alcohol alkoxylates having EO, PO and BO blocks. Straight chain primary aliphatic alcohol alkoxylates can be particularly useful as sheeting agents. Such alkoxylates are also available from several sources including BASF Wyandotte where they are known as "Plurafac" surfactants. A particular group of alcohol alkoxylates found to be useful are those having the general formula R-(EO)$_m$-(PO)$_n$, wherein m is an integer of about 2-10 and n is an integer from about 2-20. R can be any suitable radical such as a straight chain alkyl group having from about 6-20 carbon atoms.

Other useful nonionic surfactants of the invention include capped aliphatic alcohol alkoxylates. These end caps include but are not limited to methyl, ethyl, propyl, butyl, benzyl and chlorine. Useful alcohol alkoxylated include ethylene diamine ethylene oxides, ethylene diamine propylene oxides, mixtures thereof, and ethylene diamine EO-PO compounds, including those sold under the tradename Tetronic. Preferably, such surfactants have a molecular weight of about 400 to 10,000. Capping improves the compatibility between the nonionic and the oxidizers hydrogen peroxide and peroxycarboxylic acid, when formulated into a single composition. Other useful nonionic surfactants are alkylpolyglycosides.

Another useful nonionic surfactant of the invention is a fatty acid alkoxylate wherein the surfactant includes a fatty acid moiety with an ester group including a block of EO, a block of PO or a mixed block or heteric group. The molecular weights of such surfactants range from about 400 to about 10,000, a preferred surfactant has an EO content of about 30 to 50 wt-% and wherein the fatty acid moiety contains from about 8 to about 18 carbon atoms.

Similarly, alkyl phenol alkoxylates have also been found useful in the invention. Such surfactants can be made from an alkyl phenol moiety having an alkyl group with 4 to about 18 carbon atoms, can contain an ethylene oxide block, a propylene oxide block or a mixed ethylene oxide, propylene oxide block or heteric polymer moiety. Preferably such surfactants have a molecular weight of about 400 to about 10,000 and have from about 5 to about 20 units of ethylene oxide, propylene oxide or mixtures thereof.

The concentration of hydrotrope useful in the present invention generally ranges from about 0.1 to about 20 wt-%, preferably from about 0.5 to about 10 wt-%, most preferably from about 1 to about 4 wt-%.

Wetting or Defoaming Agents

Also useful in the composition of the invention are wetting and defoaming agents. Wetting agents function to increase the surface contact or penetration activity of the antimicrobial composition of the invention. Wetting agents which can be used in the composition of the invention include any of those constituents known within the art to raise the surface activity of the composition of the invention.

Generally, defoamers which can be used in accordance with the invention include silica and silicones; aliphatic acids or esters; alcohols; sulfates or sulfonates; amines or amides; halogenated compounds such as fluorochlorohydrocarbons; vegetable oils, waxes, mineral oils as well as their sulfated derivatives; fatty acid soaps such as alkali, alkaline earth metal soaps; and phosphates and phosphate esters such as alkyl and alkaline diphosphates, and tributyl phosphates among others; and mixtures thereof.

In an embodiment, the present compositions can include antifoaming agents or defoamers which are of food grade quality given the application of the method of the invention. To this end, one of the more effective antifoaming agents includes silicones. Silicones such as dimethyl silicone, glycol polysiloxane, methylphenol polysiloxane, trialkyl or tetralkyl silanes, hydrophobic silica defoamers and mixtures thereof can all be used in defoaming applications. Commercial defoamers commonly available include silicones such as Ardefoam® from Armour Industrial Chemical Company which is a silicone bound in an organic emulsion; Foam Kill® or Kresseo® available from Krusable Chemical Company which are silicone and non-silicone type defoamers as well as silicone esters; and Anti-Foam A® and DC-200 from Dow Corning Corporation which are both food grade type silicones among others. These defoamers can be present at a concentration range from about 0.01 wt-% to 5 wt-%, from about 0.01 wt-% to 2 wt-%, or from about 0.01 wt-% to about 1 wt-%.

Thickening or Gelling Agents

The present compositions can include any of a variety of known thickeners. Suitable thickeners include natural gums such as xanthan gum, guar gum, or other gums from plant mucilage; polysaccharide based thickeners, such as alginates, starches, and cellulosic polymers (e.g., carboxymethyl cellulose); polyacrylates thickeners; and hydrocolloid thickeners, such as pectin. In an embodiment, the thickener does not leave contaminating residue on the surface of an object. For example, the thickeners or gelling agents can be compatible with food or other sensitive products in contact areas. Generally, the concentration of thickener employed in the present compositions or methods will be dictated by the desired viscosity within the final composition. However, as a general guideline, the viscosity of thickener within the present composition ranges from about 0.1 wt-% to about 1.5 wt-%, from about 0.1 wt-% to about 1.0 wt-%, or from about 0.1 wt-% to about 0.5 wt-%.

Bleaching Agent

The present composition can include a known bleaching agent, such as an active halogen compound. Suitable bleaching agents include any of the well known bleaching agents capable of removing stains from such substrates as dishes, flatware, pots and pans, textiles, countertops, appliances, flooring, etc. without significantly damaging the substrate. A nonlimiting list of bleaches includes hypochlorites, chlorides, chlorinated phosphates, chloroisocyanates, chloramines, etc.; and peroxide compounds such as hydrogen peroxide, perborates, percarbonates, etc. Generally, if the application requires a color sensitive active agent, bleaches such as peroxide compounds are generally preferred. However, if the application does not require color sensitivity, halogen bleaches may be used.

Suitable bleaching agents include those that liberate an active halogen species such as chlorine, bromine, hypochlorite ion, hypobromide ion, under conditions normally encountered in typical cleaning processes. The active halogen compound can, for example, be a source of a free elemental halogen or —OX— wherein X is Cl or Br, under conditions normally used in detergent-bleaching cleaning processes. In an embodiment, the active halogen compound releases chlorine or bromine species. In an embodiment, the active halogen compound releases chlorine.

Chlorine releasing compounds include potassium dichloroisocyanurate, sodium dichloroisocyanurate, chlorinated trisodiumphosphate, calcium hypochlorite, lithium hypochlorite, monochloramine, dichloroamine, [(monotrichloro)-tetra (monopotassium dichloro)]pentaisocyanurate, paratoluene sulfondichloro-amide, trichloromelamine, N-chlorammeline, N-chlorosuccinimide, N,N'-dichloroazodicarbonamide, N-chloro-acetyl-urea, N,N'-dichlorobiuret, chlorinated dicyandiamide, trichlorocyanuric acid, dichloroglycoluril, 1,3-dichloro-5,5-dimethyl hydantion, 1-3-dichloro-5-ethyl-5-methyl hydantoin, 1-choro-3-bromo-5-ethyl-5-methyl hydantoin, dichlorohydantoin, trichloromelamine, sulfondichloroamide, trichlorocyanuric acid, salts or hydrates thereof, and mixtures thereof. In an embodiment, an chlorine releasing compound includes sodium dichloroisocyanurate. In an embodiment, an organic chlorine releasing compound can be sufficiently soluble in water to have a hydrolysis constant (K) of about $10^{-4}$ or greater.

Encapsulated chlorine sources may also be used to enhance the stability of the chlorine source in the composition (see, for example, U.S. Pat. Nos. 4,618,914 and 4,830,773, the disclosures of which are incorporated by reference herein).

A bleaching agent may also include an agent containing or acting as a source of active oxygen. The active oxygen compound acts to provide a source of active oxygen, for example, may release active oxygen in aqueous solutions. An active oxygen compound can be inorganic or organic, or can be a mixture thereof. Some examples of active oxygen compound include peroxygen compounds, or peroxygen compound adducts. Some examples of active oxygen compounds or sources include hydrogen peroxide, perborates, sodium carbonate peroxyhydrate, phosphate peroxyhydrates, potassium permonosulfate, and sodium perborate mono and tetrahydrate, with and without activators such as tetraacetylethylene diamine, and the like.

In an embodiment the bleach is an alkali metal salt of a chloroisocyanurate, a hydrate thereof, or a mixture thereof. Dichloroisocyanurate dihydrate, a suitable chlorine releasing compound, is commercially available. This compound can be represented by the formula:

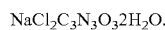

$NaCl_2C_3N_3O_3 2H_2O$.

The composition can also include an effective amount of a known bleach activator, such as tetraacetylethylene diamine or a metal, such as manganese.

The composition can include bleaching agent at about 0.5 to 20 wt-%, about 1 to 10 wt-%, or about 2 to 8 wt-% of the composition. The composition can include up to about 10 wt-% bleaching agent, and in some embodiments, about 0.1 to about 6 wt-%.

Use Compositions

The present compositions include concentrate compositions and use compositions. For example, a concentrate composition can be diluted, for example with water, to form a use composition. In an embodiment, a concentrate composition can be diluted to a use solution before to application to an object. For reasons of economics, the concentrate can be marketed and an end user can dilute the concentrate with water or an aqueous diluent to a use solution.

The level of active components in the concentrate composition is dependent on the intended dilution factor and the desired activity of the peroxycarboxylic acid compound. Generally, a dilution of about 1 fluid ounce to about 20 gallons of water to about 5 fluid ounces to about 1 gallon of water is used for aqueous antimicrobial compositions. Higher use dilutions can be employed if elevated use temperature (greater than 25° C.) or extended exposure time (greater than 30 seconds) can be employed. In the typical use locus, the concentrate is diluted with a major proportion of water using commonly available tap or service water mixing the materials at a dilution ratio of about 3 to about 20 ounces of concentrate per 100 gallons of water.

For example, a use composition can include about 0.01 to about 4 wt-% of a concentrate composition and about 96 to about 99.99 wt-% diluent; about 0.5 to about 4 wt-% of a concentrate composition and about 96 to about 99.5 wt-% diluent; about 0.5, about 1, about 1.5, about 2, about 2.5, about 3, about 3.5, or about 4 wt-% of a concentrate composition; about 0.01 to about 0.1 wt-% of a concentrate composition; or about 0.01, about 0.02, about 0.03, about 0.04, about 0.05, about 0.06, about 0.07, about 0.08, about 0.09, or about 0.1 wt-% of a concentrate composition. Amounts of an ingredient in a use composition can be calculated from the amounts listed above for concentrate compositions and these dilution factors.

The present methods can employ peroxycarboxylic acid at a concentration effective for reducing the population of one or more microorganisms. Such effective concentrations include about 2 to about 500 ppm medium chain peroxycarboxylic acid, about 2 to about 300 ppm peroxycarboxylic acid, about 5 to about 100 ppm peroxycarboxylic acid, about 5 to about 60 ppm peroxycarboxylic acid, about 5 to about 45 ppm peroxycarboxylic acid, about 5 to about 35 ppm peroxycarboxylic acid, about 5 to about 25 ppm peroxycarboxylic acid, about 8 to about 50 ppm peroxycarboxylic acid, about 10 to about 500 ppm peroxycarboxylic acid, about 10 to about 50 ppm peroxycarboxylic acid, about 40 to about 140 ppm peroxycarboxylic acid, about 100 to about 250 ppm peroxycarboxylic acid, or about 200 to about 300 ppm peroxycarboxylic acid. In an embodiment, the use composition can include about 2 to about 500 ppm peroxycarboxylic acid, about 5 to about 2000 ppm carboxylic acid, about 95 to about 99.99 wt-% carrier and/or diluent (e.g., water); and about 2 to about 23,000 ppm polyalkylene oxide, capped polyalkylene oxide, alkoxylated surfactant, anionic surfactant, or mixture thereof.

The level of reactive species, such as peroxycarboxylic acids and/or hydrogen peroxide, in a use composition can be affected, typically diminished, by organic matter that is found in or added to the use composition. For example, when the use composition is a bath or spray used for washing an object, soil on the object can consume peroxy acid and peroxide. Thus, the present amounts of ingredients in the use compositions refer to the composition before or early in use, with the understanding that the amounts will diminish as organic matter is added to the use composition.

In an embodiment, the present use composition can be made more acidic by passing the concentrate through an acidifying column, or by adding additional acidulant to the use composition.

Other Fluid Compositions

The present and compositions can include a critical, near critical, or supercritical (densified) fluid and an antimicrobial agent or a gaseous composition of an antimicrobial agent. The densified fluid can be a near critical, critical, supercritical fluid, or another type of fluid with properties of a supercritical fluid. Fluids suitable for densification include carbon dioxide, nitrous oxide, ammonia, xenon, krypton, methane, ethane, ethylene, propane, certain fluoroalkanes (e.g., chlorotrifluoromethane and monofluoromethane), and the like, or mixtures thereof. Suitable fluids include carbon dioxide.

In an embodiment, the present compositions or methods include densified carbon dioxide, peroxycarboxylic acid, and carboxylic acid. Such a composition can be referred to as a densified fluid peroxycarboxylic acid composition. In another embodiment, the antimicrobial composition includes the fluid, an antimicrobial agent, and any of the optional or added ingredients, but is in the form of a gas.

Densified fluid antimicrobial compositions can be applied by any of several methods known to those of skill in the art. Such methods include venting at an object a vessel containing densified fluid and antimicrobial agent. The aqueous phase, which includes hydrogen peroxide, is advantageously retained in the device. The vented gas includes an effective amount of antimicrobial agent making the densified fluid peroxycarboxylic acid compositions effective antimicrobial agents.

Because of the high pressure nature of the densified fluid compositions of the invention, these compositions are typically applied by venting a vessel containing the composition through a pressure relief device that is designed to promote rapid efficient coverage of an object. Devices including such a pressure relief device include sprayers, foggers, foamers, foam pad applicators, brush applicators or any other device that can permit the expansion of the fluid materials from high pressure to ambient pressure while applying the material to an object. The densified fluid peroxycarboxylic acid composition can also be applied to an object by any of a variety of methods known for applying gaseous agents to an object.

Densified fluid antimicrobial compositions can be made by reacting an oxidizable substrate with an oxidizing agent in a medium comprising a densified fluid to form an antimicrobial composition. This reaction is typically carried out in a vessel suitable for containing a densified fluid. Reacting can include adding to the vessel the oxidizable substrate and the oxidizing agent, and adding fluid to the vessel to form the densified fluid. In an embodiment, the reaction is between a carboxylic acid and hydrogen peroxide to form the corresponding peroxycarboxylic acid. The hydrogen peroxide is commonly supplied in the form of an aqueous solution of hydrogen peroxide.

Supercritical, subcritical, near supercritical, and other dense fluids and solvents that can be employed with such fluids are disclosed in U.S. Pat. No. 5,306,350, issued Apr. 26, 1994 to Hoy et al., which is incorporated by reference herein for such disclosure. Supercritical and other dense forms of carbon dioxide, and cosolvents, co-surfactants, and other additives that can be employed with these forms of carbon dioxide are disclosed in U.S. Pat. No. 5,866,005, issued Feb. 2, 1999 to DeSimone et al., which is incorporated by reference herein for such disclosure.

Methods Employing the Peroxycarboxylic Acid Compositions

The present invention includes methods employing the present peroxycarboxylic acid compositions. Typically, these methods employ the antimicrobial or bleaching activity of the peroxycarboxylic acid. For example, the invention includes a method for reducing a microbial population, a method for reducing the population of a microorganism on skin, a method for treating a disease of skin, a method for reducing an odor, or a method for bleaching. These methods can operate on an object, surface, in a body or stream of water or a gas, or the like, by contacting the object, surface, body, or stream with a stabilized ester peroxycarboxylic acid composition of the invention. Contacting can include any of numerous methods for applying a composition, such as spraying the composition, immersing the object in the composition, foam or gel treating the object with the composition, or a combination thereof.

The compositions of the invention can be used for a variety of domestic or industrial applications, e.g., to reduce microbial or viral populations on a surface or object or in a body or stream of water. The compositions can be applied in a variety of areas including kitchens, bathrooms, factories, hospitals, dental offices and food plants, and can be applied to a variety of hard or soft surfaces having smooth, irregular or porous topography. Suitable hard surfaces include, for example, architectural surfaces (e.g., floors, walls, windows, sinks, tables, counters and signs); eating utensils; hard-surface medical or surgical instruments and devices; and hard-surface packaging. Such hard surfaces can be made from a variety of materials including, for example, ceramic, metal, glass, wood or hard plastic. Suitable soft surfaces include, for example paper; filter media, hospital and surgical linens and garments; soft-surface medical or surgical instruments and devices; and soft-surface packaging. Such soft surfaces can be made from a variety of materials including, for example, paper, fiber, woven or nonwoven fabric, soft plastics and elastomers. The compositions of the invention can also be applied to soft surfaces such as food and skin (e.g., a hand). The present compositions can be employed as a foaming or nonfoaming environmental sanitizer or disinfectant.

The antimicrobial compositions of the invention can be included in products such as sterilants, sanitizers, disinfectants, preservatives, deodorizers, antiseptics, fungicides, germicides, sporicides, virucides, detergents, bleaches, hard surface cleaners, hand soaps, waterless hand sanitizers, and pre- or post-surgical scrubs.

The antimicrobial compositions can also be used in veterinary products such as mammalian skin treatments or in products for sanitizing or disinfecting animal enclosures, pens, watering stations, and veterinary treatment areas such as inspection tables and operation rooms. The present compositions can be employed in an antimicrobial foot bath for livestock or people.

The present compositions can be employed for reducing the population of pathogenic microorganisms, such as pathogens of humans, animals, and the like. The compositions can exhibit activity against pathogens including fungi, molds, bacteria, spores, and viruses, for example, *S. aureus, E. coli, Streptococci, Legionella, Pseudomonas aeruginosa*, mycobacteria, tuberculosis, phages, or the like. Such pathogens can cause a varieties of diseases and disorders, including Mastitis or other mammalian milking diseases, tuberculosis, and the like. The compositions of the present invention can reduce the population of microorganisms on skin or other external or mucosal surfaces of an animal. In addition, the present compositions can kill pathogenic microorganisms that spread through transfer by water, air, or a surface substrate. The composition need only be applied to the skin, other external or mucosal surfaces of an animal water, air, or surface.

The antimicrobial compositions can also be used on foods and plant species to reduce surface microbial populations; used at manufacturing or processing sites handling such foods and plant species; or used to treat process waters around such sites. For example, the compositions can be used on food transport lines (e.g., as belt sprays); boot and hand-wash dip-pans; food storage facilities; anti-spoilage air circulation systems; refrigeration and cooler equipment; beverage chillers and warmers, blanchers, cutting boards, third sink areas, and meat chillers or scalding devices. The compositions of the invention can be used to treat produce transport waters such as those found in flumes, pipe transports, cutters, slicers, blanchers, retort systems, washers, and the like. Particular foodstuffs that can be treated with compositions of the invention include eggs, meats, seeds, leaves, fruits and vegetables. Particular plant surfaces include both harvested and growing leaves, roots, seeds, skins or shells, stalks, stems, tubers, corms, fruit, and the like. The compositions may also be used to treat animal carcasses to reduce both pathogenic and non-pathogenic microbial levels.

The present composition is useful in the cleaning or sanitizing of containers, processing facilities, or equipment in the food service or food processing industries. The antimicrobial compositions have particular value for use on food packaging materials and equipment, and especially for cold or hot aseptic packaging. Examples of process facilities in which the composition of the invention can be employed include a milk line dairy, a continuous brewing system, food processing lines such as pumpable food systems and beverage lines, etc. Food service wares can be disinfected with the composition of the invention. For example, the compositions can also be used on or in ware wash machines, dishware, bottle washers, bottle chillers, warmers, third sink washers, cutting areas (e.g., water knives, slicers, cutters and saws) and egg washers. Particular treatable surfaces include packaging such as cartons, bottles, films and resins; dish ware such as glasses, plates, utensils, pots and pans; ware wash machines; exposed food preparation area surfaces such as sinks, counters, tables, floors and walls; processing equipment such as tanks, vats, lines, pumps and hoses (e.g., dairy processing equipment for processing milk, cheese, ice cream and other dairy products); and transportation vehicles. Containers include glass bottles, PVC or polyolefin film sacks, cans, polyester, PEN or PET bottles of various volumes (100 ml to 2 liter, etc.), one gallon milk containers, paper board juice or milk containers, etc.

The antimicrobial compositions can also be used on or in other industrial equipment and in other industrial process streams such as heaters, cooling towers, boilers, retort waters, rinse waters, aseptic packaging wash waters, and the like. The compositions can be used to treat microbes and odors in recreational waters such as in pools, spas, recreational flumes and water slides, fountains, and the like.

A filter containing the composition can reduce the population of microorganisms in air and liquids. Such a filter can remove water and air-born pathogens such as *Legionella*.

The present compositions can be employed for reducing the population of microbes, fruit flies, or other insect larva on a drain or other surface.

The composition may also be employed by dipping food processing equipment into the use solution, soaking the equipment for a time sufficient to sanitize the equipment, and wiping or draining excess solution off the equipment, The composition may be further employed by spraying or wiping food processing surfaces with the use solution, keeping the surfaces wet for a time sufficient to sanitize the surfaces, and removing excess solution by wiping, draining vertically, vacuuming, etc.

The composition of the invention may also be used in a method of sanitizing hard surfaces such as institutional type equipment, utensils, dishes, health care equipment or tools, and other hard surfaces. The composition may also be employed in sanitizing clothing items or fabric which have become contaminated. The use solution is contacted with any of the above contaminated surfaces or items at use temperatures in the range of about 4° C. to 60° C., for a period of time effective to sanitize, disinfect, or sterilize the surface or item. For example, the concentrate composition can be injected into the wash or rinse water of a laundry machine and contacted with contaminated fabric for a time sufficient to sanitize the fabric. Excess solution can then be removed by rinsing or centrifuging the fabric.

The antimicrobial compositions can be applied to microbes or to soiled or cleaned surfaces using a variety of methods. These methods can operate on an object, surface, in a body or stream of water or a gas, or the like, by contacting the object, surface, body, or stream with a composition of the invention. Contacting can include any of numerous methods for applying a composition, such as spraying the composition, immersing the object in the composition, foam or gel treating the object with the composition, or a combination thereof.

A concentrate or use concentration of a composition of the present invention can be applied to or brought into contact with an object by any conventional method or apparatus for applying an antimicrobial or cleaning composition to an object. For example, the object can be wiped with, sprayed with, foamed on, and/or immersed in the composition, or a use solution made from the composition. The composition can be sprayed, foamed, or wiped onto a surface; the composition can be caused to flow over the surface, or the surface can be dipped into the composition. Contacting can be manual or by machine. Food processing surfaces, food products, food processing or transport waters, and the like can be treated with liquid, foam, gel, aerosol, gas, wax, solid, or powdered stabilized compositions according to the invention, or solutions containing these compositions.

The composition can be employed for bleaching pulp. Such a method includes contacting the pulp with a peroxycarboxylic acid composition according to the present invention. Such a peroxycarboxylic acid composition can include added bleaching agent.

The compositions can be employed for waste treatment. Such a method includes contacting the waste with a peroxycarboxylic acid composition according to the present invention. Such a peroxycarboxylic acid composition can include added bleaching agent.

Clean in Place

Other hard surface cleaning applications for the antimicrobial compositions of the invention include clean-in-place systems (CIP), clean-out-of-place systems (COP), washer-decontaminators, sterilizers, textile laundry machines, ultra and nano-filtration systems and indoor air filters. COP systems can include readily accessible systems including wash tanks, soaking vessels, mop buckets, holding tanks, scrub sinks, vehicle parts washers, non-continuous batch washers and systems, and the like.

Generally, the actual cleaning of the in-place system or other surface (i.e., removal of unwanted offal therein) is accomplished with a different material such as a formulated detergent which is introduced with heated water. After this cleaning step, the instant composition would be applied or introduced into the system at a use solution concentration in unheated, ambient temperature water. CIP typically employ flow rates on the order of about 40 to about 600 liters per minute, temperatures from ambient up to about 70° C., and contact times of at least about 10 seconds, for example, about 30 to about 120 seconds. The present composition can remain in solution in cold (e.g., 40° F./4° C.) water and heated (e.g., 140° F./60° C.) water. Although it is not normally necessary to heat the aqueous use solution of the present composition, under some circumstances heating may be desirable to further enhance its antimicrobial activity. These materials are useful at any conceivable temperatures.

A method of sanitizing substantially fixed in-place process facilities includes the following steps. The use solution of the invention is introduced into the process facilities at a temperature in the range of about 4° C. to 60° C. After introduction of the use solution, the solution is held in a container or circulated throughout the system for a time sufficient to sanitize the process facilities (i.e., to kill undesirable microorganisms). After the surfaces have been sanitized by means of the present composition, the use solution is drained. Upon completion of the sanitizing step, the system optionally may be rinsed with other materials such as potable water. The composition can be circulated through the process facilities for 10 minutes or less.

The present method can include delivering the present composition via air delivery to the clean-in-place or other surfaces such as those inside pipes and tanks. This method of air delivery can reduce the volume of solution required.

Contacting a Food Product with the Peroxycarboxylic Acid Composition

The present method and system provide for contacting a food product with a peroxycarboxylic acid composition employing any method or apparatus suitable for applying such a composition. For example, the method and system of the invention can contact the food product with a spray of the composition, by immersion in the composition, by foam or gel treating with the composition, or the like. Contact with a spray, a foam, a gel, or by immersion can be accomplished by a variety of methods known to those of skill in the art for applying antimicrobial agents to food. Contacting the food product can occur in any location in which the food product might be found, such as field, processing site or plant, vehicle, warehouse, store, restaurant, or home. These same methods can also be adapted to apply the stabilized compositions of the invention to other objects.

The present methods require a certain minimal contact time of the composition with food product for occurrence of significant antimicrobial effect. The contact time can vary with concentration of the use composition, method of applying the use composition, temperature of the use composition, amount of soil on the food product, number of microorganisms on the food product, type of antimicrobial agent, or the like. The exposure time can be at least about 5 to about 15 seconds.

In an embodiment, the method for washing food product employs a pressure spray including the composition. During application of the spray solution on the food product, the surface of the food product can be moved with mechanical action, e.g., agitated, rubbed, brushed, etc. Agitation can be by physical scrubbing of the food product, through the action of the spray solution under pressure, through sonication, or by other methods. Agitation increases the efficacy of the spray solution in killing micro-organisms, perhaps due to better exposure of the solution into the crevasses or small colonies containing the micro-organisms. The spray solution, before application, can also be heated to a temperature of about 15 to 20° C., for example, about 20 to 60° C. to increase efficacy. The spray stabilized composition can be left on the food product for a sufficient amount of time to suitably reduce the population of microorganisms, and then rinsed, drained, or evaporated off the food product.

Application of the material by spray can be accomplished using a manual spray wand application, an automatic spray of food product moving along a production line using multiple spray heads to ensure complete contact, or other spray apparatus. One automatic spray application involves the use of a spray booth. The spray booth substantially confines the sprayed composition to within the booth. The production line moves the food product through the entryway into the spray booth in which the food product is sprayed on all its exterior surfaces with sprays within the booth. After a complete coverage of the material and drainage of the material from the food product within the booth, the food product can then exit the booth. The spray booth can include steam jets that can be used to apply the stabilized compositions of the invention. These steam jets can be used in combination with cooling water to ensure that the treatment reaching the food product surface is less than 65° C., e.g., less than 60° C. The temperature of the spray on the food product is important to ensure that the food product is not substantially altered (cooked) by the temperature of the spray. The spray pattern can be virtually any useful spray pattern.

Immersing a food product in a liquid stabilized composition can be accomplished by any of a variety of methods known to those of skill in the art. For example, the food product can be placed into a tank or bath containing the stabilized composition. Alternatively, the food product can be transported or processed in a flume of the stabilized composition. The washing solution can be agitated to increase the efficacy of the solution and the speed at which the solution reduces micro-organisms accompanying the food product. Agitation can be obtained by conventional methods, including ultrasonics, aeration by bubbling air through the solution, by mechanical methods, such as strainers, paddles, brushes, pump driven liquid jets, or by combinations of these methods. The washing solution can be heated to increase the efficacy of the solution in killing micro-organisms. After the food product has been immersed for a time sufficient for the desired antimicrobial effect, the food product can be removed from the bath or flume and the stabilized composition can be rinsed, drained, or evaporated off the food product.

In another alternative embodiment of the present invention, the food product can be treated with a foaming version of the composition. The foam can be prepared by mixing foaming surfactants with the washing solution at time of use. The foaming surfactants can be nonionic, anionic or cationic in nature. Examples of useful surfactant types include, but are not limited to the following: alcohol ethoxylates, alcohol ethoxylate carboxylate, amine oxides, alkyl sulfates, alkyl ether sulfate, sulfonates, quaternary ammonium compounds, alkyl sarcosines, betaines and alkyl amides. The foaming surfactant is typically mixed at time of use with the washing solution. Use solution levels of the foaming agents is from about 50 ppm to about 2.0 wt-%. At time of use, compressed air can be injected into the mixture, then applied to the food product surface through a foam application device such as a tank foamer or an aspirated wall mounted foamer.

In another alternative embodiment of the present invention, the food product can be treated with a thickened or gelled version of the composition. In the thickened or gelled state the washing solution remains in contact with the food product surface for longer periods of time, thus increasing the antimicrobial efficacy. The thickened or gelled solution will also adhere to vertical surfaces. The composition or the washing solution can be thickened or gelled using existing technologies such as: xanthan gum, polymeric thickeners, cellulose thickeners, or the like. Rod micelle forming systems such as amine oxides and anionic counter ions could also be used. The thickeners or gel forming agents can be used either in the concentrated product or mixing with the washing solution, at time of use. Typical use levels of thickeners or gel agents range from about 100 ppm to about 10 wt-%.

Aseptic Packaging

In the method of the present invention, aseptic packaging includes contacting the container with a composition according to the present invention. Such contacting can be accomplished using a spray device or soaking tank or vessel to intimately contact the inside of the container with the composition for sufficient period of time to clean or reduce the microbial population in the container. The container is then emptied of the amount of the present composition used. After emptying, the container can then be rinsed with potable water or sterilized water (which can include a rinse additive) and again emptied. After rinsing, the container can be filled with the liquid beverage. The container is then sealed, capped or closed and then packed for shipment for ultimate sale.

Figure 18:
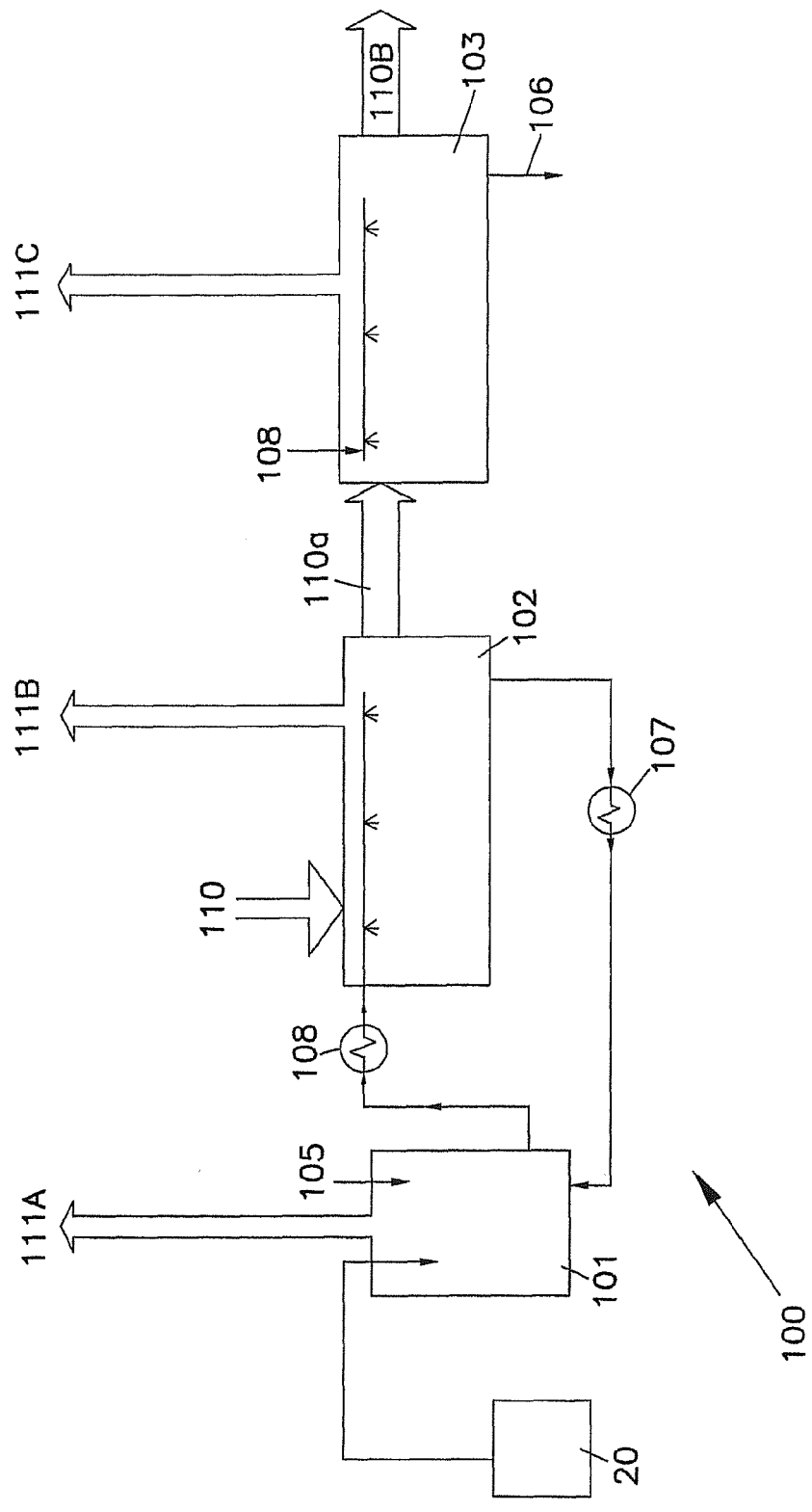
FIG. 18 is a diagram of a beverage plant, including a cold aseptic filling plant, in which either carbonated or non-carbonated beverages can be prepared and bottled.

FIG. 18 shows a schematic for an embodiment of a bottle spraying/bottling operation using a composition according to the present invention. The operation can be a cold aseptic operation. FIG. 18 shows a plant 100 that can contact beverage bottles with a medium chain peroxycarboxylic acid composition for a sanitizing regime. In FIG. 18, bottles 110 are passed through a sterilizing tunnel 102. The sanitized bottles 110a then pass through a rinsing tunnel 103 and emerge as sanitized rinsed bottles 110b.

In the process, bulk medium chain peroxycarboxylic acid composition is added to a holding tank 101. Commonly, the materials are maintained at a temperature of about 22° C. in tank 101. To obtain the effective use concentration of the medium chain peroxycarboxylic acid composition, make-up water 105 is combined with the concentrated medium chain peroxycarboxylic acid composition into the tank 101. The medium chain peroxycarboxylic acid use composition is passed through a heater 108 to reach a temperature of about 45-50° C. The heated medium chain peroxycarboxylic acid use composition is sprayed within sterilizing tunnel 102 into and onto all surfaces of the bottle 110. An intimate contact between the medium chain peroxycarboxylic acid composition and the bottle 110 is essential for reducing microbial populations to a sanitizing level.

After contact with the medium chain peroxycarboxylic acid use composition and after dumping any excess composition from the bottles, the sanitized bottles 110 are then passed to a fresh water rinse tunnel 103. Fresh water 108 is provided from a fresh water make-up into a spray rinsing tunnel 103. The fresh water can include a rinse additive. Excess spray drains from rinsing tunnel 103 to drain 106. Within the tunnel 103, sanitized bottles 110a are thoroughly rinsed with fresh water. The complete removal of the medium chain peroxycarboxylic acid composition from the bottles 110a is important for maintaining high quality of the beverage product. The rinsed and sanitized bottles 110b are then removed from the rinsing tunnel.

The day tank 101, the sterilizing tunnel 102 and the rinsing tunnel 103 are all respectively vended to wet scrubber or vent 111a, 111b or 111c to remove vapor or fumes from the system components. The sanitizer material that has been sprayed and drained from the bottles 110a accumulate in the bottom of the spray tunnel 102 and is then recycled through recycle line and heater 107 into the day tank 101.

The contact between the bottles and the medium chain peroxycarboxylic acid antimicrobial composition can be at a temperature of greater than about 0° C., greater than 25° C., or greater than about 40° C. Temperatures between about 40° C. and 90° C. can be used. In certain embodiments, contact at 40° C. to 60° C. for at least 5 sec, for example at least about 10 sec, contact time is employed.

In the cold aseptic filling of 16 ounce polyethylene terephthalate (PET bottle), or other polymeric, beverage containers, a process has been adopted using a medium chain peroxycarboxylic acid composition. The medium chain peroxycarboxylic acid composition can be diluted to a use concentration of about 0.1 to about 10 wt % and maintained at an effective elevated temperature of about 25° C. to about 70° C., e.g., about 40° C. to about 60° C. The spray or flood of the bottle with the material ensures contact between the bottle and the sanitizer material for at least 5, e.g., about 10, seconds. After flooding is complete, the bottle can be drained of all contents for a minimum of 2 seconds and optionally followed by a 5 second water rinse with sterilized water using about 200 milliliters of water at 38° C. (100° F.). If optionally filled with the rinse water, the bottle is then drained of the sterilized water rinse for at least 2 seconds and is immediately filled with liquid beverage. The rinse water can include a rinse additive. After the rinse is complete, the bottles usually maintain less than 10, e.g., 3, milliliters of rinse water after draining.

Textile Cleaning

The present invention includes methods and compositions for removing soil from textiles. The composition of the invention can be used with typical commercial textile cleaning or laundering processes and machines. The present method can include contacting a laundry item in a laundry machine with a penetrant composition in the form of an aqueous presoak, preflush, prewash, or other step prior to the cleaning step. A suitable laundry process employs a washer/extractor. Laundry cleaning processes can include processes such as flushing, sudsing, draining, bleaching, rinsing, extracting, repetitions thereof, or combinations thereof. The bleaching composition can include a composition according to the present invention.

Flushing can include contacting the laundry item with a flushing composition. In an embodiment, flushing is the initial wetting step in the machine that carries out the washing procedure. A method of cleaning laundry can include flushing one, two, or more times. Conventional flushing compositions are water (e.g., soft or tap water). In conventional systems, flushing can separate loose soil from and wet a laundry item, but little more. Flushing can also be referred to as presoaking, preflushing, or prewashing.

Sudsing can include cleaning the laundry item with a sudsing cleaning composition. The sudsing cleaning composition typically includes surfactants and other cleaners, and can include a bleach. Sudsing can follow flushing.

Draining includes removing a cleaning, flushing, or other composition from the laundry item, for example, by gravity and/or centrifugal force. Draining can follow sudsing. Draining can occur between repeats of flushing. In an embodiment, the textile is cleaned with a textile cleaning composition including a built detergent and chlorine bleach in a suds/bleach combination or in two separate wash steps, i.e. suds steps with built detergent followed by bleach step with chlorine.

Bleaching can include cleaning the laundry item with a bleach composition. Bleaching can follow draining and/or sudsing. The bleaching composition can include a composition according to the present invention.

Rinsing can include contacting the laundry item with a rinse composition suitable for removing remaining cleaning (sudsing and/or bleach) composition. The rinse composition can, for example, be water (e.g., soft or tap water), a sour rinse, or a rinse including softener. A method of cleaning laundry can include one, two, three, or more rinses. Rinsing can follow bleaching and/or sudsing.

Extracting can include removing a rinse composition from the laundry item, typically with centrifugal force. Extracting can follow one or more rinsings.

The present method and composition can be employed on any of a variety of textiles. Suitable textiles include cotton, cotton/polyester blend, polyester, and the like.

The present invention may be better understood with reference to the following examples. These examples are intended to be representative of specific embodiments of the invention, and are not intended as limiting the scope of the invention.

EXAMPLES

Example 1

Making Peroxyacetic Acid with an Apparatus Including a Pretreatment Column and a Reaction Catalyst The present apparatus and method were employed to make the compositions on Tables 1 through 4 below. All equilibrium values were calculated values from the reported $K_{eq}$ of 2.70 for peroxyacetic acid. In the case of mixed peracids etc., the $K_{eq}$ was assumed to be 2.70.

The stability of certain of the test compositions was monitored with and without stabilizer (HEDP) added.

TABLE 1

| | Initial wt-% | | | | Wt-% at Equilibrium | |
|---|---|---|---|---|---|---|
| Test | Carboxylic Acid | Hydrogen Peroxide | Water | Total | Peroxy Acid | Hydrogen Peroxide |
| I | 56.5 | 30.5 | 13.0 | 100.0 | 35.3 | 14.6 |
| II | 43.6 | 20.5 | 35.9 | 100.0 | 17.3 | 12.7 |
| III | 20.0 | 28.0 | 52.0 | 100.0 | 9.7 | 23.6 |
| IV | 78.0 | 7.7 | 14.3 | 100.0 | 13.1 | 1.9 |
| V | 5.0 | 5.0 | 90.0 | 100.0 | 0.5 | 4.8 |

TABLE 2

| | Initial wt-% | | | | Wt-% at Equilibrium | |
|---|---|---|---|---|---|---|
| Test | Short Chain Carboxylic Acid | Hydrogen Peroxide | Water | Total | Peroxy Acid | Hydrogen Peroxide |
| VI | 56.5 | 30.5 | 13.0 | 100.0 | 35.3 | 14.6 |
| VII | 43.6 | 20.5 | 35.9 | 100.0 | 17.3 | 12.7 |
| VIII | 20.0 | 28.0 | 52.0 | 100.0 | 9.7 | 23.6 |
| IX | 78.0 | 7.7 | 14.3 | 100.0 | 13.1 | 1.9 |
| X | 5.0 | 5.0 | 90.0 | 100.0 | 0.5 | 4.8 |

TABLE 3

| | Initial wt-% | | | | | Wt-% at Equilibrium | |
|---|---|---|---|---|---|---|---|
| Test | Medium Chain Carboxylic Acid | Hydrogen Peroxide | Hydrotrope | Water | Total | Peroxy Acid | Hydrogen Peroxide |
| XI | 20.0 | 30.0 | 25 | 25.0 | 100.0 | 18.5 | 31.7 |
| XII | 10.0 | 20.0 | 15 | 55.0 | 100.0 | 6.8 | 20.4 |
| XIII | 5.0 | 20.0 | 10 | 65.0 | 100.0 | 2.1 | 21.3 |
| XIV | 3.0 | 22.5 | 10 | 64.5 | 100.0 | 1.2 | 21.6 |

TABLE 4

| | Initial wt-% | | | | | Wt-% at Equilibrium | | |
|---|---|---|---|---|---|---|---|---|
| Test | Short Chain Carboxylic Acid | Medium Chain Carboxylic Acid | Hydrogen Peroxide | Hydrotrope | Water | Total | Short Chain Peroxy Acid | Medium Chain Peroxy Acid | Hydrogen Peroxide |
| XV | 48.0 | 20.0 | 10.0 | 12 | 10.0 | 100 | 13.6 | 5.7 | 2.8 |
| XVI | 56.0 | 8.0 | 12.0 | 12 | 12.0 | 100 | 18.8 | 2.7 | 4.0 |
| XVII | 60.0 | 2.0 | 13.0 | 12 | 13.0 | 100 | 22.1 | 0.7 | 4.6 |
| XVIII | 43.6 | 1.0 | 20.5 | 0 | 34.9 | 100 | 17.4 | 0.4 | 12.6 |

TABLE 5

| | Initial wt-% | | | | Measured Output | | |
|---|---|---|---|---|---|---|---|
| Test | Carboxylic Acid | Hydrogen Peroxide | Water | Total | Peroxy Acid | of Percarboxylic Acid (wt-%) | Predicted Peracid | % of Pred. |
| XIX | Acetic acid | 11 | 30 | 59 | 100 | 5.3 | 5.6 | 95 |
| XX | Acetic acid | 20 | 28 | 52 | 100 | 9.2 | 9.7 | 95 |
| XXI | Acetic acid | 44 | 18 | 38 | 100 | 14.3 | 15.3 | 93 |
| XXII | Acetic acid | 78 | 7 | 15 | 100 | 13.0 | 12.6 | 103 |

TABLE 5-continued

| | | Initial wt-% | | | | Measured Output | | |
|---|---|---|---|---|---|---|---|---|
| Test | Carboxylic Acid | Hydrogen Peroxide | Water | Total | Peroxy Acid | of Percarboxylic Acid (wt-%) | Predicted Peracid | % of Pred. |
| XXIV | Acetic acid | 41 | 17 | 42 | 100 | 12.0 | 13.4 | 90 |
| XXV | Acetic acid | 50 | 20 | 30 | 100 | 20.0 | 19.9 | 101 |
| XXVI | Acetic acid | 60 | 20 | 20 | 100 | 25.0 | 25.2 | 99 |
| XXVII | Acetic acid | 5 | 5 | 90 | 100 | 0.4 | 0.5 | 78 |
| XXVIII | Glycolic acid | 55 | 8 | 38 | 100 | 1.2 | 8.3 | 14 |
| XXIX | Succinic acid | 7 | 3 | 90 | 100 | 0.2 | 0.4 | 51 |
| XXX | Octanoic acid | 50 | 18 | 32 | 100 | 0.54 | 16.0 | 3 |
| XXXI | Acetic acid | 46 | 19 | 35 | 100 | 17.0 | 17.2 | 99 |
| XXXII | Acetic acid | 50 | 20 | 30 | 100 | 20.2 | 19.9 | 102 |

TABLE 6

Stability of Peracetic Acid Products from Dowex M31 Catalyst at 70° F.

| | Measured Concentration of Peracetic Acid (wt-%) | |
|---|---|---|
| Time (days) | XXV (no HEDP) | XXV (HEDP added) |
| 0.0 | 18.3 | 18.9 |
| 7.0 | 19.0 | 19.1 |
| 13.0 | 19.1 | 19.0 |

TABLE 7

Stability of Peracetic Acid Products From Dowex M31 Catalyst at 140° F.

| | Measured Concentration of Peracetic Acid (wt-%) | |
|---|---|---|
| Time (days) | XXVI (no HEDP) | XXV (HEDP added) |
| 0.0 | 18.3 | 18.9 |
| 7.0 | 15.8 | 15.4 |
| 13.0 | 15.8 | 14.3 |

TABLE 8

Stability of Peracetic Acid Products From Dowex M31 Catalyst at 70° F.

| | Measured Concentration of Peracetic Acid (wt-%) | |
|---|---|---|
| Time (days) | XXVI (no HEDP) | XXVI (HEDP added) |
| 0.0 | 25.7 | 25.7 |
| 3.0 | 23.6 | 22.8 |

It should be noted that, as used in this specification and the appended claims, the singular forms "a," "an," and "the" include plural referents unless the content clearly dictates otherwise. Thus, for example, reference to a composition containing "a compound" includes a mixture of two or more compounds. It should also be noted that the term "or" is generally employed in its sense including "and/or" unless the content clearly dictates otherwise.

All publications and patent applications in this specification are indicative of the level of ordinary skill in the art to which this invention pertains.

The invention has been described with reference to various specific and preferred embodiments and techniques. However, it should be understood that many variations and modifications may be made while remaining within the spirit and scope of the invention.

We claim:

1. An apparatus for making peroxycarboxylic acid, comprising:
   (a) a first reaction catalyst column configured for catalyzing a reaction of a carboxylic acid composition and a hydrogen peroxide to produce peroxycarboxylic acid;
   (b) a first pretreatment column comprising a removable pretreatment cartridge and configured for removing metal ions from only a carboxylic acid composition; and
   (c) a safety system configured to provide a signal to allow intervention to avoid unsafe conditions due to active metal ion catalyzed decomposition of hydrogen peroxide, the safety system comprising
      (i) a first sensor disposed at or in the first reaction catalyst column and configured for measuring pressure;
      (ii) a second sensor disposed at or in the first pretreatment column and configured for measuring pressure; and
      (iii) a processor configured for determining the difference between the pressure measured by the first sensor and the second sensor and providing a detectable signal if the difference meets or exceeds a predetermined value.

2. The apparatus of claim 1, wherein the first pretreatment column comprises a strong cation exchanger in acid or inert metal form.

3. The apparatus of claim 1, wherein the reaction catalyst comprises a strong acid catalyst that can be physically removed from the reaction mixture.

4. The apparatus of claim 3, wherein the reaction catalyst comprises a strong cation exchanger in acid form.

5. The apparatus of claim 3, wherein the reaction catalyst comprises an inorganic compound comprising an insoluble strong acid.

6. The apparatus of claim 1, further comprising: a second, a third, and a fourth reaction catalyst column;
the first, second, third, and fourth reaction catalyst columns being coupled in series.

7. The apparatus of claim 6, wherein the reaction catalyst comprises a strong acid catalyst.

8. The apparatus of claim 6, wherein the reaction catalyst comprises a strong cation exchanger in acid form.

9. The apparatus of claim 6, wherein the reaction catalyst comprises an inorganic compound comprising an insoluble strong acid.

* * * * *